(12) United States Patent
Bharadwaj et al.

(10) Patent No.: US 10,821,442 B2
(45) Date of Patent: *Nov. 3, 2020

(54) DEVICES, SYSTEMS, AND KITS FOR FORMING DROPLETS

(71) Applicant: 10X Genomics, Inc., Pleasanton, CA (US)

(72) Inventors: Rajiv Bharadwaj, Pleasanton, CA (US); Anthony Makarewicz, Livermore, CA (US); Bill Kengli Lin, Pleasanton, CA (US)

(73) Assignee: 10X Genomics, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/977,812

(22) Filed: May 11, 2018

(65) Prior Publication Data
US 2019/0060890 A1 Feb. 28, 2019

Related U.S. Application Data

(60) Provisional application No. 62/614,312, filed on Jan. 5, 2018, provisional application No. 62/571,754, filed
(Continued)

(51) Int. Cl.
*B01L 3/02* (2006.01)
*B01L 3/00* (2006.01)
(Continued)

(52) U.S. Cl.
CPC ...... *B01L 3/502784* (2013.01); *B01F 3/0807* (2013.01); *B01F 3/0811* (2013.01); *B01F 5/048* (2013.01); *B01F 5/0473* (2013.01); *B01F 5/0478* (2013.01); *B01F 11/0241* (2013.01); *B01F 13/0062* (2013.01); *B01F 13/0071* (2013.01); *B01L 3/0241* (2013.01); *B01L 3/50273* (2013.01); *B01L 3/502761* (2013.01); *C12Q 1/6806* (2013.01); *G01N 33/54313* (2013.01); *G01N 33/58* (2013.01); *B01L 2200/0647* (2013.01);
(Continued)

(58) Field of Classification Search
CPC combination set(s) only.
See application file for complete search history.

(56) References Cited

U.S. PATENT DOCUMENTS 5,700,692 A 12/1997 Sweet
5,837,200 A 11/1998 Diessel et al.
(Continued)

FOREIGN PATENT DOCUMENTS

GB 2097692 A 11/1982
WO WO-2004/002627 A2 1/2004
(Continued)

OTHER PUBLICATIONS

Abate et al., "Beating Poisson encapsulation statistics using close-packed ordering," Lab Chip. 9(18):2628-31 (2009).
(Continued)

*Primary Examiner* — Brian R Gordon
(74) *Attorney, Agent, or Firm* — Clark & Elbing LLP

(57) ABSTRACT

Devices, systems, and their methods of use, for generating droplets are provided. One or more geometric parameters of a microfluidic channel can be selected to generate droplets of a desired and predictable droplet size.

18 Claims, 17 Drawing Sheets

Related U.S. Application Data on Oct. 12, 2017, provisional application No. 62/548,755, filed on Aug. 22, 2017.

(51) Int. Cl.

| | | |
|---|---|---|
| *B01F 5/04* | (2006.01) | |
| *G01N 33/543* | (2006.01) | |
| *B01F 3/08* | (2006.01) | |
| *B01F 13/00* | (2006.01) | |
| *B01F 11/02* | (2006.01) | |
| *C12Q 1/6806* | (2018.01) | |
| *G01N 33/58* | (2006.01) | |
| *C12Q 1/686* | (2018.01) | |
| *C40B 40/06* | (2006.01) | |

(52) U.S. Cl.
CPC ......... *B01L 2200/0652* (2013.01); *B01L 2200/0673* (2013.01); *B01L 2300/0851* (2013.01); *B01L 2300/161* (2013.01); *B01L 2400/086* (2013.01); *C12N 2533/50* (2013.01); *C12Q 1/686* (2013.01); *C12Q 2563/185* (2013.01); *C40B 40/06* (2013.01)

(56) References Cited

U.S. PATENT DOCUMENTS

| | | |
|---|---|---|
| 6,057,149 A | 5/2000 | Burns et al. |
| 6,123,798 A | 9/2000 | Gandhi et al. |
| 6,176,962 B1 | 1/2001 | Soane et al. |
| 6,177,479 B1 | 1/2001 | Nakajima et al. |
| 6,281,018 B1 | 8/2001 | Kirouac et al. |
| 6,778,724 B2 | 8/2004 | Wang et al. |
| 6,808,075 B2 | 10/2004 | Bohm et al. |
| 6,877,528 B2 | 4/2005 | Gilbert et al. |
| 6,915,679 B2 | 7/2005 | Chien et al. |
| 6,976,590 B2 | 12/2005 | Deshpande et al. |
| 6,994,218 B2 | 2/2006 | Kawano et al. |
| 7,104,405 B2 | 9/2006 | Bohm et al. |
| 7,241,988 B2 | 7/2007 | Gruber et al. |
| 7,264,972 B2 | 9/2007 | Foster |
| 7,452,725 B2 | 11/2008 | Leary et al. |
| 7,569,788 B2 | 8/2009 | Deshpande et al. |
| 7,584,857 B2 | 9/2009 | Bohm et al. |
| 7,622,076 B2 | 11/2009 | Davies et al. |
| 7,699,767 B2 | 4/2010 | Mueth et al. |
| 7,704,395 B2 | 4/2010 | Mueth et al. |
| 7,723,116 B2 | 5/2010 | Evans et al. |
| 7,767,444 B2 | 8/2010 | Liu et al. |
| 7,772,287 B2 | 8/2010 | Higuchi et al. |
| 7,901,947 B2 | 3/2011 | Pollack et al. |
| 7,927,797 B2 | 4/2011 | Nobile et al. |
| 7,943,671 B2 | 5/2011 | Herminghaus et al. |
| 7,963,399 B2 | 6/2011 | Bohm et al. |
| 8,029,744 B2 | 10/2011 | Noda et al. |
| 8,096,421 B2 | 1/2012 | Shinoda |
| 8,186,913 B2 | 5/2012 | Toner et al. |
| 8,198,092 B2 | 6/2012 | Durack et al. |
| 8,241,914 B2 | 8/2012 | Durack et al. |
| 8,246,805 B2 | 8/2012 | Shinoda |
| 8,298,767 B2 | 10/2012 | Brenner et al. |
| 8,387,803 B2 | 3/2013 | Thorslund et al. |
| 8,408,399 B2 | 4/2013 | Bohm et al. |
| 8,454,906 B2 | 6/2013 | Mathies et al. |
| 8,467,040 B2 | 6/2013 | Luscher |
| 8,524,173 B2 | 9/2013 | Yamanaka et al. |
| 8,529,026 B2 | 9/2013 | Clarke et al. |
| 8,563,274 B2 | 10/2013 | Brenner et al. |
| 8,567,608 B2 | 10/2013 | Deshpande et al. |
| 8,592,221 B2 | 11/2013 | Fraden et al. |
| 8,609,422 B2 | 12/2013 | Durack et al. |
| 8,613,890 B2 | 12/2013 | Muraki |
| 8,633,015 B2 | 1/2014 | Ness et al. |
| 8,658,368 B2 | 2/2014 | Quake et al. |
| 8,658,430 B2 | 2/2014 | Miller et al. |
| 8,679,756 B1 | 3/2014 | Brenner et al. |
| 8,741,192 B2 | 6/2014 | Torii et al. |
| 8,795,500 B2 | 8/2014 | Shinoda |
| 8,807,879 B2 | 8/2014 | Toner et al. |
| 8,820,538 B1 | 9/2014 | Lin |
| 8,821,006 B2 | 9/2014 | Norikane et al. |
| 8,857,462 B2 | 10/2014 | Miller et al. |
| 8,871,500 B2 | 10/2014 | Foster et al. |
| 8,944,083 B2 | 2/2015 | Collier et al. |
| 8,986,628 B2 | 3/2015 | Stone et al. |
| 9,012,390 B2 | 4/2015 | Holtze et al. |
| 9,017,623 B2 | 4/2015 | Fraden et al. |
| 9,089,844 B2 | 7/2015 | Hiddessen et al. |
| 9,102,980 B2 | 8/2015 | Brenner et al. |
| 9,108,173 B2 | 8/2015 | Lee et al. |
| 9,126,160 B2 | 9/2015 | Ness et al. |
| 9,132,394 B2 | 9/2015 | Makarewicz, Jr. et al. |
| 9,133,009 B2 | 9/2015 | Baroud et al. |
| 9,156,010 B2 | 10/2015 | Colston, Jr. et al. |
| 9,194,861 B2 | 11/2015 | Hindson et al. |
| 9,207,160 B2 | 12/2015 | Shinoda |
| 9,216,392 B2 | 12/2015 | Hindson et al. |
| 9,248,417 B2 | 2/2016 | Hindson et al. |
| 9,266,104 B2 | 2/2016 | Link |
| 9,273,308 B2 | 3/2016 | Link et al. |
| 9,328,376 B2 | 5/2016 | Hiddessen et al. |
| 9,339,850 B2 | 5/2016 | Deshpande et al. |
| 9,388,465 B2 | 7/2016 | Hindson et al. |
| 9,393,560 B2 | 7/2016 | Ness et al. |
| 9,399,215 B2 | 7/2016 | Cauley, III et al. |
| 9,403,294 B2 | 8/2016 | Cauley, III |
| 9,409,174 B2 | 8/2016 | Makarewicz, Jr. et al. |
| 9,410,149 B2 | 8/2016 | Brenner et al. |
| 9,410,150 B2 | 8/2016 | Brenner et al. |
| 9,410,201 B2 | 8/2016 | Hindson et al. |
| 9,417,190 B2 | 8/2016 | Hindson et al. |
| 9,427,737 B2 | 8/2016 | Heredia et al. |
| 9,486,757 B2 | 11/2016 | Romanowsky et al. |
| 9,492,797 B2 | 11/2016 | Makarewicz et al. |
| 9,500,664 B2 | 11/2016 | Ness et al. |
| 9,527,049 B2 | 12/2016 | Hiddessen et al. |
| 9,562,837 B2 | 2/2017 | Link |
| 9,567,631 B2 | 2/2017 | Hindson et al. |
| 9,623,384 B2 | 4/2017 | Hindson et al. |
| 9,638,620 B2 | 5/2017 | Di Carlo et al. |
| 9,644,204 B2 | 5/2017 | Hindson et al. |
| 9,683,792 B2 | 6/2017 | Possinger et al. |
| 9,687,848 B2 | 6/2017 | Makarewicz, Jr. et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,700,891 B2 | 7/2017 | Smith et al. |
| 9,701,998 B2 | 7/2017 | Hindson et al. |
| 9,702,808 B2 | 7/2017 | Lin |
| 9,764,322 B2 | 9/2017 | Hiddessen et al. |
| 9,824,068 B2 | 11/2017 | Wong |
| 9,856,530 B2 | 1/2018 | Hindson et al. |
| 9,946,577 B1 | 4/2018 | Stafford et al. |
| 9,951,386 B2 | 4/2018 | Hindson et al. |
| 9,975,122 B2 | 5/2018 | Masquelier et al. |
| 10,071,377 B2 | 9/2018 | Bharadwaj et al. |
| 10,137,449 B2 | 11/2018 | Bharadwaj et al. |
| 10,150,117 B2 | 12/2018 | Bharadwaj et al. |
| 10,357,771 B2 | 7/2019 | Bharadwaj et al. |
| 10,544,413 B2 | 1/2020 | Bharadwaj et al. |
| 10,549,279 B2 | 2/2020 | Bharadwaj et al. |
| 2002/0058332 A1 | 5/2002 | Quake et al. |
| 2002/0127736 A1 | 9/2002 | Chou et al. |
| 2003/0228610 A1 | 12/2003 | Seul |
| 2004/0068019 A1 | 4/2004 | Higuchi et al. |
| 2004/0109793 A1 | 6/2004 | McNeely et al. |
| 2005/0103690 A1 | 5/2005 | Kawano et al. |
| 2005/0249636 A1 | 11/2005 | Tacklind et al. |
| 2005/0266582 A1 | 12/2005 | Modlin et al. |
| 2006/0078888 A1 | 4/2006 | Griffiths et al. |
| 2006/0078893 A1 | 4/2006 | Griffiths et al. |
| 2007/0065808 A1 | 3/2007 | Bohm et al. |
| 2007/0117086 A1 | 5/2007 | Evans et al. |
| 2007/0166200 A1 | 7/2007 | Zhou et al. |

(56) References Cited

U.S. PATENT DOCUMENTS

| | | |
|---|---|---|
| 2007/0196397 A1 | 8/2007 | Torii et al. |
| 2008/0003142 A1 | 1/2008 | Link et al. |
| 2008/0038810 A1 | 2/2008 | Pollack et al. |
| 2008/0050283 A1 | 2/2008 | Chou et al. |
| 2008/0053205 A1 | 3/2008 | Pollack et al. |
| 2008/0056948 A1 | 3/2008 | Dale et al. |
| 2008/0138876 A1 | 6/2008 | Ragsdale |
| 2008/0166720 A1 | 7/2008 | Hsieh et al. |
| 2008/0295909 A1 | 12/2008 | Locascio et al. |
| 2009/0012187 A1 | 1/2009 | Chu et al. |
| 2009/0035770 A1 | 2/2009 | Mathies et al. |
| 2009/0047713 A1 | 2/2009 | Handique |
| 2009/0131543 A1 | 5/2009 | Weitz et al. |
| 2009/0155563 A1 | 6/2009 | Petsev et al. |
| 2009/0235990 A1 | 9/2009 | Beer |
| 2009/0269248 A1 | 10/2009 | Falb et al. |
| 2009/0269824 A1 | 10/2009 | Kim et al. |
| 2009/0325217 A1 | 12/2009 | Luscher |
| 2010/0006441 A1 | 1/2010 | Renaud et al. |
| 2010/0022414 A1 | 1/2010 | Link et al. |
| 2010/0022680 A1 | 1/2010 | Karnik et al. |
| 2010/0105866 A1 | 4/2010 | Fraden et al. |
| 2010/0163109 A1 | 7/2010 | Fraden et al. |
| 2010/0184928 A1 | 7/2010 | Kumacheva |
| 2010/0216208 A1 | 8/2010 | Mueth et al. |
| 2011/0005978 A1 | 1/2011 | Bohm et al. |
| 2011/0053798 A1 | 3/2011 | Hindson et al. |
| 2011/0086377 A1 | 4/2011 | Thwar et al. |
| 2011/0223314 A1 | 9/2011 | Zhang et al. |
| 2011/0267457 A1 | 11/2011 | Weitz et al. |
| 2012/0015382 A1 | 1/2012 | Weitz et al. |
| 2012/0091059 A1 | 4/2012 | Beer et al. |
| 2012/0121480 A1 | 5/2012 | Frenz et al. |
| 2012/0122714 A1 | 5/2012 | Samuels et al. |
| 2012/0142018 A1 | 6/2012 | Jiang |
| 2012/0196288 A1 | 8/2012 | Beer |
| 2012/0199226 A1 | 8/2012 | Weitz et al. |
| 2012/0211084 A1 | 8/2012 | Weitz et al. |
| 2012/0219947 A1 | 8/2012 | Yurkovetsky et al. |
| 2012/0220494 A1 | 8/2012 | Samuels et al. |
| 2012/0222748 A1 | 9/2012 | Weitz et al. |
| 2012/0231444 A1 | 9/2012 | Quake et al. |
| 2012/0236299 A1 | 9/2012 | Chiou et al. |
| 2012/0301869 A1 | 11/2012 | Evans |
| 2012/0315690 A1 | 12/2012 | Di Carlo et al. |
| 2013/0046030 A1 | 2/2013 | Rotem et al. |
| 2013/0059310 A1 | 3/2013 | Brenner et al. |
| 2013/0064776 A1 | 3/2013 | El Harrak et al. |
| 2013/0084572 A1 | 4/2013 | Hindson et al. |
| 2013/0109575 A1 | 5/2013 | Kleinschmidt et al. |
| 2013/0130919 A1 | 5/2013 | Chen et al. |
| 2013/0149737 A1 | 6/2013 | Seidel et al. |
| 2013/0203172 A1 | 8/2013 | Wex et al. |
| 2013/0236901 A1 | 9/2013 | Potier et al. |
| 2013/0281316 A1 | 10/2013 | Ismagilov et al. |
| 2013/0337575 A1 | 12/2013 | Fox et al. |
| 2014/0024023 A1 | 1/2014 | Cauley, III et al. |
| 2014/0080226 A1 | 3/2014 | Cauley, III et al. |
| 2014/0087412 A1 | 3/2014 | Fouras et al. |
| 2014/0155295 A1 | 6/2014 | Hindson et al. |
| 2014/0161685 A1 | 6/2014 | Lee et al. |
| 2014/0179544 A1 | 6/2014 | Steenblock et al. |
| 2014/0199730 A1 | 7/2014 | Agresti et al. |
| 2014/0220350 A1 | 8/2014 | Kim et al. |
| 2014/0221239 A1 | 8/2014 | Carman et al. |
| 2014/0235506 A1 | 8/2014 | Hindson et al. |
| 2014/0272996 A1 | 9/2014 | Bemis |
| 2014/0273198 A1 | 9/2014 | Saito et al. |
| 2014/0273201 A1 | 9/2014 | Saito et al. |
| 2014/0273202 A1 | 9/2014 | Saito et al. |
| 2014/0287963 A1 | 9/2014 | Hindson et al. |
| 2014/0312534 A1 | 10/2014 | Cauley, III |
| 2014/0326339 A1 | 11/2014 | Toner et al. |
| 2014/0338753 A1 | 11/2014 | Sperling et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0017648 A1 | 1/2015 | Hiddessen et al. |
| 2015/0031034 A1 | 1/2015 | Hindson et al. |
| 2015/0034163 A1 | 2/2015 | Abate et al. |
| 2015/0050688 A1 | 2/2015 | Thrasher et al. |
| 2015/0066385 A1 | 3/2015 | Schnall-Levin et al. |
| 2015/0224466 A1 | 8/2015 | Hindson et al. |
| 2015/0258543 A1 | 9/2015 | Baroud et al. |
| 2015/0267246 A1 | 9/2015 | Baroud et al. |
| 2015/0292988 A1 | 10/2015 | Bharadwaj et al. |
| 2015/0298091 A1 | 10/2015 | Weitz et al. |
| 2015/0336096 A1 | 11/2015 | Smith et al. |
| 2015/0352597 A1 | 12/2015 | Deshpande et al. |
| 2015/0355071 A1 | 12/2015 | Gluckstad |
| 2015/0360236 A1 | 12/2015 | Garcia et al. |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol et al. |
| 2016/0053303 A1 | 2/2016 | Brenner et al. |
| 2016/0059204 A1 | 3/2016 | Hindson et al. |
| 2016/0091145 A1 | 3/2016 | Weitz et al. |
| 2016/0097087 A1 | 4/2016 | Wiyatno et al. |
| 2016/0122817 A1 | 5/2016 | Jarosz et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0250637 A1 | 9/2016 | Neild et al. |
| 2016/0257984 A1 | 9/2016 | Hardenbol et al. |
| 2016/0271576 A1 | 9/2016 | Arab et al. |
| 2016/0281136 A1 | 9/2016 | Jarosz et al. |
| 2016/0281137 A1 | 9/2016 | Jarosz et al. |
| 2016/0281138 A1 | 9/2016 | Jarosz et al. |
| 2016/0281160 A1 | 9/2016 | Jarosz et al. |
| 2016/0281161 A1 | 9/2016 | Jarosz et al. |
| 2016/0299053 A1 | 10/2016 | Jiang |
| 2016/0304860 A1 | 10/2016 | Hindson et al. |
| 2016/0314242 A1 | 10/2016 | Schnall-Levin et al. |
| 2016/0332163 A1 | 11/2016 | Wang et al. |
| 2016/0348093 A1 | 12/2016 | Price et al. |
| 2016/0362724 A1 | 12/2016 | Bailey et al. |
| 2017/0009274 A1 | 1/2017 | Abate et al. |
| 2017/0014824 A1 | 1/2017 | Boyd et al. |
| 2017/0016041 A1 | 1/2017 | Greenfield et al. |
| 2017/0028365 A1 | 2/2017 | Link et al. |
| 2017/0056884 A1 | 3/2017 | Hiddessen et al. |
| 2017/0065979 A1 | 3/2017 | Ness et al. |
| 2017/0080425 A1 | 3/2017 | Toner et al. |
| 2017/0106134 A1 | 4/2017 | Dreschel et al. |
| 2017/0114385 A1 | 4/2017 | Di Carlo et al. |
| 2017/0122861 A1 | 5/2017 | Lin |
| 2017/0128937 A1 | 5/2017 | Hung et al. |
| 2017/0128938 A9 | 5/2017 | Gilbert et al. |
| 2017/0128940 A1 | 5/2017 | Amini et al. |
| 2017/0128943 A1 | 5/2017 | Fraden et al. |
| 2017/0136461 A1 | 5/2017 | Smith et al. |
| 2017/0144161 A1 | 5/2017 | Hindson et al. |
| 2017/0145476 A1 | 5/2017 | Ryvkin et al. |
| 2017/0151536 A1 | 6/2017 | Weitz et al. |
| 2017/0159109 A1 | 6/2017 | Zheng et al. |
| 2017/0165663 A1 | 6/2017 | Hong et al. |
| 2017/0175179 A1 | 6/2017 | Hiddessen et al. |
| 2017/0235876 A1 | 8/2017 | Jaffe et al. |
| 2017/0246638 A1 | 8/2017 | Possinger et al. |
| 2017/0260584 A1 | 9/2017 | Zheng et al. |
| 2017/0282145 A1 | 10/2017 | Merten et al. |
| 2017/0291174 A1 | 10/2017 | Makarewicz, Jr. et al. |
| 2017/0321252 A1 | 11/2017 | Hindson et al. |
| 2017/0335385 A1 | 11/2017 | Hindson et al. |
| 2017/0342404 A1 | 11/2017 | Hindson et al. |
| 2017/0348691 A1 | 12/2017 | Bharadwaj et al. |
| 2017/0356027 A1 | 12/2017 | Hindson et al. |
| 2017/0362587 A1 | 12/2017 | Hindson et al. |

(56) References Cited

U.S. PATENT DOCUMENTS

| | | |
|---|---|---|
| 2018/0008984 A1 | 1/2018 | Bharadwaj et al. |
| 2018/0015472 A1 | 1/2018 | Bharadwaj et al. |
| 2018/0015473 A1 | 1/2018 | Bharadwaj et al. |
| 2018/0030512 A1 | 2/2018 | Hindson et al. |
| 2018/0030515 A1 | 2/2018 | Regev et al. |
| 2018/0051321 A1 | 2/2018 | Hindson et al. |
| 2018/0056294 A1 | 3/2018 | Di Carlo et al. |
| 2018/0080075 A1 | 3/2018 | Brenner et al. |
| 2018/0094298 A1 | 4/2018 | Hindson et al. |
| 2018/0094312 A1 | 4/2018 | Hindson et al. |
| 2018/0094313 A1 | 4/2018 | Hindson et al. |
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112253 A1 | 4/2018 | Hindson et al. |
| 2018/0112266 A1 | 4/2018 | Hindson et al. |
| 2018/0142292 A1 | 5/2018 | Hindson et al. |
| 2018/0236443 A1 | 8/2018 | Masquelier et al. |
| 2018/0334670 A1 | 11/2018 | Bharadwaj et al. |
| 2019/0060904 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0351417 A1 | 11/2019 | Bharadwaj et al. |

FOREIGN PATENT DOCUMENTS

| | | |
|---|---|---|
| WO | WO-2004/091763 A2 | 10/2004 |
| WO | WO-2006/040551 A2 | 4/2006 |
| WO | WO-2007/140015 A2 | 12/2007 |
| WO | WO-2008/121342 A2 | 10/2008 |
| WO | WO-2010/104604 A1 | 9/2010 |
| WO | WO-2010/128858 A1 | 11/2010 |
| WO | WO-2012/013316 A1 | 2/2012 |
| WO | WO-2012/142664 A1 | 10/2012 |
| WO | WO-2012/156744 A2 | 11/2012 |
| WO | WO-2012/167142 A2 | 12/2012 |
| WO | WO-2013/096643 A1 | 6/2013 |
| WO | WO-2013/112121 A1 | 8/2013 |
| WO | WO-2014/028378 A2 | 2/2014 |
| WO | WO-2014/117784 A1 | 8/2014 |
| WO | WO-2014/165559 A2 | 10/2014 |
| WO | WO-2014/210353 A2 | 12/2014 |
| WO | WO-2015/015199 A2 | 2/2015 |
| WO | WO-2015/076251 A1 | 5/2015 |
| WO | WO-2015/132317 A1 | 9/2015 |
| WO | WO-2015/132318 A1 | 9/2015 |
| WO | WO-2015/134984 A1 | 9/2015 |
| WO | WO-2015/157567 A1 | 10/2015 |
| WO | WO-2015/160919 A1 | 10/2015 |
| WO | WO-2015/164212 A1 | 10/2015 |
| WO | WO-2015/191534 A2 | 12/2015 |
| WO | WO-2015/200869 A1 | 12/2015 |
| WO | WO-2015/200871 A1 | 12/2015 |
| WO | WO-2015/200893 A2 | 12/2015 |
| WO | WO-2016/035284 A1 | 3/2016 |
| WO | WO-2016/065056 A1 | 4/2016 |
| WO | WO-2016/069939 A1 | 5/2016 |
| WO | WO-2016/075172 A1 | 5/2016 |
| WO | WO-2016/085742 A1 | 6/2016 |
| WO | WO-2016/087068 A1 | 6/2016 |
| WO | WO-2016/114970 A1 | 7/2016 |
| WO | WO-2016/115273 A1 | 7/2016 |
| WO | WO-2016/130578 A1 | 8/2016 |
| WO | WO-2016/137973 A1 | 9/2016 |
| WO | WO-2016/138148 A1 | 9/2016 |
| WO | WO-2016/149096 A1 | 9/2016 |
| WO | WO-2016/151107 A1 | 9/2016 |
| WO | WO-2016/168584 A1 | 10/2016 |
| WO | WO-2016/174229 A1 | 11/2016 |
| WO | WO-2016/187179 A1 | 11/2016 |
| WO | WO-2016/187256 A2 | 11/2016 |
| WO | WO-2017/005872 A1 | 1/2017 |
| WO | WO-2017/015123 A1 | 1/2017 |
| WO | WO-2017/060876 A1 | 4/2017 |
| WO | WO-2017/070056 A1 | 4/2017 |
| WO | WO-2017/075549 A1 | 5/2017 |
| WO | WO-2017/083375 A1 | 5/2017 |
| WO | WO-2017/087910 A1 | 5/2017 |
| WO | WO-2017/096158 A1 | 6/2017 |
| WO | WO-2017/117490 A1 | 7/2017 |
| WO | WO-2017/138984 A1 | 8/2017 |
| WO | WO-2017/139690 A1 | 8/2017 |
| WO | WO-2017/180949 A1 | 10/2017 |
| WO | WO-2017/184707 A1 | 10/2017 |
| WO | WO-2017/197338 A1 | 11/2017 |
| WO | WO-2017/197343 A2 | 11/2017 |
| WO | WO-2018/039338 A1 | 3/2018 |
| WO | WO-2018/075693 A1 | 4/2018 |
| WO | WO-2018/213643 A1 | 11/2018 |
| WO | WO-2018/226546 A1 | 12/2018 |
| WO | WO-2019/040637 A1 | 2/2019 |

OTHER PUBLICATIONS

Abate et al., "High-throughput injection with microfluidics using picoinjectors," Proc Natl Acad Sci U S A. 107(45): 19163-6 (2010).

Abate et al., "Valve based flow focusing for drop formation," Appl Phys Lett. 94(2):023503-1-3 (2009) (3 pages).

AGC Chemicals, "Amorphous Fluoropolymer CYTOP:Chemistry for a Blue Planet," Jul. 2015 (10 pages).

AGC Chemicals, "Water/oil-repellent fluororesin coating material CYTOP(TM)," 2015 (1 page).

Aghvami et al., "Rapid prototyping of cyclic olefin copolymer (COC) microfluidic devices," Sens Actuators B Chem. 247: 940-949 (2017).

Akartuna et al., "Chemically induced coalescence in droplet-based microfluidics," Lab Chip. DOI:10.1039/c4lc01285b (2014) (5 pages).

Akselband et al., "Enrichment of slow-growing marine microorganisms from mixed cultures using gel microdrop (GMD) growth assay and fluorescence-activated cell sorting," J Exp Mar Bio Ecol. 329(2): 196-205 (2006).

Akselband et al., "Rapid mycobacteria drug susceptibility testing using Gel Microdrop (GMD) Growth Assay and flow cytometry," J Microbiol Methods. 62(2): 181-197 (2005).

Anna et al., "Formation of dispersions using 'flow focusing' in microchannels," Appl Phys Lett. 82(3): 364-366 (2003).

Attia et al., "Micro-injection moulding of polymer microfluidic devices," Microfluid Nanofluidics. 7(1): 1-28 (2009) (30 pages).

Baret et al., "Fluorescence-activated droplet sorting (FADS): efficient microfluidic cell sorting based on enzymatic activity," Lab Chip. 9(13): 1850-1859 (2009).

Baret, "Surfactants in droplet-based microfluidics," Lab Chip.12(3): 422-433 (2012).

Becker et al., "Polymer microfabrication technologies for microfluidic systems," Anal Bioanal Chem. 390(1): 89-111 (2008).

Beer et al., "On-chip, real-time, single-copy polymerase chain reaction in picoliter droplets," Anal Chem. 79(22): 8471-8475 (2007).

Boone et al. "Plastic advances microfluidic devices," Anal Chem. 74(3): 78A-86A (2002).

Braeckmans et al., "Scanning the code. Encoded microcarrier beads signal the way to better combinatorial libraries and biological assays," Modern Drug Discovery. 6(2):28-30; 32 (2003) (4 pages).

Bransky et al., "A microfluidic droplet generator based on a piezo-electric actuator," Lab Chip. 9(4): 516-520 (2009).

Brouzes et al., "Droplet microfluidic technology for single-cell high-throughput screening," Proc Natl Acad Sci U S A. 106(34): 14195-14200 (2009).

Burns et al. "Microfabricated structures for integrated DNA analysis," Proc Natl Acad Sci U S A. 93(11): 5556-5561 (1996).

Burns et al., "An integrated nanoliter DNA analysis device," Science. 282(5388): 484-487 (1998).

Burns et al., "The intensification of rapid reactions in multiphase systems using slug flow in capillaries," Lab Chip. 1(1): 10-15 (2001).

Carroll et al. "The selection of high-producing cell lines using flow cytometry and cell sorting," Expert Opin Biol Ther. 4(11): 1821-1829 (2004).

(56) References Cited

OTHER PUBLICATIONS

Chakraborty et al., "Microfluidic step-emulsification in axisymmetric geometry," Lab Chip. 17(21): 3609-3620 (2017).
Chechetkin et al. "Sequencing by hybridization with the generic 6-mer oligonucleotide microarray: an advanced scheme for data processing," J Biomol Struct Dyn. 18(1): 83-101 (2000).
Chen et al. "Chemical transfection of cells in picoliter aqueous droplets in fluorocarbon oil," Anal Chem. 83(22): 8816-8820 (2011).
Chien et al., "Multiport flow-control system for lab-on-a-chip microfluidic devices," Fresenius J Anal Chem. 371(2): 106-11 (2001).
Chokkalingam et al., "Probing cellular heterogeneity in cytokine-secreting immune cells using droplet-based microfluidics," Lab Chip. 13(24): 4740-4744 (2013).
Chokkalingam et al., "Self-synchronizing pairwise production of monodisperse droplets by microfluidic step emulsification," Appl Phys Lett. 93(25): 254101-1-254101-3 (2008).
Chou et al., "Disposable microdevices for DNA analysis and cell sorting," Proc Solid-State Sensor and Actuator Workshop, Jun. 8-11, Hilton Head, SC, pp. 11-14 (1998).
Chu et al., "Controllable monodisperse multiple emulsions," Angew Chem Int Ed. 46(47): 8970-8974 (2007).
Clausell-Tormos et al. "Droplet-based microfluidic platforms for the encapsulation and screening of mammalian cells and multicellular organisms," Chem Biol. 15(5): 427-437 (2008).
Curcio, Mario, Thesis: "Improved techniques for high-throughput molecular diagnostics," Doctor of Philosophy, Royal Institute of Technology, 2002 (131 pages).
Damean et al., "Simultaneous measurement of reactions in microdroplets filled by concentration gradients," Lab Chip. 9(12): 1707-1713 (2009).
Dangla et al., "Droplet microfluidics driven by gradients of confinement," Proc Natl Acad Sci U S A. 110(3): 853-858 (2013).
Dangla et al., "The physical mechanisms of step emulsification," J Phys D Appl Phys. 46(11):114003 (2013) (8 pages).
De Bruin et al., "UBS investment research: Q-Series: DNA sequencing," UBS Securities LLC. Jul. 12, pp. 1-15 (2007).
De Mello et al., Chip technology for micro-separation. *Microsystem Technology: Biomethods*, vol. 10. Köhler J.M., Mejevaia T., Saluz H.P., 129-177 (1999).
Demirci et al., "Single cell epitaxy by acoustic picolitre droplets," Lab Chip. 7(9): 1139-1145 (2007).
Doerr, "The smallest bioreactor," Nat Methods. 2(5): 326 (2005).
Dowding et al., "Oil core/polymer shell microcapsules by internal phase separation from emulsion droplets. II: Controlling the release profile of active molecules," Langmuir. 21(12): 5278-5284 (2005).
Draper et al., "Compartmentalization of electrophoretically separated analytes in a multiphase microfluidic platform," Anal Chem. 84(13): 5801-5808 (2012).
Dressler et al., "Droplet-based microfluidics: enabling impact on drug discovery," J Biomol Screen. 19(4): 483-496 (2014).
Drmanac et al., "Sequencing by hybridization (SBH): advantages, achievements, and opportunities," Adv Biochem Eng Biotechnol. 77: 75-101 (2002).
Duffy et al., "Rapid prototyping of microfluidic systems in poly(dimethylsiloxane)," Anal Chem. 70(23): 4974-4984 (1998).
Eastburn et al., "Ultrahigh-throughput mammalian single-cell reverse-transcriptase polymerase chain reaction in microfluidic drops," Anal Chem. 85(16): 8016-8021 (2013).
Eggersdorfer et al, "Supplementary Information: Tandem emulsification for high-throughput production of double emulsions," Lab Chip. 17(5):936-942 (2017) (2 pages).
Eggersdorfer et al, "Tandem emulsification for high-throughput production of double emulsions," Lab Chip. 17(5): 936-942 (2017).
Esser-Kahn et al., "Triggered release from polymer capsules," Macromolecules. 44(14): 5539-5553 (2011).
Fisher et al., "A scalable, fully automated process for construction of sequence-ready human exome targeted capture libraries," Genome Biol. 12(1):R1 (2011) (15 pages).

Fredrickson et al., "Macro-to-micro interfaces for microfluidic devices," Lab Chip. 4(6): 526-533 (2004).
Freiberg et al., "Polymer microspheres for controlled drug release," Int J Pharm. 282(1-2): 1-18 (2004).
Fu et al., "A microfabricated fluorescence-activated cell sorter," Nature Biotechnol. 17(11): 1109-1111 (1999).
Fulton et al., "Advanced multiplexed analysis with the FlowMetrix system," Clin Chem. 43(9): 1749-1756 (1997).
Gai et al., "Spatiotemporal periodicity of dislocation dynamics in a two-dimensional microfluidic crystal flowing in a tapered channel," Proc Natl Acad Sci U S A. 113(43):12082-12087 (2016).
Gai et al., "Supporting Information: Spatiotemporal periodicity of dislocation dynamics in a two-dimensional microfluidic crystal flowing in a tapered channel," Proc Natl Acad Sci U S A. 1-9 (2016).
Galambos et al., "Precision alignment packaging for microsystems with multiple fluid connections," Proceedings of 2001 ASME: International Mechanical Engineering Conference and Exposition, Nov. 11-16, New York, NY. pp. 1-8 (2001).
Garstecki et al., "Formation of monodisperse bubbles in a microfluidic flow-focusing device," Appl Phys Lett. 85(13): 2649-2651 (2004).
Gartner et al., "The microfluidic toolbox—examples for fluidic interfaces and standardization concepts," Proc SPIE Int Soc Opt Eng. 6 pages (2003).
Ghadessy et al., "Directed evolution of polymerase function by compartmentalized self replication," Proc Natl Acad Sci U S A. 98(8): 4552-4557 (2001).
Granieri, Lucia, Thesis: "Droplet-based microfluidics and engineering of tissue plasminogen activator for biomedical applications," Doctor of Philosophy, L'Universite de Strasbourg, 2009 (131 pages).
Grasland-Mongrain et al., "Droplet coalescence in microfluidic devices," http://www.eleves.ens.fr./home/grasland/rapports/stage4.pdf, retrieved Jun. 4, 2007.
Guo et al., "Droplet microfluidics for high-throughput biological assays," Lab Chip. 21(12): 2146-2155 (2012).
Gyarmati et al., "Reversible disulphide formation in polymer networks: A versatile functional group from synthesis to applications," Eur Polym J. 49(6): 1268-1286 (2013).
Hashimshony et al., "CEL-Seq: Single-cell RNA-seq by multiplexed linear amplification," Cell Rep. 2(3): 666-673 (2012) (14 pages).
Hati et al., "Production of monodisperse drops from viscous fluids," Lab Chip. DOI: 10.1039/c7lc01322a (2018) (7 pages).
He et al., "Selective encapsulation of single cells and subcellular organelles into picoliter- and femtoliter-volume droplets," Anal Chem. 77(6): 1539-1544 (2005).
Holtze et al., "Biocompatible surfactants for water-in-fluorocarbon emulsions," Lab Chip. 8(10): 1632-1639 (2008).
Hosokawa et al., "Massively parallel whole genome amplification for single-cell sequencing using droplet microfluidics," Sci Rep. 7(1): 5199 (2017) (11 pages).
Huang et al., "Coating of poly(dimethylsiloxane) with n-dodecyl-Beta-D-maltoside to minimize nonspecific protein adsorption," Lab Chip. 5(10):1005-1007 (2005).
Huang et al., "Collective generation of milliemulsions by step-emulsification," RSC Adv. 7(24): 14932-14938 (2017).
Huebner et al., "Quantitative detection of protein expression in single cells using droplet microfluidics," Chem Commun. 12:1218-1220 (2007).
Hug et al., "Measurement of the number of molecules of a single mRNA species in a complex mRNA preparation," J Theor Biol. 221(4): 615-624 (2003).
Hwang et al., "Surface modification of cyclic olefin copolymer substrate by oxygen plasma treatment," Surf Coat Tech. 202(15): 3669-3674 (2008).
Jena et al., "Cyclic olefin copolymer based microfluidic devices for biochip applications: Ultraviolet surface grafting using 2-methacryloyloxyethyl phosphorylcholine," Biomicrofluidics. 6(1): 012822-1-012822-12 (2012) (12 pages).
Jung et al., "Micro machining of injection mold inserts for fluidic channel of polymeric biochips," Sensors. 7(8): 1643-1654 (2007).
Kahkeshani et al., "Drop formation using ferrofluids driven magnetically in a step emulsification device," Lab Chip. 16(13): 2474-2480 (2016).

(56) References Cited

OTHER PUBLICATIONS

Katsura et al., "Indirect micromanipulation of single molecules in water-in-oil emulsion," Electrophoresis. 22(2): 289-293 (2001).
Kawai et al., Mass-production system of nearly monodisperse diameter gel particles using droplets formation in a microchannel. *Micro Total Analysis Systems 2002*, vol. 1. Baba Y., Shoji S., van den Berg A., 368-370 (2002).
Kenis et al., "Microfabrication inside capillaries using multiphase laminar flow patterning," Science. 285(5424): 83-85 (1999).
Khomiakova et al., "Analysis of perfect and mismatched DNA duplexes by a generic hexanucleotide microchip," Mol Biol (Mosk). 37(4): 726-741 (2003) (English abstract only) (1 page).
Kim et al., "Albumin loaded microsphere of amphiphilic poly(ethylene glycol)/poly(alpha-ester) multiblock copolymer," Eur J Pharm Sci. 23(3): 245-251 (2004).
Kim et al., "Fabrication of monodisperse gel shells and functional microgels in microfluidic devices," Angew Chem Int Ed Engl. 46(11): 1819-1822 (2007) (5 pages).
Kim et al., "Rapid prototyping of microfluidic systems using a PDMS/polymer tape composite," Lab Chip. 9(9): 1290-1293 (2009).
Klein et al., "Droplet barcoding for single-cell transcriptomics applied to embryonic stem cells," Cell. 161(5): 1187-1201 (2015) (22 pages).
Kobayashi et al., "Effect of slot aspect ratio on droplet formation from silicon straight-through microchannels," J Colloid Interface Sci. 279(1):277-80 (2004).
Kobayashi et al., "Preparation characteristics of oil-in-water emulsions using differently charged surfactants in straight-through microchannel emulsification," Colloids Surf A Physicochem Eng Asp. 229(1-3): 33-41 (2003).
Köster et al., "Drop-based microfluidic devices for encapsulation of single cells," Lab Chip. 8(7): 1110-1115 (2008).
Lagally et al., "Single-molecule DNA amplification and analysis in an integrated microfluidic device," Anal Chem. 73(3): 565-570 (2001).
Lagus et al., "A review of the theory, methods, and recent applications of high-throughput single-cell droplet microfluidics," J Phys D: Appl Phys. 46: 114005 (21 pages) (2013).
Li et al., "Step-emulsification in a microfluidic device," Lab Chip. 15(4):1023-31 (2015).
Li et al., Microfluidic Lab-on-a-Chip. *Ewing's Analytical Instrumentation Handbook.*. Cazes, J., 581-679 (2005) (120 pages).
Loscertales et al., "Micro/nano encapsulation via electrified coaxial liquid jets," Science. 295(5560): 1695-1698 (2002).
Love et al., "A microengraving method for rapid selection of single cells producing antigen specific antibodies," Nat Biotechnol. 24(6): 703-707 (2006).
Lowe, Adam, Thesis: "Norbornenes and [n]polynorbornanes as molecular scaffolds for anion recognition," Doctor of Philosophy, Deakin University, 2010 (361 pages).
Maan et al., "Microfluidic emulsification in food processing," J Food Eng. 147:1-7 (2015).
Maan et al., "Spontaneous droplet formation techniques for monodisperse emulsions preparation—Perspectives for food applications," J Food Eng. 107(3-4):334-46 (2011).
Macosko et al., "Supplemental Information: Highly parallel genome-wide expression profiling of individual cells using nanoliter droplets," Cell. 161(5): 1202-1214 (2015) (31 pages).
Mair et al., "Injection molded microfluidic chips featuring integrated interconnects," Lab Chip. 6(10): 1346-1354 (2006).
Makino et al., "Preparation of hydrogel microcapsules effects of preparation conditions upon membrane properties," Colloids Surf B Biointerfaces. 12(2): 97-104 (1998).
Man, Piu, Dissertation:"Monolithic structures for integrated microfluidic analysis," Doctor of Philosophy, the University of Michigan, 2001 (144 pages).
Mazutis et al., "Selective droplet coalescence using microfluidic systems," Lab Chip. 12(10): 1800-1806 (2012).
Mazutis et al., "Single-cell analysis and sorting using droplet-based microfluidics," available in PMC Aug. 11, 2014. Published in final edited form as Nat Protoc. 8(5): 870-891 (2013) (48 pages).
Merriman et al., "Progress in ion torrent semiconductor chip based sequencing," Electrophoresis. 33(23): 3397-3417 (2012).
Mittal et al., "Dynamics of step-emulsification: From a single to a collection of emulsion droplet generators," Phys Fluids. 26: 082109-1-082109-14 (2014).
Moore et al., "Behavior of capillary valves in centrifugal microfluidic devices prepared by three-dimensional printing," Microfluid Nanofluid. 10(4): 877-888 (2011).
Navin, "The first five years of single-cell cancer genomics and beyond," Genome Res. 25(10): 1499-1507 (2015).
Nisisako et al., "Droplet formation in a microchannel network," Lab Chip. 2(1): 24-26 (2002).
Nisisako et al., "Droplet formation in a microchannel on PMMA plate," *Micro Total Analysis Systems 2001*. Ramsey, J.M., van den Berg, A., 137-138 (2001).
Nisisako et al., "Microfluidic large-scale integration on a chip for mass production of monodisperse droplets and particles," Lab Chip. 8(2): 287-293 (2008).
Novak et al., "Single cell multiplex gene detection and sequencing using microfluidically-generated agarose emulsions," Available in PMC Jan. 10, 2012, published in final edited form as: Angew Chem Int Ed Engl. 50(2):390-5 (2011) (10 pages).
Oberholzer et al., "Polymerase chain reaction in liposomes," Chem Biol. 2(10):677-82 (1995).
Ogawa et al., "Production and characterization of O/W emulsions containing cationic droplets stabilized by lecithin-chitosan membranes," J Agric Food Chem. 51(9):2806-12 (2003).
Okushima et al., "Controlled production of monodisperse double emulsions by two-step droplet breakup in microfluidic devices," Langmuir. 20(23):9905-8 (2004).
Perez et al., "Poly(lactic acid)-poly(ethylene glycol) nanoparticles as new carriers for the delivery of plasmid DNA," J Control Release. 75(1-2):211-24 (2001).
Priest et al., "Generation of monodisperse gel emulsions in a microfluidic device," Appl Phys Lett. 88: 024106-1-024106-3 (2006).
Ramsey, J.M., "The burgeoning power of the shrinking laboratory," Nat Biotechnol. 17(11):1061-2 (1999).
Rotem et al., "High-throughput single-cell labeling (Hi-SCL) for RNA-Seq using drop-based microfluidics," PLoS One. 10(5):e0116328 (2015) (14 pages).
Rotem et al., "Single cell chip-seq using drop-based microfluidics," Frontiers of Single Cell Analysis, Sep. 5-7, Stanford, CA. Abstract 50 (2013) (1 page).
Ryan et al., "Rapid assay for mycobacterial growth and antibiotic susceptibility using gel microdrop encapsulation," J Clin Microbiol. 33(7):1720-6 (1995).
Sahin et al., "Microfluidic EDGE emulsification: the importance of interface interactions on droplet formation and pressure stability," Sci Rep. 6(26407):1-7 (2016).
Schirinzi et al., "Combinatorial sequencing-by-hybridization: analysis of the NF1 gene," Genet Test. 10(1):8-17 (2006).
Schmitt et al., "Bead-based multiplex genotyping of human papillomaviruses," J Clin Microbiol. 44(2):504-12 (2006).
Schuler et al., "Digital droplet PCR on disk," Lab Chip. 16 (1): 208-216 (2016).
Seiffert et al., "Smart microgel capsules from macromolecular precursors," J Am Chem Soc. 132(18):6606-9 (2010).
Shah et al., "Fabrication of monodisperse thermosensitive microgels and gel capsules in microfluidic devices," Soft Matter. 4:2303-9 (2008).
Shim et al., "Supporting Information: Control and measurement of the phase behavior of aqueous solutions using microfluidics," S1-S13 (2007) (13 pages).
Song et al., "Reactions in droplets in microfluidic channels," Angew Chem Int Ed Engl. 45(44):7336-56 (2006).
Stolovicki et al., "Throughput enhancement of parallel step emulsifier devices by shear-free and efficient nozzle clearance," Lab Chip. DOI: 10.1039/c7lc01037k (2017) (7 pages).

(56) References Cited

OTHER PUBLICATIONS

Su et al., "Microfluidics-based biochips: technology issues, implementation platforms, and design-automation challenges," IEEE Transactions on Computer-Aided Design of Integrated Circuits and Systems. 25(2):211-23 (2006).

Sun et al., "Progress in research and application of liquid phase chip technology," China Journal of Experimental Surgery. 22(5) (2005) (5 pages).

Tawfik et al., "Man-made cell-like compartments for molecular evolution," Nat Biotechnol. 16(7):652-6 (1998).

Tewhey et al., "Microdroplet-based PCR enrichment for large-scale targeted sequencing," Nat Biotechnol. 27(11):1025-31 (2009) (11 pages).

Theberge et al., "Microdroplets in microfluidics: an evolving platform for discoveries in chemistry and biology," Angew Chem Int Ed Engl. 49(34):5846-68 (2010).

Thorsen et al., "Dynamic pattern formation in a vesicle-generating microfluidic device," Phys Rev Lett. 86(18):4163-6 (2001).

Tubeleviciute et al., "Compartmentalized self-replication (CSR) selection of Thermococcus litoralis Sh1B DNA polymerase for diminished uracil binding," Protein Eng Des Sel. 23(8):589-97 (2010).

Turner et al., "Methods for genomic partitioning," Annu Rev Genomics Hum Genet. 10:263-84 (2009).

Van Dijke et al., "EDGE emulsification for food-grade dispersions," J Food Eng. 97(3): 348-354 (2010).

Van Dijke et al., "Effect of viscosities of dispersed and continuous phases in microchannel oil-in-water emulsification," Microfluid Nanofluid. 9(1):77-85 (2010).

Van Dijke et al., "Microchannel Emulsification: From Computational Fluid Dynamics to Predictive Analytical Model," Langmuir. 24(18): 10107-10115 (2008).

Van Dijke et al., "Parallelized edge-based droplet generation (EDGE) devices," Lab Chip. 9(19): 2824-2830 (2009).

Van Dijke et al., "Simultaneous Formation of Many Droplets in a Single Microfluidic Droplet Formation Unit," AIChE J. 56(3): 833-836 (2010).

Van Dijke et al., "The mechanism of droplet formation in microfluidic EDGE systems," Soft Matter. 6(2): 321-330 (2010).

Wagner et al., "Biocompatible fluorinated polyglycerols for droplet microfluidics as an alternative to PEG-based copolymer surfactants," Lab Chip. 16(1):65-9 (2016) (7 pages).

Wang et al., "A novel thermo-induced self-bursting microcapsule with magnetic-targeting property," Chemphyschem. 10(14):2405-9 (2009).

Ward et al., "Microfluidic flow focusing: drop size and scaling in pressure versus flow-rate-driven pumping," Electrophoresis. 26(19):3716-24 (2005).

Weaver et al., "Rapid clonal growth measurements at the single-cell level: gel microdroplets and flow cytometry," Biotechnology (N Y). 9(9):873-7 (1991).

Weigl et al., "Microfluidic diffusion-based separation and detection," Science. 283:346-7 (1999) (4 pages).

Whitesides et al., "Flexible methods for microfluidics," Phys Today. 54(6): 42-48 (2001).

Williams et al., "Amplification of complex gene libraries by emulsion PCR," Nat Methods. 3(7):545-50 (2006).

Zeng et al., "High-performance single cell genetic analysis using microfluidic emulsion generator arrays," Anal Chem. 82(8):3183-90 (2010).

Zhao et al., "Preparation of hemoglobin-loaded nano-sized particles with porous structure as oxygen carriers," Biomaterials. 28(7):1414-22 (2007).

Zilionis et al., "Single-cell barcoding and sequencing using droplet microfluidics," Nat Protoc. 12(1): 44-73 (2017).

Zong et al., "Genome-wide detection of single-nucleotide and copy-number variations of a single human cell," Science. 338(6114):1622-6 (2012) (6 pages).

U.S. Appl. No. 15/977,805, 10X Genomics, Inc.
U.S. Appl. No. 15/977,824, 10X Genomics, Inc.
U.S. Appl. No. 15/977,861, 10X Genomics, Inc.
U.S. Appl. No. 15/977,875, 10X Genomics, Inc.
International Search Report and Written Opinion for International Application No. PCT/US2018/047551, dated Nov. 15, 2018 (17 pages).

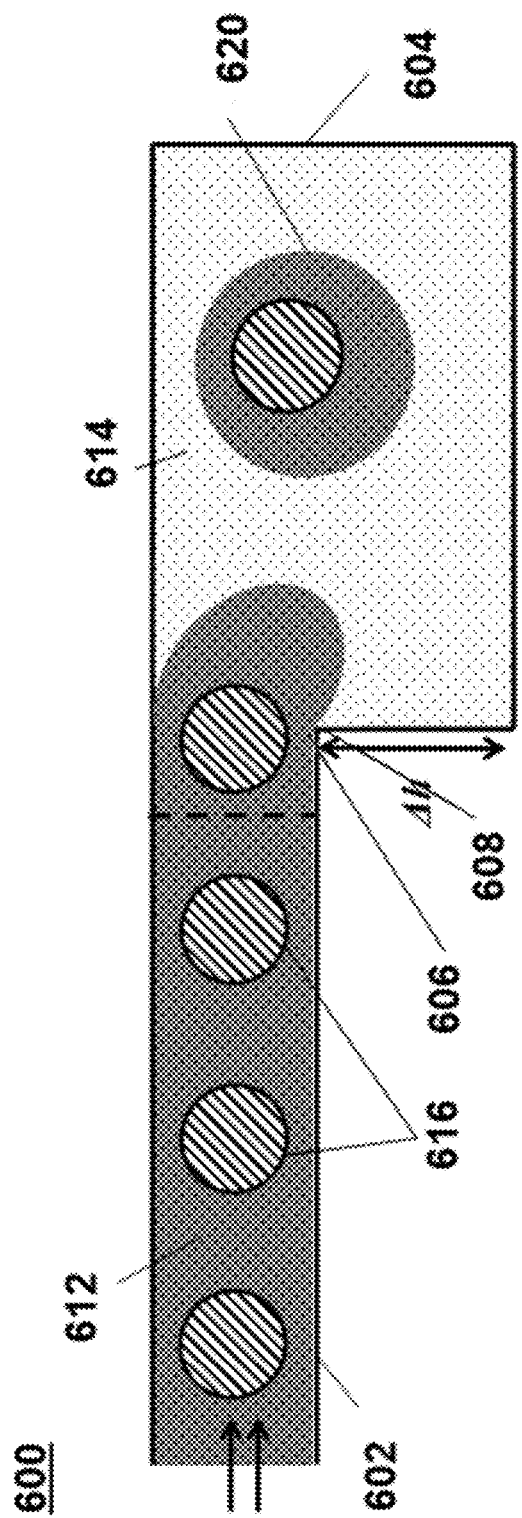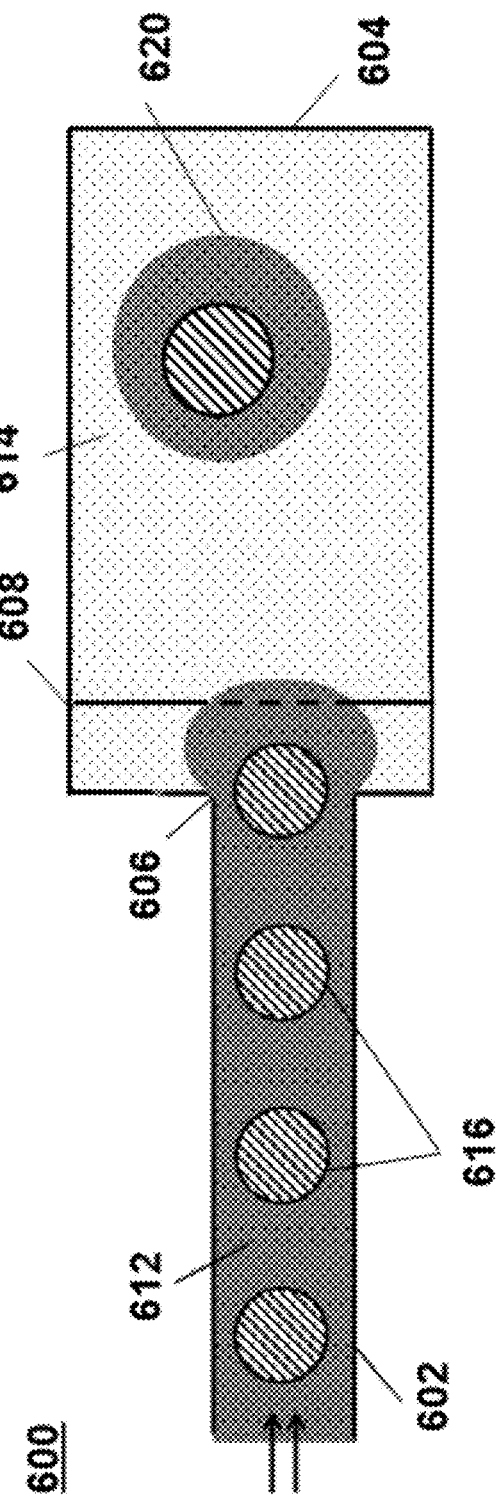
FIG. 6A
FIG. 6B

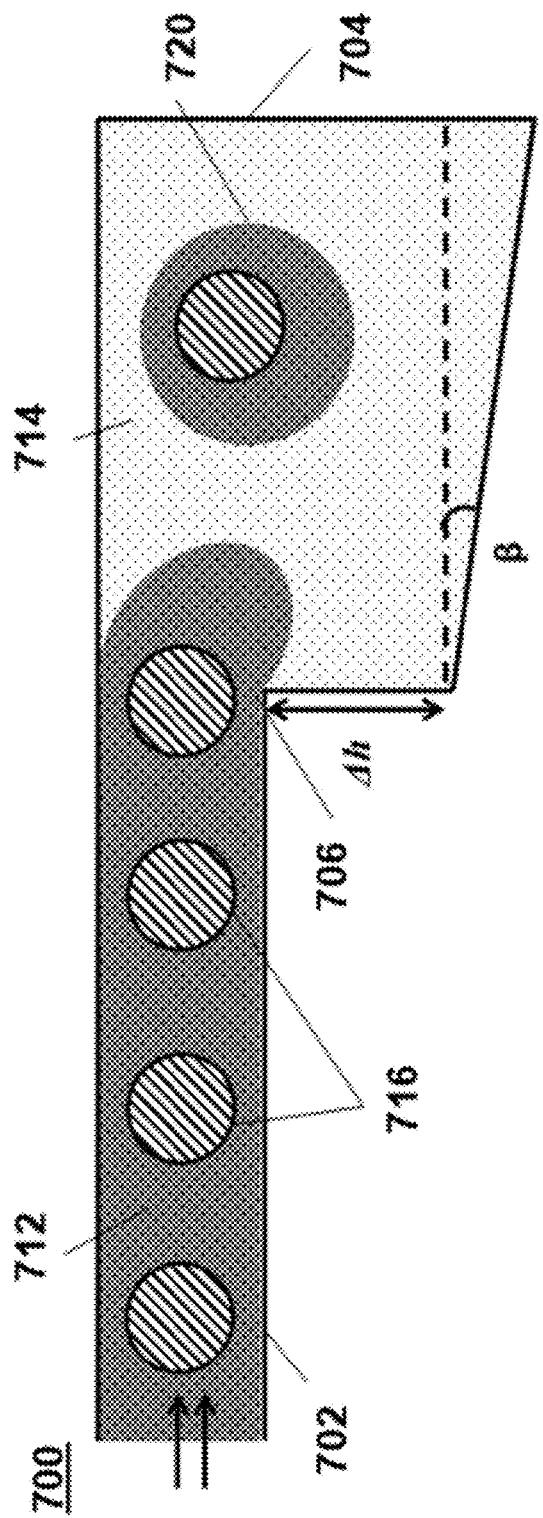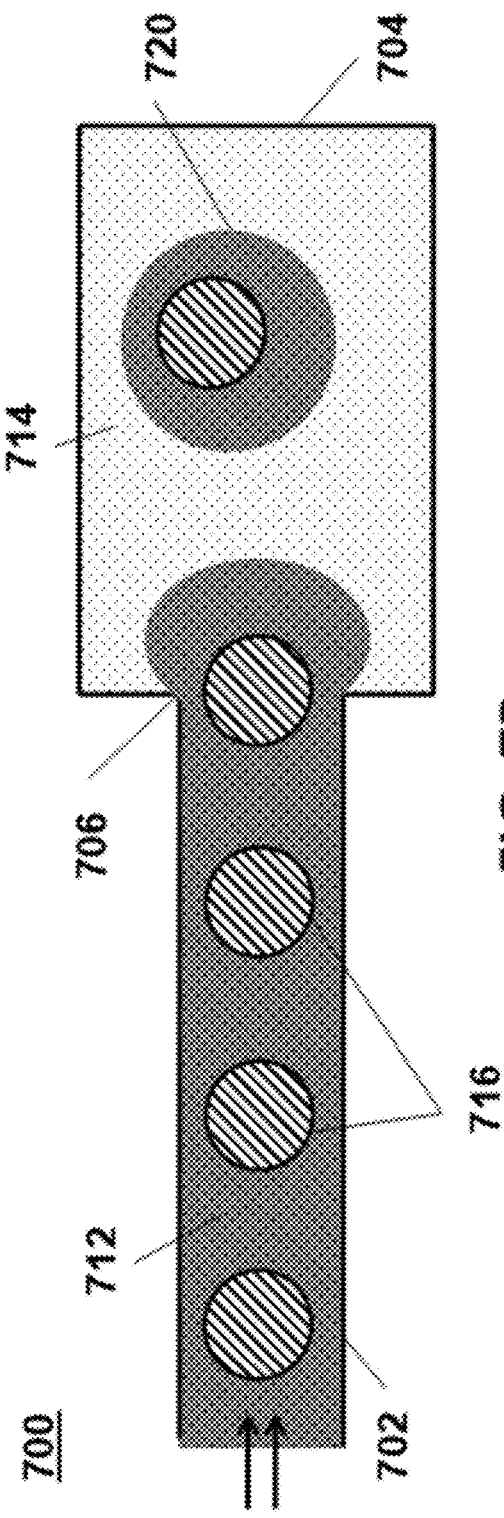
FIG. 7A
FIG. 7B

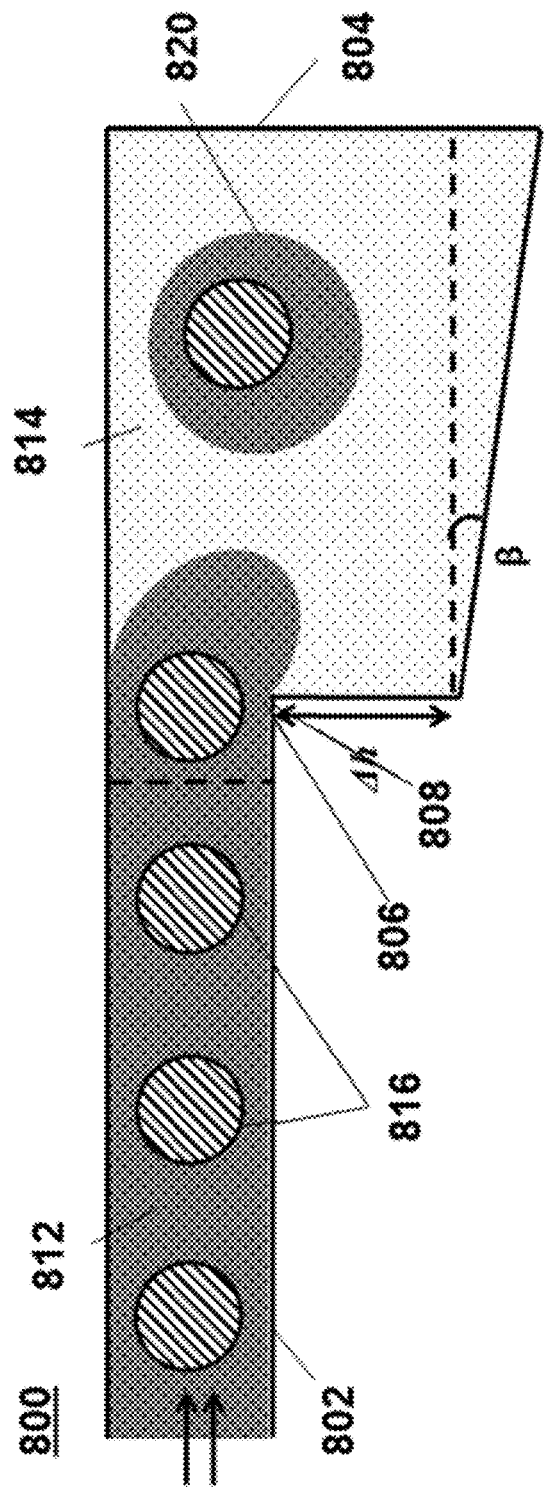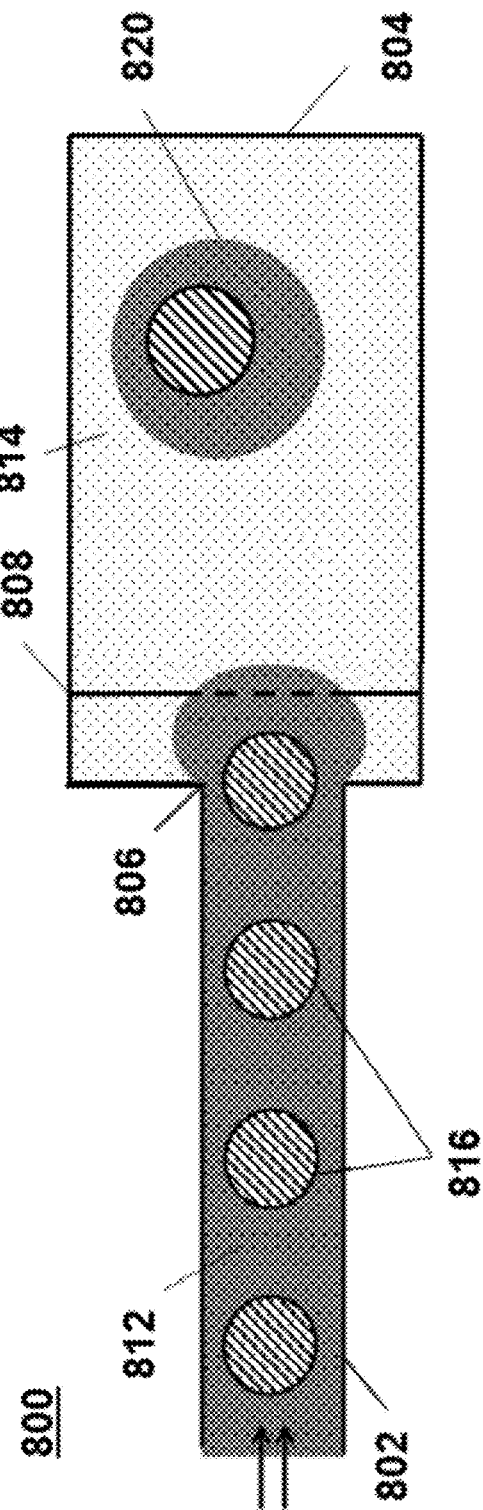

A

B

A.

B.

C.

D.

E.

A. 1100

B.

C.

D.

A.

B.

A.

B.

A.

B.

A.

Step 1: channels empty

Step 2: fill left channels with blocking fluid (dark gray)

Step 3: add coating agent (light gray)

Step 4: flush entire chip, coating remains at desired region (hatched)

B.

DEVICES, SYSTEMS, AND KITS FOR FORMING DROPLETS

BACKGROUND OF THE INVENTION

Many biomedical applications rely on high-throughput assays of samples combined with one or more reagents in droplets. For example, in both research and clinical applications, high-throughput genetic tests using target-specific reagents are able to provide information about samples in drug discovery, biomarker discovery, and clinical diagnostics, among others.

Improved devices and methods for producing droplets would be beneficial.

SUMMARY OF THE INVENTION

We have developed a microfluidic device that is capable of producing droplets of a first liquid in a second liquid that is immiscible with the first liquid.

In one aspect, the invention provides a device for producing droplets of a first liquid in a second liquid. The device includes a channel and a droplet formation region configured to allow a liquid flowing from the channel to expand in at least one dimension, e.g., having a shelf region, a step region, or both.

In one embodiment, the device includes a) a first channel having a first depth, a first width, a first proximal end, and a first distal end; b) a second channel having a second depth, a second width, a second proximal end, and a second distal end, where the second channel intersects the first channel between the first proximal and first distal ends; and c) a droplet formation region including a shelf region having a third depth and a third width, and a step region having a fourth depth, where the shelf region is configured to allow the first liquid to expand in at least one dimension and has at least one inlet and at least one outlet, and where the shelf region is disposed between the first distal end and the step region. The first channel and droplet formation region are configured to produce droplets of the first liquid in the second liquid.

In some embodiments, the first liquid contains particles. In certain embodiments, the first channel and the droplet formation region are configured to produce droplets including a single particle or a single particle of multiple types, e.g., one bead and one cell. In some embodiments, the third width increases from the inlet of the shelf region to the outlet of the shelf region.

In certain embodiments, the device includes a first reservoir and a second reservoir in fluid communication with the first proximal end and the second proximal end, respectively. In further embodiments, the device includes a collection reservoir configured to collect droplets formed in the droplet formation region. In certain embodiments, the step region and collection reservoir do not have orthogonal elements that contact the droplets when formed. In some embodiments, where the device is configured to produce a population of droplets that are substantially stationary in the collection reservoir.

In some embodiments, the device includes a third channel having a third proximal end and a third distal end, where the third proximal end is in fluid communication with the shelf region and where the third distal end is in fluid communication with the step region.

In further embodiments, the device includes a plurality of first channels, second channels, and droplet formation regions, e.g., that are fluidically independent to produce an array.

In a related aspect, the invention includes a system for producing droplets of a first liquid in a second liquid, the system including a) a device for producing droplets, where the device includes i) a first channel having a first depth, a first width, a first proximal end, and a first distal end; ii) a second channel having a second depth, a second width, a second proximal end, and a second distal end, where the second channel intersects the first channel between the first proximal and first distal ends; iii) a droplet formation region having a shelf region having a third depth and a third width and a step region having a fourth depth, where the shelf region is configured to allow the first liquid to expand in at least one dimension and has at least one inlet and at least one outlet, where the shelf region is disposed between the first distal end and the step region; iv) a first reservoir in fluid communication with the first proximal end, where the first reservoir includes at least one portion of the first liquid; and v) a second reservoir in fluid communication with the second proximal end, where the second reservoir comprises at least one portion of the first liquid, and b) a second liquid contained in the droplet formation region, e.g., where the first liquid and the second liquid are immiscible. The portions of the first liquid are miscible and combine at the intersection of the first channel and second channel to form the first liquid.

In some embodiments, a portion of the first liquid in the first reservoir comprises particles. In certain embodiments, a portion of the first liquid in the second reservoir comprises an analyte.

In certain embodiments, the first channel and the droplet formation region of the device are configured to produce droplets including a single particle or a single particle of multiple types, e.g., one bead and one cell. In some embodiments, the third width of the device increases from the inlet of the shelf region to the outlet of the shelf region. In certain embodiments, the device of the system includes a collection reservoir configured to collect droplets formed in the droplet formation region.

In further embodiments, the device of the system includes a third channel having a third proximal end and a third distal end, where the third proximal end is in fluid communication with the shelf region and where the third distal end is in fluid communication with the step region. In further embodiments, the device of the system includes a plurality of first channels, second channels, and droplet formation regions.

The system may also include a controller operatively coupled to transport the portion of the first liquid in the first liquid and the portion of first liquid in the second reservoir to the intersection.

In another related aspect, the invention includes a kit for producing droplets of a first liquid in a second liquid, the kit including a) a device for producing droplets, where the device includes i) a first channel having a first depth, a first width, a first proximal end, and a first distal end; ii) a second channel having a second depth, a second width, a second proximal end, and a second distal end, where the second channel intersects the first channel between the first proximal and first distal ends; iii) a droplet formation region having a shelf region having a third depth and a third width and a step region having a fourth depth, where the shelf region is configured to allow the first liquid to expand in at least one dimension and has at least one inlet and at least one outlet, where the shelf region is disposed between the first distal end and the step region; iv) a first reservoir in fluid communication with the first proximal end; and v) a second reservoir in fluid communication with the second proximal end; b) a portion of the first liquid; and c) a second liquid, e.g., that is immiscible with the first liquid. The device is configured to produce droplets of the first liquid in the second liquid.

In some embodiments, the first liquid contains particles. In certain embodiments, the first channel and the droplet formation region are configured to produce droplets including a single particle or a single particle of multiple types, e.g., one bead and one cell. In some embodiments, the third width increases from the inlet of the shelf region to the outlet of the shelf region. In some embodiments, the third width of the device increases from the inlet of the shelf region to the outlet of the shelf region.

In further embodiments, the device of the kit includes a collection reservoir configured to collect droplets formed in the droplet formation region. In certain embodiments, the device is configured to produce a population of droplets that are substantially stationary in the collection reservoir.

In further embodiments, the device of the kit includes a third channel having a third proximal end and a third distal end, where the third proximal end is in fluid communication with the shelf region and where the third distal end is in fluid communication with the step region. In further embodiments, the device of the kit includes a plurality of first channels, second channels, and droplet formation regions.

In another aspect, the invention provides a device for producing droplets of a first liquid in a second liquid, the device having a) a first channel having a first depth, a first width, a first proximal end, a first distal end, and a first surface having a first water contact angle; and b) a droplet formation region having a second surface having a second water contact angle. The droplet formation region may be configured to allow the first liquid to expand in at least one dimension. The droplet formation region may have at least one inlet and at least one outlet. The second water contact angle may be greater than the first water contact angle. The first channel and droplet formation region are configured to produce droplets of the first liquid in the second liquid.

In some embodiments, the device further includes a second channel having a second depth, a second width, a second proximal end, and a second distal end. The second channel may intersect the first channel between the first proximal and first distal ends.

In certain embodiments, the droplet formation region includes a shelf region having a third depth and a third width. In particular embodiments, the droplet formation region includes a step region having a fourth depth.

In further embodiments, the second contact angle is 5° to 100° greater than the first contact angle. In yet further embodiments, the second water contact angle is at least 100°.

In some embodiments, the device further includes a first reservoir in fluid communication with the first proximal end. In particular embodiments, the device further includes a second reservoir in fluid communication with the second proximal end. In certain embodiments, the device further includes a collection reservoir configured to collect droplets formed in the droplet formation region. In further embodiments, the device is configured to produce a population of droplets that are substantially stationary in the collection reservoir.

In yet further embodiments, the first liquid includes particles. In still further embodiments, the first channel and the droplet formation region are configured to produce droplets including a single particle or a single particle of multiple types, e.g., one bead and one cell.

In another related aspect, the invention provides a system for producing droplets of a first liquid in a second liquid. In some embodiments, the system includes: a) a device for producing droplets, the device including: i) a first channel having a first depth, a first width, a first proximal end, a first distal end, and a first surface having a first water contact angle; ii) a droplet formation region having a second surface having a second water contact angle; and iii) a first reservoir in fluid communication with the first proximal end and comprising at least a portion of the first liquid; and b) a second liquid contained in the droplet formation region. The first liquid and the second liquid may be immiscible. The droplet formation region may be configured to allow the first liquid to expand in at least one dimension. The droplet formation region may have at least one inlet and at least one outlet. The second water contact angle may be greater than the first water contact angle. The system may be configured to produce droplets of the first liquid in the second liquid.

In certain embodiments, the first reservoir further includes particles.

In particular embodiments, the device further includes a second channel having a second depth, a second width, a second proximal end, and a second distal end. The second channel may intersect the first channel between the first proximal and first distal ends.

In some embodiments, the device further includes a second reservoir in fluid communication with the second proximal end and contains at least one portion of the first liquid. In further embodiment, the portion of the first liquid in the first channel and the portion of the first liquid in the second channel combine at the intersection of the first channel and second channel to form the first liquid.

In yet further embodiments, the droplet formation region includes a shelf region having a third depth and a third width at or distal to the at least one inlet of the droplet formation region. In still further embodiments, the droplet formation region includes a step region having a fourth depth at or distal to the at least one outlet of the droplet formation region.

In particular embodiments, the second contact angle is 5° to 100° greater than the first contact angle. In certain embodiments, the second water contact angle is at least 100°.

In some embodiments, the device further includes a collection reservoir configured to collect droplets formed in the droplet formation region. In further embodiments, the device is configured to produce a population of droplets that are substantially stationary in the collection reservoir. In yet further embodiments, the system further includes a controller operatively coupled to transport the portion of the first liquid in the first reservoir and the portion of first liquid in the second reservoir to the intersection.

In another aspect, the invention provides a method of producing a microfluidic device including a surface modification.

In some embodiments, the method includes: (i) providing a primed microfluidic device including a channel in fluid communication with a droplet formation region having a primed surface; and (ii) contacting the primed surface with a coating agent having affinity for the primed surface to produce a surface having a water contact angle. The droplet formation region may be configured to allow a liquid exiting the channel to expand in at least one dimension. The contact angle may be greater than the water contact angle of the primed surface and greater than the water contact angle of the channel.

In certain embodiments, the method further includes producing the primed microfluidic device by depositing a layer of metal oxide onto an unmodified droplet formation region surface. In particular embodiments, the coating agent is in a coating carrier (e.g., a coating liquid or coating gas).

In further embodiments, step (ii) includes filling the channel with a blocking liquid that is substantially immiscible with the coating carrier (e.g., the coating liquid). Filling the channel with a blocking liquid may substantially prevent ingress of the coating agent into the channel.

In particular embodiments, step (ii) includes supplying a gas to the channel, wherein the gas pressure substantially prevents ingress of the coating agent into the channel.

In some embodiments, the microfluidic device further includes a coating feed channel. The coating feed channel may be in fluid communication with the droplet formation region. The coating agent may be provided to the droplet formation region through the coating feed channel.

In another aspect, the invention provides a device for producing droplets of a first fluid in a second fluid, the device including a) a first channel having a first depth, a first width, a first proximal end, and a first distal end; b) a second channel having a second depth, a second width, a second proximal end, and a second distal end, where the second channel intersects the first channel between the first proximal and first distal ends; and c) a plurality of droplet formation regions, where the droplet formation region is configured to allow the first liquid to expand in at least one dimension and has at least one inlet and at least one outlet. The first channel and droplet formation regions are configured to produce droplets of the first liquid in the second liquid. Devices of this aspect of the invention can include surfaces having a surface modification, e.g., alteration to the water contact angle of the surface.

In some embodiments, the first fluid contains particles. In certain embodiments, the first channel and the droplet formation region are configured to produce droplets including a single particle or a single particle of multiple types, e.g., one bead and one cell.

In some embodiments, at least one of the droplet formation regions includes a shelf region having a third depth and a third width.

In some embodiments, at least one of the droplet formation regions includes a step region having a fourth depth. In further embodiments, at least one of the droplet formation regions includes a shelf region that is disposed between the first distal end and the step region.

In further embodiments, the device includes a collection reservoir configured to collect a population of droplets formed in the droplet formation region.

In another embodiment, the device includes a) two first channels, each having a first depth, a first width, a first proximal end, and a first distal end; b) two second channels each having a second depth, a second width, a second proximal end, and a second distal end, where each of the second distal ends intersects one of the first channels between the first proximal and first distal ends and where one of the second channels traverses but does not intersect at least one first channel; and c) a plurality of droplet formation regions, where each droplet formation region is configured to allow the first liquid to expand in at least one dimension and has at least one inlet and at least one outlet and each droplet formation region is connected to one of the first distal ends. The two first channels and the droplet formation regions are configured to produce droplets of the first liquid in the second liquid. Devices of this embodiment of the invention can include surfaces having a surface modification, e.g., alteration to the water contact angle of the surface.

In some embodiments, the first fluid contains particles. In certain embodiments, the first channel and the droplet formation region are configured to produce droplets including a single particle or a single particle of multiple types, e.g., one bead and one cell.

In some embodiments, at least one of the droplet formation regions includes a shelf region having a third depth and a third width. In some embodiments, at least one of the droplet formation regions includes a step region having a fourth depth. In further embodiments, at least one of the droplet formation regions includes a shelf region that is disposed between the first distal end and the step region.

In further embodiments, the device includes a collection reservoir configured to collect a population of droplets formed in the droplet formation region. In some embodiments, the first proximal ends are in fluid communication with a first reservoir. In some embodiments, the second proximal ends are in fluid communication with a second reservoir.

In certain embodiments, the first proximal end of one first channel intersects the other first channel. In certain embodiments, the second proximal end of one second channel intersects the other second channel.

In yet another embodiment, the device includes a) two first channels, each having a first depth, a first width, a first proximal end, and a first distal end; b) two second channels each having a second depth, a second width, a second proximal end, and a second distal end, where the two second channels intersect the two first channels between the first proximal and first distal ends; and c) two droplet formation regions, where the droplet formation regions are configured to allow the first liquid to expand in at least one dimension and have at least one inlet and at least one outlet. The two first channels and the two droplet formation regions are configured to produce droplets of the first liquid in the second liquid. Devices of this embodiment of the invention can include surfaces having a surface modification, e.g., alteration to the water contact angle of the surface.

In some embodiments, the first fluid contains particles.

In some embodiments, the two droplet formation regions include a shelf region having a third depth and a third width. In further embodiments, the two droplet formation regions include a step region having a fourth depth.

In further embodiments, the device includes a collection reservoir configured to collect a population of droplets formed in the two droplet formation regions. In some embodiments, the first proximal ends are in fluid communication with a first reservoir. In some embodiments, the second proximal ends are in fluid communication with a second reservoir.

In some embodiments, the first proximal end of one first channel intersects the other first channel. In some embodiments, the second proximal end of one second channel intersects the other second channel.

In a further aspect, the invention provides a method of producing droplets of a first liquid in a second liquid.

In some embodiments, the method includes a) providing a device including: i) a first channel having a first proximal end, a first distal end, a first depth, and a first width, the first channel comprising particles and a first liquid; and ii) a droplet formation region in fluid communication with the first channel; and iii) a collection region configured to collect droplets formed in the droplet formation region and containing the second liquid; and b) allowing the first liquid to flow from the first channel to the droplet formation region to produce droplets of the first liquid and particles in the second liquid.

The droplet formation region may be configured to allow the first liquid to expand in at least one dimension. The first liquid may be substantially immiscible with the second liquid. The device may be capable of forming droplets without externally driving the second liquid.

In some embodiments, the droplets are substantially stationary in the collection region.

In further embodiments, the first depth decreases in the proximal-to-distal direction in at least a portion of the first channel. In yet further embodiments, the first depth increases in the proximal-to-distal direction in at least a portion of the first channel. In still further embodiments, the first channel further comprises a groove.

In certain embodiments, the device further includes a first reservoir in fluid communication with the first proximal end. In particular embodiments, the first reservoir further contains the particles.

In some embodiments, step b) produces droplets having a single particle or a single particle of multiple types, e.g., one bead and one cell.

In other embodiments, the particles have about the same density as the first liquid. In yet other embodiments, the density of the first liquid is lower than the density of the second liquid. In still other embodiments, the density of the first liquid is higher than the density of the second liquid.

In particular embodiments, the first liquid is aqueous or miscible with water.

In some embodiments, the device further includes a second channel having a second proximal end, a second distal end, a second depth, and a second width. The second channel may intersect the first channel between the first proximal end and the first distal end. The second channel may include a third liquid. The third liquid may combine with the first liquid at the intersection, and the droplets may further contain the third liquid.

In further embodiments, the second depth decreases in the proximal-to-distal direction in at least a portion of the second channel. In yet further embodiments, the second depth increases in the proximal-to-distal direction in at least a portion of the second channel.

In still further embodiments, the third liquid is aqueous or miscible with water. In some embodiments, the density of the third liquid is lower than the density of the second liquid. In certain embodiments, the density of the third liquid is higher than the density of the second liquid.

In particular embodiments, the device further includes a second reservoir in fluid communication with the second proximal end.

In some embodiments, the second channel further includes a groove. In certain embodiments, the droplet formation region comprises a shelf region having a third depth and a third width. The shelf region has at least one inlet and at least one outlet.

In certain embodiments, the third width increases from the inlet of the shelf region to the outlet of the shelf region.

In particular embodiments, the droplet formation region includes a step region having a fourth depth.

In some embodiments, the droplet formation region further includes a shelf region that is disposed between the first distal end and the step region.

In certain embodiments, the device further includes a third channel having a third proximal end and a third distal end. The third proximal end may be in fluid communication with the shelf region. The third distal end may be in fluid communication with the step region.

In further embodiments, the droplet formation region includes a plurality of inlets in fluid communication with the first proximal end and a plurality of outlets. In yet further embodiments, the number of inlets and the number of outlets is the same.

In another aspect, the invention features a method of producing an analyte detection droplet. The method includes providing a device having a plurality of particles in a liquid carrier, wherein the particles include an analyte detection moiety. The device also includes a sample liquid having an analyte, a particle channel, a sample channel that intersects with the particle channel at an intersection, a droplet formation region distal to the particle channel and the sample channel, and a droplet collection region. The droplet formation region is configured to allow the liquid carrier to expand in at least one dimension and can include a step. Particles in the liquid carrier flow proximal-to-distal through the particle channel, and the sample liquid is allowed to flow proximal-to-distal through the sample channel. The sample liquid combines with the particles in the liquid carrier to form an analyte detection liquid at the intersection, and the analyte detection liquid meets a partitioning liquid at the droplet formation region under droplet forming conditions to form a plurality of analyte detection droplets. The plurality of analyte detection droplets includes one or more of the particles in the analyte detection liquid (e.g., one or more of the plurality of analyte detection droplets includes one or more particles).

In some embodiments, the particle channel is one of a plurality of particle channels and the sample channel is one of a plurality of sample channels. The device can further include a particle reservoir connected proximally to the plurality of particle channels and a sample reservoir connected proximally to the plurality of sample channels.

In some embodiments, the sample liquid and the liquid carrier are miscible. In some embodiments, the sample liquid and the liquid carrier are aqueous liquids and the partitioning liquid is immiscible with the sample liquid and the liquid carrier. The analyte can be a bioanalyte, for example, a nucleic acid, an intracellular protein, a glycan, or a surface protein. The analyte detection moiety can include a nucleic acid or an antigen-binding protein. The sample can include a cell, or a component or product thereof. In some embodiments, the plurality of analyte detection droplets accumulates as a population (e.g., a substantially stationary population) in the droplet collection region.

In another aspect, the invention provides a method of producing a bioanalyte detection droplet by providing a device having a plurality of particles in an aqueous carrier, a particle channel, a droplet formation region, and a droplet collection region. The particles can include a bioanalyte detection moiety, the droplet formation region is configured to allow the aqueous carrier to expand in at least one dimension, the particle channel is proximal to the droplet formation region, and the droplet formation region is proximal to the droplet collection region. The method further includes allowing the particles in the aqueous carrier to flow proximal-to-distal through the particle channel and droplet formation region. The aqueous carrier meets a partitioning liquid at the droplet formation region under droplet forming conditions, thereby forming a plurality of bioanalyte detection droplets. The plurality of bioanalyte detection droplets includes one or more of the particles in the aqueous carrier (e.g., one or more of the plurality of bioanalyte detection droplets includes one or more particles), and the plurality of bioanalyte detection droplets accumulate in the droplet collection region. In some embodiments, the device further includes a sample channel that intersects with the particle channel proximal to the droplet formation region at an intersection. The aqueous sample including a bioanalyte flows proximal-to-distal through the sample channel and combines with particles in the aqueous carrier at the intersection. The plurality of bioanalyte detection droplets includes the aqueous sample and one or more particles in the aqueous carrier. For example, one or more of each of the plurality of bioanalyte detection droplets includes one or more particles. Devices of this aspect of the invention can include any one or more features of any of the devices from any of the preceding aspects.

In some embodiments, the droplet formation region includes a step. In some embodiments, the particle channel is one of a plurality of particle channels and the sample channel is one of a plurality of sample channels. In some embodiments, the device further includes a particle reservoir connected proximally to the plurality of particle channels and a sample reservoir connected proximally to the plurality of sample channels.

The bioanalyte detection moiety can include a nucleic acid and/or a barcode. In some embodiments, the bioanalyte is selected from the group consisting of a surface-expressed protein, an intracellular protein, a glycan, and a nucleic acid.

In some embodiments, the aqueous sample includes a cell, or a component or product thereof. In some embodiments, the aqueous carrier includes one or more enzymes and/or lysis agents.

The method can further include, after the bioanalyte detection droplets are formed, incubating the droplets under conditions sufficient to allow the bioanalyte detection moiety to label the bioanalyte. In some embodiments, the bioanalyte is a nucleic acid, and after labeling the bioanalyte, incubating the reaction droplets under conditions sufficient to amplify the barcoded nucleic acids. In some embodiments, the aqueous carrier includes one or more enzymes, such as reverse transcriptase.

In some embodiments, the particle channel is one of a plurality of particle channels and the sample channel is one of a plurality of sample channels, and the device further includes a particle reservoir connected proximally to the plurality of particle channels and a sample reservoir connected proximally to the plurality of sample channels.

In yet another aspect, the invention features a method of barcoding a population of cells by providing a device having a plurality of particles in an aqueous carrier, an aqueous sample having a population of cells, a particle channel, a sample channel, a droplet formation region (e.g., a droplet formation region including a step), and a droplet collection region. The particles can include a nucleic acid primer sequence and a barcode, and the droplet formation region is configured to allow the aqueous carrier to expand in at least one dimension. The particle channel intersects the sample channel at an intersection proximal to the droplet formation region, and the droplet formation region is proximal to the droplet collection region. The particles in the aqueous carrier flow proximal-to-distal through the particle channel, and the aqueous sample is allowed to flow proximal-to-distal through the sample channel. The aqueous sample combines with the particles in the aqueous carrier to form a reaction liquid at the intersection, and the reaction liquid meets a partitioning liquid at the droplet formation region under droplet forming conditions to form a plurality of reaction droplets. The plurality of reaction droplets includes one or more of the particles in the reaction liquid (e.g., one or more of the plurality of reaction droplets includes one or more particles). The plurality of reaction droplets accumulates in the droplet collection region, and the reaction droplets are incubated under conditions sufficient to allow for barcoding nucleic acids in the population of cells.

In some embodiments, the particle channel is one of a plurality of particle channels and the sample channel is one of a plurality of sample channels, and the device further includes a particle reservoir connected proximally to the plurality of particle channels and a sample reservoir connected proximally to the plurality of sample channels. Devices of this aspect of the invention can include any one or more features of any of the devices from any of the preceding aspects.

In some embodiments, the aqueous carrier includes a lysis reagent configured to lyse the cells before or during the incubation of the reaction droplets. The aqueous carrier or the aqueous sample can include one or more enzymes, such as reverse transcriptase.

In another embodiment, the invention provides a method of single-cell nucleic acid sequencing. The method includes providing a device having a plurality of particles in an aqueous carrier, an aqueous sample having a population of cells, a particle channel, a sample channel, a droplet formation region (e.g., a droplet formation region including a step), and a droplet collection region. The particles include a nucleic acid primer sequence and a barcode, and the droplet formation region is configured to allow the aqueous carrier to expand in at least one dimension. The particle channel intersects the sample channel at an intersection proximal to the droplet formation region, and the droplet formation region is proximal to the droplet collection region. The particles in the aqueous carrier flow proximal-to-distal through the particle channel, and the aqueous sample is allowed to flow proximal-to-distal through the sample channel. The aqueous sample combines with the particles in the liquid carrier to form a reaction liquid at the intersection, and the reaction liquid meets a partitioning liquid at the droplet formation region under droplet forming conditions to form a plurality of reaction droplets. The plurality of reaction droplets includes one or more of the particles and a single cell or lysate thereof (e.g., one or more of the plurality of reaction droplets includes one or more particles and a single cell or lysate thereof). In some embodiments, one or more (e.g., at least 1%, 5%, 10%, 15%, 20%, 25%, 30%, 35%, 40%, 45%, 50%, 55%, 60%, 65%, 70%, 75%, 80%, 85% 90%, 91%, 92%, 93%, 94%, 95%, 96%, 97%, 98%, 99%, 100%) of the reaction droplets includes a single particle and a single cell. The plurality of droplets accumulates in the droplet collection region. The reaction droplets are incubated under conditions sufficient to generate barcoded nucleic acids, and the barcoded nucleic acid transcripts are sequenced to obtain nucleic acid sequences associated with single cells. Devices of this aspect of the invention can include any one or more features of any of the devices from any of the preceding aspects.

In some embodiments, the aqueous carrier includes a lysis reagent configured to lyse the cells before or during incubation of the reaction droplets. The aqueous carrier or the aqueous sample can include one or more enzymes, such as reverse transcriptase. In some embodiments, the method further includes compiling the nucleic acid sequences associated with single cells into a genome library.

In yet another aspect, the invention provides a device for producing droplets of a first fluid in a second fluid.

In one embodiment, the device includes a) a first channel having a first depth, a first width, a first proximal end, and a first distal end; and b) a droplet formation region in fluid communication with, e.g., fluidically connected to, the first distal end, wherein the droplet formation region comprises a shelf region having a second depth and a second width and a step region having a third depth, wherein the second width is greater than the first width and increases from the first distal end towards the step region, the third depth is greater than the first depth, and the shelf region is disposed between the first distal end and the step region. The first channel and droplet formation region are configured to produce droplets of the first fluid in the second fluid, e.g., as a result of the first fluid flowing from the first distal end to the step region.

In another embodiment, the device includes a) a first channel having a first depth, a first width, a first proximal end, and a first distal end; b) a second channel having a fourth depth, a fourth width, a fourth proximal end, and a fourth distal end, wherein the second channel intersects the first channel between the first proximal and first distal ends; and c) a droplet formation region in fluid communication with, e.g., fluidically connected to, the first distal end, wherein the droplet formation region comprises a shelf region having a second depth and a second width and a step region having a third depth, wherein the second width is greater than the first width, the third depth is greater than the first depth, and the shelf region is disposed between the first distal end and the step region. The first channel and droplet formation region are configured to produce droplets of the first fluid in the second fluid, e.g., as a result of the first fluid flowing from the first distal end to the step region.

In a further embodiment, the device includes a) a first channel having a first depth, a first width, a first proximal end, and a first distal end; b) a droplet formation region fluidically connected to the first distal end, wherein the droplet formation region comprises a shelf region having a second depth and a second width and a step region having a third depth, wherein the second width is greater than the first width, the third depth is greater than the first depth, and the shelf region is disposed between the first distal end and the step region; and c) a third channel having an outlet into the shelf region between the first distal end and the step region. The first channel and droplet formation region are configured to produce droplets of the first fluid in the second fluid, e.g., as a result of the first fluid flowing from the first distal end to the step region.

In various embodiments of the devices of the invention, the first fluid includes particles, such as gel beads. In these embodiments, the first channel and the droplet formation region may be configured to produce droplets including a single particle or a single particle of multiple types, e.g., one bead and one cell. In other embodiments, the first channel further includes a groove. In other embodiments, the device further includes a first reservoir to which the first proximal end is fluidically connected; a second reservoir to which the shelf region is in fluid communication with, e.g., fluidically connected to; and/or a third reservoir to which the step region is in fluid communication with, e.g., fluidically connected to. In some embodiments, the first depth and the second depth are the same. In further embodiments, the first depth is greater than the second depth.

In embodiments of certain devices, the devices further include a second channel having a fourth depth, a fourth width, a fourth proximal end, and a fourth distal end, wherein the second channel intersects the first channel between the first proximal and first distal ends. In these embodiments, the device may also include a fourth reservoir to which the fourth proximal end is fluidically connected.

In embodiments of certain devices, the devices further include a third channel having an outlet to the shelf region between the first distal end and the step region.

Devices of the invention may also include a controller operatively coupled to the first channel to transport the first fluid out of the first distal end.

In certain embodiments, the first channel further includes a plurality of distal ends each fluidically connected to the droplet formation region.

In further embodiments, the second depth is substantially constant. In other embodiments, the second depth increases from the first distal end towards the step region. In further embodiments, the third depth is substantially constant. In other embodiments, the third depth increases away from the shelf region.

In devices of the invention, the step region may increase in depth upward from the shelf region, downward from the shelf region, or both.

In further embodiments, the second width is greater than the first width and increases from the first distal end towards the step region. The second width may increase linearly or non-linearly.

In other embodiments, the shelf region or step region further includes a surface coating.

In yet other embodiments, the first channel and the shelf region are combined to form a merged channel that increases in width from the first proximal end towards the step region.

In another aspect, the invention provides a method of forming a droplet of a first fluid in a second fluid. In one embodiment, the method includes transporting a first fluid, e.g., one including particles, through a channel into a second fluid that is stationary under conditions that droplets form.

In other embodiments, the method includes providing a device of the invention and flowing the first fluid through the first channel to the step region, thereby forming the droplet of the first fluid.

In further embodiments, the method includes transporting the first fluid through a channel having a change in width along its length so that a droplet forms as the first fluid passes along the channel into the second fluid, wherein the droplet comprises a particle.

In embodiments of the methods of the invention, the channel is a first channel having a first depth, a first width, a first proximal end, and a first distal end and disposed in a device; and the device further includes a droplet formation region fluidically connected to the first distal end, wherein the droplet formation region includes a shelf region having a second depth and a second width and a step region having a third depth, wherein the second width is greater than the first width, the third depth is greater than the first depth, and the shelf region is disposed between the first distal end and the step region.

In certain embodiments, the first fluid and second fluid are immiscible. The first fluid may be aqueous, and/or the second fluid includes an oil. The first fluid may include particles, e.g., gel beads. In certain embodiments, the first channel and the droplet formation region are configured to produce droplets including a single particle or a single particle of multiple types, e.g., one bead and one cell. The diameter of the gel beads may be substantially similar to the dimensions of the first channel. In other embodiments, the diameter of the gel beads is substantially larger than the dimensions of the first channel.

It will be understood that the devices, systems, kits, and methods described herein may, in addition to features specified, include any feature described herein that is not inconsistent with the structure of the underlying device, system, kit, or method. Thus, devices may include multiple drop formation regions, either in communication with each other or not in fluid communication with either other, differential surface features, or additional elements or steps as described herein.

Definitions

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The terms "adaptor(s)", "adapter(s)" and "tag(s)" may be used synonymously. An adaptor or tag can be coupled to a polynucleotide sequence to be "tagged" by any approach including ligation, hybridization, or other approaches.

The term "barcode," as used herein, generally refers to a label, or identifier, that conveys or is capable of conveying information about an analyte. A barcode can be part of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads in real time.

The term "bead," as used herein, generally refers to a generally spherical or ellipsoid particle that is not a biological particle. The bead may be a solid or semi-solid particle. The bead may be a gel bead (e.g., a hydrogel bead). The bead may be formed of a polymeric material. The bead may be magnetic or non-magnetic.

The term "biological particle," as used herein, generally refers to a discrete biological system derived from a biological sample, such as a cell or a particulate component of a cell, such as an organelle, exosome, or vesicle. The biological particle may be a rare cell from a population of cells. The biological particle may be any type of cell, including without limitation prokaryotic cells, eukaryotic cells, bacterial, fungal, plant, mammalian, or other animal cell types, mycoplasmas, normal tissue cells, tumor cells, or any other cell type, whether derived from single cell or multicellular organisms. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix. Alternatively, the biological particle may be a virus.

The term "fluidically connected", as used herein, refers to a direct connection between at least two device elements, e.g., a channel, reservoir, etc., that allows for fluid to move between such device elements without passing through an intervening element.

The term "genome," as used herein, generally refers to genomic information from a subject, which may be, for example, at least a portion or an entirety of a subject's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together may constitute a human genome.

The term "in fluid communication with", as used herein, refers to a connection between at least two device elements, e.g., a channel, reservoir, etc., that allows for fluid to move between such device elements with or without passing through one or more intervening device elements.

The term "macromolecular constituent," as used herein, generally refers to a macromolecule contained within a biological particle. The macromolecular constituent may comprise a nucleic acid. The macromolecular constituent may comprise deoxyribonucleic acid (DNA). The macromolecular constituent may comprise ribonucleic acid (RNA). The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise an oligonucleotide or polypeptide sequence. The molecular tag may comprise a DNA aptamer. The molecular tag may be or comprise a primer. The molecular tag may be or comprise a protein. The molecular tag may comprise a polypeptide. The molecular tag may be a barcode.

The term "oil," as used herein, generally refers to a liquid that is not miscible with water. An oil may have a density higher or lower than water and/or a viscosity higher or lower than water.

The term "sample," as used herein, generally refers to a biological sample of a subject. The biological sample may be a nucleic acid sample or protein sample. The biological sample may be derived from another sample. The sample may be a tissue sample, such as a biopsy, core biopsy, needle aspirate, or fine needle aspirate. The sample may be a liquid sample, such as a blood sample, urine sample, or saliva sample. The sample may be a skin sample. The sample may be a cheek swap. The sample may be a plasma or serum sample. The sample may include a biological particle, e.g., a cell or virus, or a population thereof, or it may alternatively be free of biological particles. A cell-free sample may include polynucleotides. Polynucleotides may be isolated from a bodily sample that may be selected from the group consisting of blood, plasma, serum, urine, saliva, mucosal excretions, sputum, stool and tears.

The term "sequencing," as used herein, generally refers to methods and technologies for determining the sequence of nucleotide bases in one or more polynucleotides. The polynucleotides can be, for example, deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina, Pacific Biosciences, Oxford Nanopore, or Life Technologies (Ion Torrent). As an alternative, sequencing may be performed using nucleic acid amplification, polymerase chain reaction (PCR) (e.g., digital PCR, quantitative PCR, or real time PCR) or isothermal amplification. Such devices may provide a plurality of raw genetic data corresponding to the genetic information of a subject (e.g., human), as generated by the device from a sample provided by the subject. In some situations, systems and methods provided herein may be used with proteomic information.

The term "subject," as used herein, generally refers to an animal, such as a mammal (e.g., human) or avian (e.g., bird), or other organism, such as a plant. The subject can be a vertebrate, a mammal, a mouse, a primate, a simian or a human. Animals may include, but are not limited to, farm animals, sport animals, and pets. A subject can be a healthy or asymptomatic individual, an individual that has or is suspected of having a disease (e.g., cancer) or a predisposition to the disease, or an individual that is in need of therapy or suspected of needing therapy. A subject can be a patient.

The term "substantially stationary", as used herein with respect to droplet formation, generally refers to a state when motion of formed droplets in the continuous phase is passive, e.g., resulting from the difference in density between the dispersed phase and the continuous phase.

BRIEF DESCRIPTION OF THE DRAWINGS

FIGS. 6A-6B show a cross-section view and a top view, respectively, of another example of a microfluidic device with a geometric feature for droplet formation.

FIGS. 7A-7B show a cross-section view and a top view, respectively, of another example of a microfluidic device with a geometric feature for droplet formation.

FIGS. 8A-8B show a cross-section view and a top view, respectively, of another example of a microfluidic device with a geometric feature for droplet formation.

FIG. 9A is top view of a device of the invention with reservoirs. FIG. 9B is a micrograph of a first channel intersected by a second channel adjacent a droplet formation region.

FIG. 13A is an overview of a device with four droplet formation regions. FIG. 13B is a zoomed in view of an exemplary droplet formation region within the dotted line box in FIG. 13A.

FIG. 14A shows a device with three reservoirs employed in droplet formation. FIG. 14B is a device of the invention with four reservoirs employed in the droplet formation.

FIG. 16A is a top view of a device having two liquid channels that meet adjacent to a droplet formation region. FIG. 16B is a zoomed in view of the droplet formation region showing the individual droplet formations regions.

FIG. 17A is an overview of the method, and FIG. 17B is a micrograph showing the use of a blocking fluid to protect a channel from a coating agent.

DETAILED DESCRIPTION OF THE INVENTION

Figure 1:
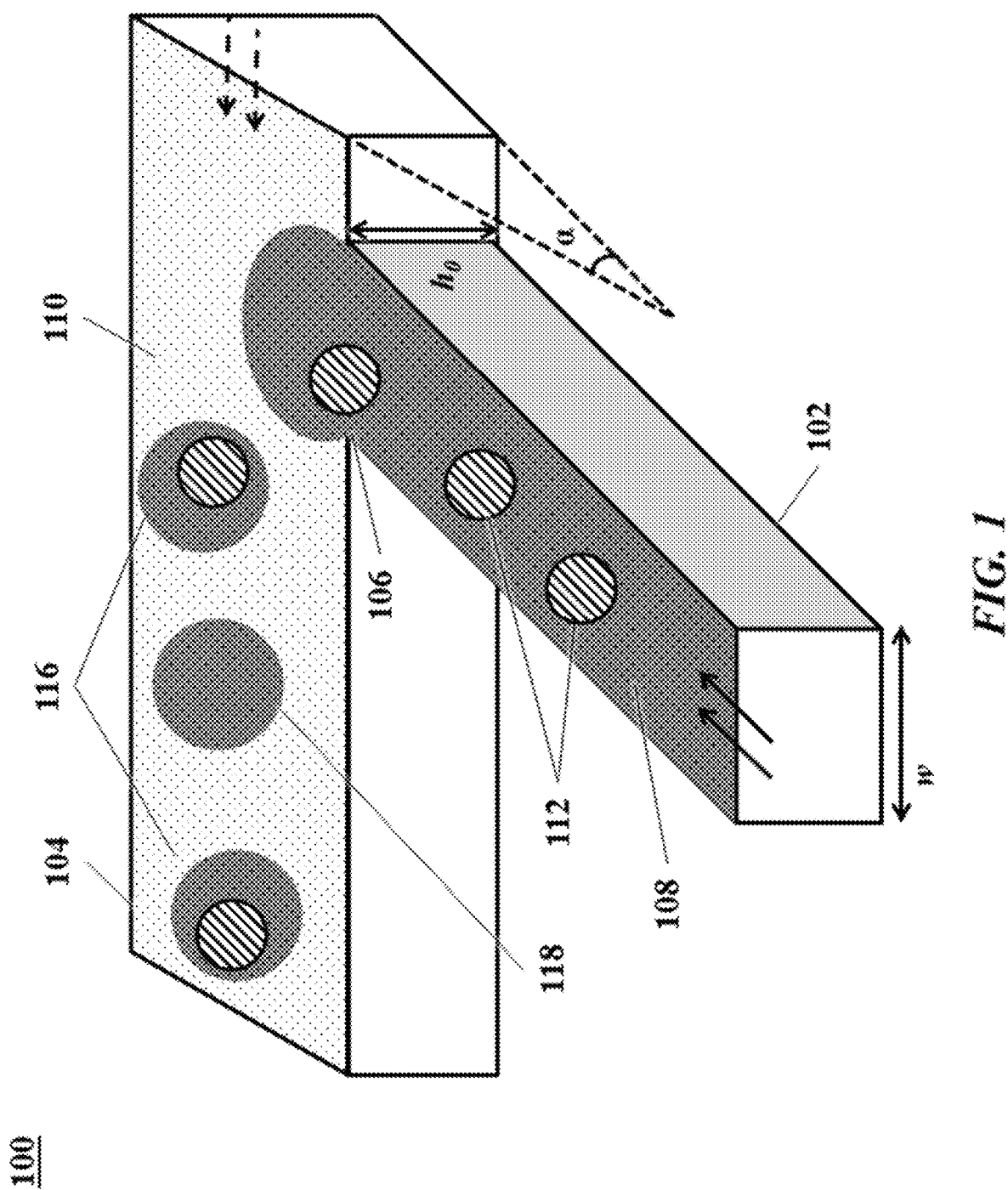
FIG. 1 shows an example of a microfluidic device for the introduction of particles, e.g., beads, into discrete droplets.

The invention provides devices, kits, and systems for forming droplets and methods of their use. The devices may be used to form droplets of a size suitable for utilization as microscale chemical reactors, e.g., for genetic sequencing. In general, droplets are formed in a device by flowing a first liquid through a channel and into a droplet formation region including a second liquid, i.e., the continuous phase, which may or may not be externally driven. Thus, droplets can be formed without the need for externally driving the second liquid.

In the present invention, the size of the generated droplets is significantly less sensitive to changes in liquid properties. For example, the size of the generated droplets is less sensitive to the dispersed phase flow rate. Adding multiple formation regions is also significantly easier from a layout and manufacturing standpoint. The addition of further formation regions allows for formation of droplets even in the event that one droplet formation region becomes blocked. Droplet formation can be controlled by adjusting one or more geometric features of fluidic channel architecture, such as a width, height, and/or expansion angle of one or more fluidic channels. For example, droplet size and speed of droplet formation may be controlled. In some instances, the number of regions of formation at a driven pressure can be increased to increase the throughput of droplet formation.

Devices

A device of the invention includes a first channel having a depth, a width, a proximal end, and a distal end. The proximal end is or is configured to be in fluid communication with a source of liquid, e.g., a reservoir integral to the device or coupled to the device, e.g., by tubing. The distal end is in fluid communication with, e.g., fluidically connected to, a droplet formation region. A droplet formation region allows liquid from the first channel to expand in at least one dimension, leading to droplet formation under appropriate conditions as described herein. A droplet formation region can be of any suitable geometry. In one embodiment, the droplet formation region includes a shelf region that allows liquid to expand substantially in one dimension, e.g., perpendicular to the direction of flow. The width of the shelf region is greater than the width of the first channel at its distal end. In certain embodiments, the first channel is a channel distinct from a shelf region, e.g., the shelf region widens or widens at a steeper slope or curvature than the distal end of the first channel. In other embodiments, the first channel and shelf region are merged into a continuous flow path, e.g., one that widens linearly or non-linearly from its proximal end to its distal end; in these embodiments, the distal end of the first channel can be considered to be an arbitrary point along the merged first channel and shelf region. In another embodiment, the droplet formation region includes a step region, which provides a spatial displacement and allows the liquid to expand in more than one dimension. The spatial displacement may be upward or downward or both relative to the channel. The choice of direction may be made based on the relative density of the dispersed and continuous phases, with an upward step employed when the dispersed phase is less dense than the continuous phase and a downward step employed when the dispersed phase is denser than the continuous phase. Droplet formation regions may also include combinations of a shelf and a step region, e.g., with the shelf region disposed between the channel and the step region.

Without wishing to be bound by theory, droplets of a first liquid can be formed in a second liquid in the devices of the invention by flow of the first liquid from the distal end into the droplet formation region. In embodiments with a shelf region and a step region, the stream of first liquid expands laterally into a disk-like shape in the shelf region. As the stream of first liquid continues to flow across the shelf region, the stream passes into the step region wherein the droplet assumes a more spherical shape and eventually detaches from the liquid stream. As the droplet is forming, passive flow of the continuous phase around the nascent droplet occurs, e.g., into the shelf region, where it reforms the continuous phase as the droplet separates from its liquid stream. Droplet formation by this mechanism can occur without externally driving the continuous phase, unlike in other systems. It will be understood that the continuous phase may be externally driven during droplet formation, e.g., by gently stirring or vibration but such motion is not necessary for droplet formation.

Passive flow of the continuous phase may occur simply around the nascent droplet. The droplet formation region may also include one or more channels that allow for flow of the continuous phase to a location between the distal end of the first channel and the bulk of the nascent droplet. These channels allow for the continuous phase to flow behind a nascent droplet, which modifies (e.g., increase or decreases) the rate of droplet formation. Such channels may be fluidically connected to a reservoir of the droplet formation region or to different reservoirs of the continuous phase. Although externally driving the continuous phase is not necessary, external driving may be employed, e.g., to pump continuous phase into the droplet formation region via additional channels. Such additional channels may be to one or both lateral sides of the nascent droplet or above or below the plane of the nascent droplet.

In general, the components of a device, e.g., channels, may have certain geometric features that at least partly determine the sizes of the droplets. For example, any of the channels described herein have a depth, a height, $h_0$, and width, w. The droplet formation region may have an expansion angle, $\alpha$. Droplet size may decrease with increasing expansion angle. The resulting droplet radius, $R_d$, may be predicted by the following equation for the aforementioned geometric parameters of $h_0$, w, and $\alpha$:

$$R_d \approx 0.44\left(1 + 2.2\sqrt{\tan\alpha}\,\frac{w}{h_0}\right)\frac{h_0}{\sqrt{\tan\alpha}}$$

As a non-limiting example, for a channel with w=21 µm, h=21 µm, and $\alpha$=3°, the predicted droplet size is 121 µm. In another example, for a channel with w=25 µm, h=25 µm, and $\alpha$=5°, the predicted droplet size is 123 µm. In yet another example, for a channel with w=28 µm, h=28 µm, and $\alpha$=7°, the predicted droplet size is 124 µm. In some instances, the expansion angle may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

The depth and width of the first channel may be the same, or one may be larger than the other, e.g., the width is larger than the depth, or first depth is larger than the width. In some embodiments, the depth and/or width is between about 0.1 µm and 1000 µm. In some embodiments, the depth and/or width of the first channel is from 1 to 750 µm, 1 to 500 µm, 1 to 250 µm, 1 to 100 µm, 1 to 50 µm, or 3 to 40 µm. In some cases, when the width and length differ, the ratio of the width to depth is, e.g., from 0.1 to 10, e.g., 0.5 to 2 or greater than 3, such as 3 to 10, 3 to 7, or 3 to 5. The width and depths of the first channel may or may not be constant over its length. In particular, the width may increase or decrease adjacent the distal end. In general, channels may be of any suitable cross section, such as a rectangular, triangular, or circular, or a combination thereof. In particular embodiments, a channel may include a groove along the bottom surface. The width or depth of the channel may also increase or decrease, e.g., in discrete portions, to alter the rate of flow of liquid or particles or the alignment of particles.

Devices of the invention may also include additional channels that intersect the first channel between its proximal and distal ends, e.g., one or more second channels having a second depth, a second width, a second proximal end, and a second distal end. Each of the first proximal end and second proximal ends are or are configured to be in fluid communication with, e.g., fluidically connected to, a source of liquid, e.g., a reservoir integral to the device or coupled to the device, e.g., by tubing. The inclusion of one or more intersection channels allows for splitting liquid from the first channel or introduction of liquids into the first channel, e.g., that combine with the liquid in the first channel or do not combine with the liquid in the first channel, e.g., to form a sheath flow. Channels can intersect the first channel at any suitable angle, e.g., between 5° and 135° relative to the centerline of the first channel, such as between 75° and 115° or 85° and 95°. Additional channels may similarly be present to allow introduction of further liquids or additional flows of the same liquid. Multiple channels can intersect the first channel on the same side or different sides of the first channel. When multiple channels intersect on different sides, the channels may intersect along the length of the first channel to allow liquid introduction at the same point. Alternatively, channels may intersect at different points along the length of the first channel. In some instances, a channel configured to direct a liquid comprising a plurality of particles may comprise one or more grooves in one or more surface of the channel to direct the plurality of particles towards the droplet formation fluidic connection. For example, such guidance may increase single occupancy rates of the generated droplets. These additional channels may have any of the structural features discussed above for the first channel.

Devices may include multiple first channels, e.g., to increase the rate of droplet formation. In general, throughput may significantly increase by increasing the number of droplet formation regions of a device. For example, a device having five droplet formation regions may generate five times as many droplets than a device having one droplet formation region, provided that the liquid flow rate is substantially the same. A device may have as many droplet formation regions as is practical and allowed for the size of the source of liquid, e.g., reservoir. For example, the device may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 2000 or more droplet formation regions. Inclusion of multiple droplet formation regions may require the inclusion of channels that traverse but do not intersect, e.g., the flow path is in a different plane. Multiple first channel may be in fluid communication with, e.g., fluidically connected to, a separate source reservoir and/or a separate droplet formation region. In other embodiments, two or more first channels are in fluid communication with, e.g., fluidically connected to, the same fluid source, e.g., where the multiple first channels branch from a single, upstream channel. The droplet formation region may include a plurality of inlets in fluid communication with the first proximal end and a plurality of outlets (e.g., plurality of outlets in fluid communication with a collection region). The number of inlets and the number of outlets in the droplet formation region may be the same (e.g., there may be 3-10 inlets and/or 3-10 outlets). Alternatively or in addition, the throughput of droplet formation can be increased by increasing the flow rate of the first liquid. In some cases, the throughput of droplet formation can be increased by having a plurality of single droplet forming devices, e.g., devices with a first channel and a droplet formation region, in a single device, e.g., parallel droplet formation.

The width of a shelf region may be from 0.1 μm to 1000 μm. In particular embodiments, the width of the shelf is from 1 to 750 μm, 10 to 500 μm, 10 to 250 μm, or 10 to 150 μm. The width of the shelf region may be constant along its length, e.g., forming a rectangular shape. Alternatively, the width of the shelf region may increase along its length away from the distal end of the first channel. This increase may be linear, nonlinear, or a combination thereof. In certain embodiments, the shelf widens 5% to 10,000%, e.g., at least 300%, (e.g., 10% to 500%, 100% to 750%, 300% to 1000%, or 500% to 1000%) relative to the width of the distal end of the first channel. The depth of the shelf can be the same as or different from the first channel. For example, the bottom of the first channel at its distal end and the bottom of the shelf region may be coplanar. Alternatively, a step or ramp may be present where the distal end meets the shelf region. The depth of the distal end may also be greater than the shelf region, such that the first channel forms a notch in the shelf region. The depth of the shelf may be from 0.1 to 1000 μm, e.g., 1 to 750 μm, 1 to 500 μm, 1 to 250 μm, 1 to 100 μm, 1 to 50 μm, or 3 to 40 μm. In some embodiments, the depth is substantially constant along the length of the shelf. Alternatively, the depth of the shelf slopes, e.g., downward or upward, from the distal end of the liquid channel to the step region. The final depth of the sloped shelf may be, for example, from 5% to 1000% greater than the shortest depth, e.g., 10 to 750%, 10 to 500%, 50 to 500%, 60 to 250%, 70 to 200%, or 100 to 150%. The overall length of the shelf region may be from at least about 0.1 μm to about 1000 μm, e.g., 0.1 to 750 μm, 0.1 to 500 μm, 0.1 to 250 μm, 0.1 to 150 μm, 1 to 150 μm, 10 to 150 μm, 50 to 150 μm, 100 to 150 μm, 10 to 80 μm, or 10 to 50 μm. In certain embodiments, the lateral walls of the shelf region, i.e., those defining the width, may be not parallel to one another. In other embodiments, the walls of the shelf region may narrower from the distal end of the first channel towards the step region. For example, the width of the shelf region adjacent the distal end of the first channel may be sufficiently large to support droplet formation. In other embodiments, the shelf region is not substantially rectangular, e.g., not rectangular or not rectangular with rounded or chamfered corners.

A step region includes a spatial displacement (e.g., depth). Typically, this displacement occurs at an angle of approximately 90°, e.g., between 85° and 95°. Other angles are possible, e.g., 10-90°, e.g., 20 to 90°, 45 to 90°, or 70 to 90°. The spatial displacement of the step region may be any suitable size to be accommodated on a device, as the ultimate extent of displacement does not affect performance of the device. Preferably the displacement is several times the diameter of the droplet being formed. In certain embodiments, the displacement is from about 1 μm to about 10 cm, e.g., at least 10 μm, at least 40 μm, at least 100 μm, or at least 500 μm, e.g., 40 μm to 600 μm. In some cases, the depth of the step region is substantially constant. Alternatively, the depth of the step region may increase away from the shelf region, e.g., to allow droplets that sink or float to roll away from the spatial displacement as they are formed. The step region may also increase in depth in two dimensions relative to the shelf region, e.g., both above and below the plane of the shelf region. The reservoir may have an inlet and/or an outlet for the addition of continuous phase, flow of continuous phase, or removal of the continuous phase and/or droplets.

While dimension of the devices may be described as width or depths, the channels, shelf regions, and step regions may be disposed in any plane. For example, the width of the shelf may be in the x-y plane, the x-z plane, the y-z plane or any plane therebetween. In addition, a droplet formation region, e.g., including a shelf region, may be laterally spaced in the x-y plane relative to the first channel or located above or below the first channel. Similarly, a droplet formation region, e.g., including a step region, may be laterally spaced in the x-y plane, e.g., relative to a shelf region or located above or below a shelf region. The spatial displacement in a step region may be oriented in any plane suitable to allow the nascent droplet to form a spherical shape. The fluidic components may also be in different planes so long as connectivity and other dimensional requirements are met.

The device may also include reservoirs for liquid reagents. For example, the device may include a reservoir for the liquid to flow in the first channel and/or a reservoir for the liquid into which droplets are formed. In some cases, devices of the invention include a collection region, e.g., a volume for collecting formed droplets. A droplet collection region may be a reservoir that houses continuous phase or can be any other suitable structure, e.g., a channel, a shelf, a chamber, or a cavity, on or in the device. For reservoirs or other elements used in collection, the walls may be smooth and not include an orthogonal element that would impede droplet movement. For example, the walls may not include any feature that at least in part protrudes or recedes from the surface. It will be understood, however, that such elements may have a ceiling or floor. The droplets that are formed may be moved out of the path of the next droplet being formed by gravity (either upward or downward depending on the relative density of the droplet and continuous phase). Alternatively or in addition, formed droplets may be moved out of the path of the next droplet being formed by an external force applied to the liquid in the collection region, e.g., gentle stirring, flowing continuous phase, or vibration. Similarly, a reservoir for liquids to flow in additional channels, such as those intersecting the first channel may be present. A single reservoir may also be connected to multiple channels in a device, e.g., when the same liquid is to be introduced at two or more different locations in the device. Waste reservoirs or overflow reservoirs may also be included to collect waste or overflow when droplets are formed. Alternatively, the device may be configured to mate with sources of the liquids, which may be external reservoirs such as vials, tubes, or pouches. Similarly, the device may be configured to mate with a separate component that houses the reservoirs. Reservoirs may be of any appropriate size, e.g., to hold 10 μL to 500 mL, e.g., 10 μL to 300 mL, 25 μL to 10 mL, 100 μL to 1 mL, 40 μL to 300 μL, 1 mL to 10 mL, or 10 mL to 50 mL. When multiple reservoirs are present, each reservoir may have the same or a different size.

In addition to the components discussed above, devices of the invention can include additional components. For example, channels may include filters to prevent introduction of debris into the device. In some cases, the microfluidic systems described herein may comprise one or more liquid flow units to direct the flow of one or more liquids, such as the aqueous liquid and/or the second liquid immiscible with the aqueous liquid. In some instances, the liquid flow unit may comprise a compressor to provide positive pressure at an upstream location to direct the liquid from the upstream location to flow to a downstream location. In some instances, the liquid flow unit may comprise a pump to provide negative pressure at a downstream location to direct the liquid from an upstream location to flow to the downstream location. In some instances, the liquid flow unit may comprise both a compressor and a pump, each at different locations. In some instances, the liquid flow unit may comprise different devices at different locations. The liquid flow unit may comprise an actuator. In some instances, where the second liquid is substantially stationary, the reservoir may maintain a constant pressure field at or near each droplet formation region. Devices may also include various valves to control the flow of liquids along a channel or to allow introduction or removal of liquids or droplets from the device. Suitable valves are known in the art. Valves useful for a device of the present invention include diaphragm valves, solenoid valves, pinch valves, or a combination thereof. Valves can be controlled manually, electrically, magnetically, hydraulically, pneumatically, or by a combination thereof. The device may also include integral liquid pumps or be connectable to a pump to allow for pumping in the first channels and any other channels requiring flow. Examples of pressure pumps include syringe, peristaltic, diaphragm pumps, and sources of vacuum. Other pumps can employ centrifugal or electrokinetic forces. Alternatively, liquid movement may be controlled by gravity, capillarity, or surface treatments. Multiple pumps and mechanisms for liquid movement may be employed in a single device. The device may also include one or more vents to allow pressure equalization, and one or more filters to remove particulates or other undesirable components from a liquid. The device may also include one or more inlets and or outlets, e.g., to introduce liquids and/or remove droplets. Such additional components may be actuated or monitored by one or more controllers or computers operatively coupled to the device, e.g., by being integrated with, physically connected to (mechanically or electrically), or by wired or wireless connection.

Surface Properties

A surface of the device may include a material, coating, or surface texture that determines the physical properties of the device. In particular, the flow of liquids through a device of the invention may be controlled by the device surface properties (e.g., water contact angle of a liquid-contacting surface). In some cases, a device portion (e.g., a channel or droplet formation region) may have a surface having a water contact angle suitable for facilitating liquid flow (e.g., in a channel) or assisting droplet formation of a first liquid in a second liquid (e.g., in a droplet formation region).

A device may include a channel having a surface with a first water contact angle in fluid communication with (e.g., fluidically connected to) a droplet formation region having a surface with a second water contact angle. The surface water contact angles may be suited to producing droplets of a first liquid in a second liquid. In this non-limiting example, the channel carrying the first liquid may have surface with a first water contact angle suited for the first liquid wetting the channel surface. For example, when the first liquid is substantially miscible with water (e.g., the first liquid is an aqueous liquid), the first water contact angle may be about 95° or less (e.g., 90° or less). Additionally, in this non-limiting example, the droplet formation region may have a surface with a second water contact angle suited for the second liquid wetting the droplet formation region surface (e.g., shelf surface). For example, when the second liquid is substantially immiscible with water (e.g., the second liquid is an oil), the second water contact angle may be about 70° or more (e.g., 90° or more, 95° or more, or 100° or more). Typically, in this non-limiting example, the second water contact angle will differ from the first water contact angle by 5° to 100°. For example, when the first liquid is substantially miscible with water (e.g., the first liquid is an aqueous liquid), and the second liquid is substantially immiscible with water (e.g., the second liquid is an oil), the second water contact angle may be greater than the first water contact angle by 5° to 100°.

For example, portions of the device carrying aqueous phases (e.g., a channel) may have a surface with a water contact angle of less than or equal to about 90° (e.g., include a hydrophilic material or coating), and/or portions of the device housing an oil phase may have a surface with a water contact angle of greater than 70° (e.g., greater than 90°, greater than 95°, greater than 100° (e.g., 95°-120° or 100°-110°)), e.g., include a hydrophobic material or coating. In certain embodiments, the droplet formation region may include a material or surface coating that reduces or prevents wetting by aqueous phases. For example, the droplet formation region may have a surface with a water contact angle of greater than 70° (e.g., greater than 90°, greater than 95°, greater than 100° (e.g., 95°-120° or 100°-110°)). The device can be designed to have a single type of material or coating throughout. Alternatively, the device may have separate regions having different materials or coatings. Surface textures may also be employed to control fluid flow.

The device surface properties may be those of a native surface (i.e., the surface properties of the bulk material used for the device fabrication) or of a surface treatment. Non-limiting examples of surface treatments include, e.g., surface coatings and surface textures. In one approach, the device surface properties are attributable to one or more surface coatings present in a device portion. Hydrophobic coatings may include fluoropolymers (e.g., AQUAPEL® glass treatment), silanes, siloxanes, silicones, or other coatings known in the art. Other coatings include those vapor deposited from a precursor such as henicosyl-1,1,2,2-tetrahydrododecyldimethyltris(dimethylaminosilane); henicosyl-1,1,2,2-tetrahydrododecyltrichlorosilane (C12); heptadecafluoro-1,1,2,2-tetrahydrodecyltrichlorosilane (C10); nonafluoro-1,1,2,2-tetrahydrohexyltris(dimethylamino)silane; 3,3,3,4,4,5,5,6,6-nonafluorohexyltrichlorosilane; tridecafluoro-1,1,2,2-tetrahydrooctyltrichlorosilane (C8); bis(tridecafluoro-1,1,2,2-tetrahydrooctyl)dimethylsiloxymethylchlorosilane; nonafluorohexyltriethoxysilane (C6); dodecyltrichlorosilane (DTS); dimethyldichlorosilane (DDMS); or 10-undecenyl-trichlorosilane (V11); pentafluorophenylpropyltrichlorosilane (C5). Hydrophilic coatings include polymers such as polysaccharides, polyethylene glycol, polyamines, and polycarboxylic acids. Hydrophilic surfaces may also be created by oxygen plasma treatment of certain materials.

A coated surface may be formed by depositing a metal oxide onto a surface of the device. Example metal oxides useful for coating surfaces include, but are not limited to, $Al_2O_3$, $TiO_2$, $SiO_2$, or a combination thereof. Other metal oxides useful for surface modifications are known in the art. The metal oxide can be deposited onto a surface by standard deposition techniques, including, but not limited to, atomic layer deposition (ALD), physical vapor deposition (PVD), e.g., sputtering, chemical vapor deposition (CVD), or laser deposition. Other deposition techniques for coating surfaces, e.g., liquid-based deposition, are known in the art. For example, an atomic layer of $Al_2O_3$ can be deposited on a surface by contacting it with trimethylaluminum (TMA) and water.

In another approach, the device surface properties may be attributable to surface texture. For example, a surface may have a nanotexture, e.g., have a surface with nanometer surface features, such as cones or columns, that alters the wettability of the surface. Nanotextured surface may be hydrophilic, hydrophobic, or superhydrophobic, e.g., have a water contact angle greater than 150°. Exemplary superhydrophobic materials include Manganese Oxide Polystyrene ($MnO_2$/PS) nano-composite, Zinc Oxide Polystyrene (ZnO/PS) nano-composite, Precipitated Calcium Carbonate, Carbon nano-tube structures, and a silica nano-coating. Superhydrophobic coatings may also include a low surface energy material (e.g., an inherently hydrophobic material) and a surface roughness (e.g., using laser ablation techniques, plasma etching techniques, or lithographic techniques in which a material is etched through apertures in a patterned mask). Examples of low surface energy materials include fluorocarbon materials, e.g., polytetrafluoroethylene (PTFE), fluorinated ethylene propylene (FEP), ethylene tetrafluoroethylene (ETFE), ethylene chloro-trifluoroethylene (ECTFE), perfluoro-alkoxyalkane (PFA), poly(chloro-trifluoroethylene) (CTFE), perfluoro-alkoxyalkane (PFA), and poly(vinylidene fluoride) (PVDF). Other superhydrophobic surfaces are known in the art.

In some cases, the first water contact angle is less than or equal to about 90°, e.g., less than 80°, 70°, 60°, 50°, 40°, 30°, 20°, or 10°, e.g., 90°, 85°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, or 0°. In some cases, the second water contact angle is at least 70°, e.g., at least 80°, at least 85°, at least 90°, at least 95°, or at least 100° (e.g., about 100°, 101°, 102°, 103°, 104°, 105°, 106°, 107°, 108°, 109°, 110°, 115°, 120°, 125°, 130°, 135°, 140°, 145°, or about 150°).

The difference between the first and second water contact angles may be 5° to 100°, e.g., 5° to 80°, 5° to 60°, 5° to 50°, 5° to 40°, 5° to 30°, 5° to 20°, 10° to 75°, 15° to 70°, 20° to 65°, 25° to 60°, 30 to 50°, 35° to 45°, e.g., 5°, 6°, 7°, 8°, 9°, 10°, 15°, 20°, 25°, 30°, 35°, 40°, 45°, 50°, 55°, 60, 65°, 70°, 75°, 80°, 85°, 90°, 95°, or 100°.

The above discussion centers on the water contact angle. It will be understood that liquids employed in the devices and methods of the invention may not be water, or even aqueous. Accordingly, the actual contact angle of a liquid on a surface of the device may differ from the water contact angle.

Particles

The invention includes devices, systems, and kits having particles, e.g., for use in analyte detection. For example, particles configured with analyte detection moieties (e.g., barcodes, nucleic acids, binding molecules (e.g., proteins, peptides, aptamers, antibodies, or antibody fragments), enzymes, substrates, etc.) can be included in a droplet containing an analyte to modify the analyte and/or detect the presence or concentration of the analyte. In some embodiments, particles are synthetic particles (e.g., beads, e.g., gel beads).

For example, a droplet may include one or more analyte-detection moieties, e.g., unique identifiers, such as barcodes. Analyte-detection moieties, e.g., barcodes, may be introduced into droplets previous to, subsequent to, or concurrently with droplet formation. The delivery of the analyte-detection moieties, e.g., barcodes, to a particular droplet allows for the later attribution of the characteristics of an individual sample (e.g., biological particle) to the particular droplet. Analyte-detection moieties, e.g., barcodes, may be delivered, for example on a nucleic acid (e.g., an oligonucleotide), to a droplet via any suitable mechanism. Analyte-detection moieties, e.g., barcoded nucleic acids (e.g., oligonucleotides), can be introduced into a droplet via a particle, such as a microcapsule. In some cases, analyte-detection moieties, e.g., barcoded nucleic acids (e.g., oligonucleotides), can be initially associated with the particle (e.g., microcapsule) and then released upon application of a stimulus which allows the analyte-detection moieties, e.g., nucleic acids (e.g., oligonucleotides), to dissociate or to be released from the particle.

A particle, e.g., a bead, may be porous, non-porous, hollow (e.g., a microcapsule), solid, semi-solid, semi-fluidic, fluidic, and/or a combination thereof. In some instances, a particle, e.g., a bead, may be dissolvable, disruptable, and/or degradable. In some cases, a particle, e.g., a bead, may not be degradable. In some cases, the particle, e.g., a bead, may be a gel bead. A gel bead may be a hydrogel bead. A gel bead may be formed from molecular precursors, such as a polymeric or monomeric species. A semi-solid particle, e.g., a bead, may be a liposomal bead. Solid particles, e.g., beads, may comprise metals including iron oxide, gold, and silver. In some cases, the particle, e.g., the bead, may be a silica bead. In some cases, the particle, e.g., a bead, can be rigid. In other cases, the particle, e.g., a bead, may be flexible and/or compressible.

A particle, e.g., a bead, may comprise natural and/or synthetic materials. For example, a particle, e.g., a bead, can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, poly-ethylene terephthalate, poly(chlorotrifluoroethylene), poly (ethylene oxide), poly(ethylene terephthalate), polyethylene, polyisobutylene, poly(methyl methacrylate), poly(oxymethylene), polyformaldehyde, polypropylene, polystyrene, poly (tetrafluoroethylene), poly(vinyl acetate), poly(vinyl alcohol), poly(vinyl chloride), poly(vinylidene dichloride), poly (vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the particle, e.g., the bead, may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the particle, e.g., the bead, may comprise prepolymers, which are oligomers capable of further polymerization. For example, polyurethane beads may be prepared using prepolymers. In some cases, the particle, e.g., the bead, may contain individual polymers that may be further polymerized together. In some cases, particles, e.g., beads, may be generated via polymerization of different precursors, such that they comprise mixed polymers, co-polymers, and/or block co-polymers. In some cases, the particle, e.g., the bead, may comprise covalent or ionic bonds between polymeric precursors (e.g., monomers, oligomers, linear polymers), oligonucleotides, primers, and other entities. In some cases, the covalent bonds can be carbon-carbon bonds or thioether bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

Particles, e.g., beads, may be of uniform size or heterogeneous size. In some cases, the diameter of a particle, e.g., a bead, may be at least about 1 micrometer (µm), 5 µm, 10 µm, 20 µm, 30 µm, 40 µm, 50 µm, 60 µm, 70 µm, 80 µm, 90 µm, 100 µm, 250 µm, 500 µm, 1 mm, or greater. In some cases, a particle, e.g., a bead, may have a diameter of less than about 1 µm, 5 µm, 10 µm, 20 µm, 30 µm, 40 µm, 50 µm, 60 µm, 70 µm, 80 µm, 90 µm, 100 µm, 250 µm, 500 µm, 1 mm, or less. In some cases, a particle, e.g., a bead, may have a diameter in the range of about 40-75 µm, 30-75 µm, 20-75 µm, 40-85 µm, 40-95 µm, 20-100 µm, 10-100 µm, 1-100 µm, 20-250 µm, or 20-500 µm. The size of a particle, e.g., a bead, e.g., a gel bead, used to produce droplets is typically on the order of a cross section of the first channel (width or depth). In some cases, the gel beads are larger than the width and/or depth of the first channel and/or shelf, e.g., at least 1.5×, 2×, 3×, or 4× larger than the width and/or depth of the first channel and/or shelf.

In certain embodiments, particles, e.g., beads, can be provided as a population or plurality of particles, e.g., beads, having a relatively monodisperse size distribution. Where it may be desirable to provide relatively consistent amounts of reagents within droplets, maintaining relatively consistent particle, e.g., bead, characteristics, such as size, can contribute to the overall consistency. In particular, the particles, e.g., beads, described herein may have size distributions that have a coefficient of variation in their cross-sectional dimensions of less than 50%, less than 40%, less than 30%, less than 20%, and in some cases less than 15%, less than 10%, less than 5%, or less.

Particles may be of any suitable shape. Examples of particles, e.g., beads, shapes include, but are not limited to, spherical, non-spherical, oval, oblong, amorphous, circular, cylindrical, and variations thereof.

A particle, e.g., bead, injected or otherwise introduced into a droplet may comprise releasably, cleavably, or reversibly attached analyte detection moieties (e.g., barcodes). A particle, e.g., bead, injected or otherwise introduced into a droplet may comprise activatable analyte detection moieties (e.g., barcodes). A particle, e.g., bead, injected or otherwise introduced into a droplet may be a degradable, disruptable, or dissolvable particle, e.g., dissolvable bead.

Particles, e.g., beads, within a channel may flow at a substantially regular flow profile (e.g., at a regular flow rate). Such regular flow profiles can permit a droplet, when formed, to include a single particle (e.g., bead) and a single cell or other biological particle. Such regular flow profiles may permit the droplets to have an dual occupancy (e.g., droplets having at least one bead and at least one cell or other biological particle) greater than 5%, 10%, 20%, 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97% 98%, or 99% of the population. In some embodiments, the droplets have a 1:1 dual occupancy (i.e., droplets having exactly one particle (e.g., bead) and exactly one cell or other biological particle) greater than 5%, 10%, 20%, 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97% 98%, or 99% of the population. Such regular flow profiles and devices that may be used to provide such regular flow profiles are provided, for example, in U.S. Patent Publication No. 2015/0292988, which is entirely incorporated herein by reference.

As discussed above, analyte-detection moieties (e.g., barcodes) can be releasably, cleavably or reversibly attached to the particles, e.g., beads, such that analyte detection moieties (e.g., barcodes) can be released or be releasable through cleavage of a linkage between the barcode molecule and the particle, e.g., bead, or released through degradation of the particle (e.g., bead) itself, allowing the barcodes to be accessed or be accessible by other reagents, or both. Releasable analyte-detection moieties (e.g., barcodes) may sometimes be referred to as activatable analyte-detection moieties (e.g., activatable barcodes), in that they are available for reaction once released. Thus, for example, an activatable analyte detection-moiety (e.g., activatable barcode) may be activated by releasing the analyte detection moiety (e.g., barcode) from a particle, e.g., bead (or other suitable type of droplet described herein). Other activatable configurations are also envisioned in the context of the described methods and systems.

In addition to, or as an alternative to the cleavable linkages between the particles, e.g., beads, and the associated antigen detection moieties, such as barcode containing nucleic acids (e.g., oligonucleotides), the particles, e.g., beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a particle, e.g., bead, may be dissolvable, such that material components of the particle, e.g., bead, are degraded or solubilized when exposed to a particular chemical species or an environmental change, such as a change temperature or a change in pH. In some cases, a gel bead can be degraded or dissolved at elevated temperature and/or in basic conditions. In some cases, a particle, e.g., bead, may be thermally degradable such that when the particle, e.g., bead, is exposed to an appropriate change in temperature (e.g., heat), the particle, e.g., bead, degrades. Degradation or dissolution of a particle (e.g., bead) bound to a species (e.g., a nucleic acid, e.g., an oligonucleotide, e.g., barcoded oligonucleotide) may result in release of the species from the particle, e.g., bead. As will be appreciated from the above disclosure, the degradation of a particle, e.g., bead, may refer to the disassociation of a bound or entrained species from a particle, e.g., bead, both with and without structurally degrading the physical particle, e.g., bead, itself. For example, entrained species may be released from particles, e.g., beads, through osmotic pressure differences due to, for example, changing chemical environments. By way of example, alteration of particle, e.g., bead, pore sizes due to osmotic pressure differences can generally occur without structural degradation of the particle, e.g., bead, itself. In some cases, an increase in pore size due to osmotic swelling of a particle, e.g., bead or microcapsule (e.g., liposome), can permit the release of entrained species within the particle. In other cases, osmotic shrinking of a particle may cause the particle, e.g., bead, to better retain an entrained species due to pore size contraction.

A degradable particle, e.g., bead, may be introduced into a droplet, such as a droplet of an emulsion or a well, such that the particle, e.g., bead, degrades within the droplet and any associated species (e.g., nucleic acids, oligonucleotides, or fragments thereof) are released within the droplet when the appropriate stimulus is applied. The free species (e.g., nucleic acid, oligonucleotide, or fragment thereof) may interact with other reagents contained in the droplet. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in particle, e.g., bead, degradation and release of the barcode sequence into the aqueous, inner environment of the droplet. In another example, heating of a droplet comprising a particle-, e.g., bead-, bound analyte-detection moiety (e.g., barcode) in basic solution may also result in particle, e.g., bead, degradation and release of the attached barcode sequence into the aqueous, inner environment of the droplet.

Any suitable number of analyte-detection moieties (e.g., molecular tag molecules (e.g., primer, barcoded oligonucleotide, etc.)) can be associated with a particle, e.g., bead, such that, upon release from the particle, the analyte detection moieties (e.g., molecular tag molecules (e.g., primer, e.g., barcoded oligonucleotide, etc.)) are present in the droplet at a pre-defined concentration. Such pre-defined concentration may be selected to facilitate certain reactions for generating a sequencing library, e.g., amplification, within the droplet. In some cases, the pre-defined concentration of a primer can be limited by the process of producing oligonucleotide-bearing particles, e.g., beads.

Additional reagents may be included as part of the particles (e.g., analyte-detection moieties) and/or in solution or dispersed in the droplet, for example, to activate, mediate, or otherwise participate in a reaction, e.g., between the analyte and analyte-detection moiety.

Biological Samples

A droplet of the present disclosure may include biological particles (e.g., cells) and/or macromolecular constituents thereof (e.g., components of cells (e.g., intracellular or extracellular proteins, nucleic acids, glycans, or lipids) or products of cells (e.g., secretion products)). An analyte from a biological particle, e.g., component or product thereof, may be considered to be a bioanalyte. In some embodiments, a biological particle, e.g., cell, or product thereof is included in a droplet, e.g., with one or more particles (e.g., beads) having an analyte detection moiety. A biological particle, e.g., cell, and/or components or products thereof can, in some embodiments, be encased inside a gel, such as via polymerization of a droplet containing the biological particle and precursors capable of being polymerized or gelled.

In the case of encapsulated biological particles (e.g., cells), a biological particle may be included in a droplet that contains lysis reagents in order to release the contents (e.g., contents containing one or more analytes (e.g., bioanalytes)) of the biological particles within the droplet. In such cases, the lysis agents can be contacted with the biological particle suspension concurrently with, or immediately prior to the introduction of the biological particles into the droplet formation region, for example, through an additional channel or channels upstream or proximal to a second channel or a third channel that is upstream or proximal to a second droplet formation region. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, Mo.), as well as other commercially available lysis enzymes. Other lysis agents may additionally or alternatively be contained in a droplet with the biological particles (e.g., cells) to cause the release of the biological particles' contents into the droplets. For example, in some cases, surfactant based lysis solutions may be used to lyse cells, although these may be less desirable for emulsion based systems where the surfactants can interfere with stable emulsions. In some cases, lysis solutions may include non-ionic surfactants such as, for example, TRITON X-100 and TWEEN 20. In some cases, lysis solutions may include ionic surfactants such as, for example, sarcosyl and sodium dodecyl sulfate (SDS). In some embodiments, lysis solutions are hypotonic, thereby lysing cells by osmotic shock. Electroporation, thermal, acoustic or mechanical cellular disruption may also be used in certain cases, e.g., non-emulsion based droplet formation such as encapsulation of biological particles that may be in addition to or in place of droplet formation, where any pore size of the encapsulate is sufficiently small to retain nucleic acid fragments of a desired size, following cellular disruption.

In addition to the lysis agents, other reagents can also be included in droplets with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles (e.g., cells), the biological particles may be exposed to an appropriate stimulus to release the biological particles or their contents from a microcapsule within a droplet. For example, in some cases, a chemical stimulus may be included in a droplet along with an encapsulated biological particle to allow for degradation of the encapsulating matrix and release of the cell or its contents into the larger droplet. In some cases, this stimulus may be the same as the stimulus described elsewhere herein for release of analyte detection moieties (e.g., oligonucleotides) from their respective particle (e.g., bead). In alternative aspects, this may be a different and non-overlapping stimulus, in order to allow an encapsulated biological particle to be released into a droplet at a different time from the release of analyte detection moieties (e.g., oligonucleotides) into the same droplet.

Additional reagents may also be included in droplets with the biological particles, such as endonucleases to fragment a biological particle's DNA, DNA polymerase enzymes and dNTPs used to amplify the biological particle's nucleic acid fragments and to attach the barcode molecular tags to the amplified fragments. Other reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyinosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250 nucleotides or longer.

In some cases, the length of a switch oligo may be at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective droplets, the macromolecular components (e.g., macromolecular constituents of biological particles, such as RNA, DNA, or proteins) contained therein may be further processed within the droplets.

As described above, the macromolecular components (e.g., bioanalytes) of individual biological particles (e.g., cells) can be provided with unique identifiers (e.g., barcodes) such that upon characterization of those macromolecular components, at which point components from a heterogeneous population of cells may have been mixed and are interspersed or solubilized in a common liquid, any given component (e.g., bioanalyte) may be traced to the biological particle (e.g., cell) from which it was obtained. The ability to attribute characteristics to individual biological particles or groups of biological particles is provided by the assignment of unique identifiers specifically to an individual biological particle or groups of biological particles. Unique identifiers, for example, in the form of nucleic acid barcodes, can be assigned or associated with individual biological particles (e.g., cells) or populations of biological particles (e.g., cells), in order to tag or label the biological particle's macromolecular components (and as a result, its characteristics) with the unique identifiers. These unique identifiers can then be used to attribute the biological particle's components and characteristics to an individual biological particle or group of biological particles. This can be performed by forming droplets including the individual biological particle or groups of biological particles with the unique identifiers (via particles, e.g., beads), as described in the systems and methods herein.

In some aspects, the unique identifiers are provided in the form of oligonucleotides that comprise nucleic acid barcode sequences that may be attached to or otherwise associated with the nucleic acid contents of individual biological particle, or to other components of the biological particle, and particularly to fragments of those nucleic acids. The oligonucleotides are partitioned such that as between oligonucleotides in a given droplet, the nucleic acid barcode sequences contained therein are the same, but as between different droplets, the oligonucleotides can, and do have differing barcode sequences, or at least represent a large number of different barcode sequences across all of the droplets in a given analysis. In some aspects, only one nucleic acid barcode sequence can be associated with a given droplet, although in some cases, two or more different barcode sequences may be present.

The nucleic acid barcode sequences can include from 6 to about 20 or more nucleotides within the sequence of the oligonucleotides. In some cases, the length of a barcode sequence may be 6, 7, 8, 9, 10, 11, 12, 13, 14, 15, 16, 17, 18, 19, 20 nucleotides or longer. In some cases, the length of a barcode sequence may be at least 6, 7, 8, 9, 10, 11, 12, 13, 14, 15, 16, 17, 18, 19, 20 nucleotides or longer. In some cases, the length of a barcode sequence may be at most 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be 4, 5, 6, 7, 8, 9, 10, 11, 12, 13, 14, 15, 16 nucleotides or longer. In some cases, the barcode subsequence may be at least 4, 5, 6, 7, 8, 9, 10, 11, 12, 13, 14, 15, 16 nucleotides or longer. In some cases, the barcode subsequence may be at most 4, 5, 6, 7, 8, 9, 10, 11, 12, 13, 14, 15, 16 nucleotides or shorter.

Analyte-detection moieties (e.g., oligonucleotides) in droplets can also include other functional sequences useful in processing of nucleic acids from biological particles contained in the droplet. These sequences include, for example, targeted or random/universal amplification primer sequences for amplifying the genomic DNA from the individual biological particles within the droplets while attaching the associated barcode sequences, sequencing primers or primer recognition sites, hybridization or probing sequences, e.g., for identification of presence of the sequences or for pulling down barcoded nucleic acids, or any of a number of other potential functional sequences.

Other mechanisms of forming droplets containing oligonucleotides may also be employed, including, e.g., coalescence of two or more droplets, where one droplet contains oligonucleotides, or microdispensing of oligonucleotides into droplets, e.g., droplets within microfluidic systems.

In an example, particles (e.g., beads) are provided that each include large numbers of the above described barcoded oligonucleotides releasably attached to the beads, where all of the oligonucleotides attached to a particular bead will include the same nucleic acid barcode sequence, but where a large number of diverse barcode sequences are represented across the population of beads used. In some embodiments, hydrogel beads, e.g., beads having polyacrylamide polymer matrices, are used as a solid support and delivery vehicle for the oligonucleotides into the droplets, as they are capable of carrying large numbers of oligonucleotide molecules, and may be configured to release those oligonucleotides upon exposure to a particular stimulus, as described elsewhere herein. In some cases, the population of beads will provide a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of oligonucleotide molecules attached. In particular, the number of molecules of oligonucleotides including the barcode sequence on an individual bead can be at least about 1,000 oligonucleotide molecules, at least about 5,000 oligonucleotide molecules, at least about 10,000 oligonucleotide molecules, at least about 50,000 oligonucleotide molecules, at least about 100,000 oligonucleotide molecules, at least about 500,000 oligonucleotides, at least about 1,000,000 oligonucleotide molecules, at least about 5,000,000 oligonucleotide molecules, at least about 10,000,000 oligonucleotide molecules, at least about 50,000,000 oligonucleotide molecules, at least about 100,000,000 oligonucleotide molecules, and in some cases at least about 1 billion oligonucleotide molecules, or more.

Moreover, when the population of beads are included in droplets, the resulting population of droplets can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each droplet of the population can include at least about 1,000 oligonucleotide molecules, at least about 5,000 oligonucleotide molecules, at least about 10,000 oligonucleotide molecules, at least about 50,000 oligonucleotide molecules, at least about 100,000 oligonucleotide molecules, at least about 500,000 oligonucleotides, at least about 1,000,000 oligonucleotide molecules, at least about 5,000,000 oligonucleotide molecules, at least about 10,000,000 oligonucleotide molecules, at least about 50,000,000 oligonucleotide molecules, at least about 100,000,000 oligonucleotide molecules, and in some cases at least about 1 billion oligonucleotide molecules.

In some cases, it may be desirable to incorporate multiple different barcodes within a given droplet, either attached to a single or multiple particles, e.g., beads, within the droplet. For example, in some cases, mixed, but known barcode sequences set may provide greater assurance of identification in the subsequent processing, for example, by providing a stronger address or attribution of the barcodes to a given droplet, as a duplicate or independent confirmation of the output from a given droplet.

Oligonucleotides may be releasable from the particles (e.g., beads) upon the application of a particular stimulus. In some cases, the stimulus may be a photo-stimulus, e.g., through cleavage of a photo-labile linkage that releases the oligonucleotides. In other cases, a thermal stimulus may be used, where increase in temperature of the particle, e.g., bead, environment will result in cleavage of a linkage or other release of the oligonucleotides form the particles, e.g., beads. In still other cases, a chemical stimulus is used that cleaves a linkage of the oligonucleotides to the beads, or otherwise results in release of the oligonucleotides from the particles, e.g., beads. In one case, such compositions include the polyacrylamide matrices described above for encapsulation of biological particles, and may be degraded for release of the attached oligonucleotides through exposure to a reducing agent, such as dithiothreitol (DTT).

The droplets described herein may contain either one or more biological particles (e.g., cells), either one or more barcode carrying particles, e.g., beads, or both at least a biological particle and at least a barcode carrying particle, e.g., bead. In some instances, a droplet may be unoccupied and contain neither biological particles nor barcode-carrying particles, e.g., beads. As noted previously, by controlling the flow characteristics of each of the liquids combining at the droplet formation region(s), as well as controlling the geometry of the droplet formation region(s), droplet formation can be optimized to achieve a desired occupancy level of particles, e.g., beads, biological particles, or both, within the droplets that are generated.

Kits and Systems

Devices of the invention may be combined with various external components, e.g., pumps, reservoirs, or controllers, reagents, e.g., analyte detection moieties, liquids, particles (e.g., beads), and/or sample in the form of kits and systems.

Methods

The methods described herein to generate droplets, e.g., of uniform and predictable sizes, and with high throughput, may be used to greatly increase the efficiency of single cell applications and/or other applications receiving droplet-based input. Such single cell applications and other applications may often be capable of processing a certain range of droplet sizes. The methods may be employed to generate droplets for use as microscale chemical reactors, where the volumes of the chemical reactants are small (~pLs).

The methods disclosed herein may produce emulsions, generally, i.e., droplet of a dispersed phases in a continuous phase. For example, droplets may include a first liquid, and the other liquid may be a second liquid. The first liquid may be substantially immiscible with the second liquid. In some instances, the first liquid may be an aqueous liquid or may be substantially miscible with water. Droplets produced according to the methods disclosed herein may combine multiple liquids. For example, a droplet may combine a first and third liquids. The first liquid may be substantially miscible with the third liquid. The second liquid may be an oil, as described herein.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

The methods described herein may allow for the production of one or more droplets containing a single particle, e.g., bead, and/or single biological particle (e.g., cell) with uniform and predictable droplet size. The methods also allow for the production of one or more droplets comprising a single biological particle (e.g., cell) and more than one particle, e.g., bead, one or more droplets comprising more than one biological particle (e.g., cell) and a single particle, e.g., bead, and/or one or more droplets comprising more than one biological particle (e.g., cell) and more than one particle, e.g., beads. The methods may also allow for increased throughput of droplet formation.

Droplets are in general formed by allowing a first liquid to flow into a second liquid in a droplet formation region, where droplets spontaneously form as described herein. The droplets may comprise an aqueous liquid dispersed phase within a non-aqueous continuous phase, such as an oil phase. In some cases, droplet formation may occur in the absence of externally driven movement of the continuous phase, e.g., a second liquid, e.g., an oil. As discussed above, the continuous phase may nonetheless be externally driven, even though it is not required for droplet formation. Emulsion systems for creating stable droplets in non-aqueous (e.g., oil) continuous phases are described in detail in, for example, U.S. Pat. No. 9,012,390, which is entirely incorporated herein by reference for all purposes. Alternatively or in addition, the droplets may comprise, for example, microvesicles that have an outer barrier surrounding an inner liquid center or core. In some cases, the droplets may comprise a porous matrix that is capable of entraining and/or retaining materials within its matrix. A variety of different vessels are described in, for example, U.S. Patent Application Publication No. 2014/0155295, which is entirely incorporated herein by reference for all purposes. The droplets can be collected in a substantially stationary volume of liquid, e.g., with the buoyancy of the formed droplets moving them out of the path of nascent droplets (up or down depending on the relative density of the droplets and continuous phase). Alternatively or in addition, the formed droplets can be moved out of the path of nascent droplets actively, e.g., using a gentle flow of the continuous phase, e.g., a liquid stream or gently stirred liquid.

Allocating particles, e.g., beads (e.g., microcapsules carrying barcoded oligonucleotides) or biological particles (e.g., cells) to discrete droplets may generally be accomplished by introducing a flowing stream of particles, e.g., beads, in an aqueous liquid into a flowing stream or non-flowing reservoir of a non-aqueous liquid, such that droplets are generated. In some instances, the occupancy of the resulting droplets (e.g., number of particles, e.g., beads, per droplet) can be controlled by providing the aqueous stream at a certain concentration or frequency of particles, e.g., beads. In some instances, the occupancy of the resulting droplets can also be controlled by adjusting one or more geometric features at the point of droplet formation, such as a width of a fluidic channel carrying the particles, e.g., beads, relative to a diameter of a given particles, e.g., beads.

Where single particle-, e.g., bead-, containing droplets are desired, the relative flow rates of the liquids can be selected such that, on average, the droplets contain fewer than one particle, e.g., bead, per droplet in order to ensure that those droplets that are occupied are primarily singly occupied. In some embodiments, the relative flow rates of the liquids can be selected such that a majority of droplets are occupied, for example, allowing for only a small percentage of unoccupied droplets. The flows and channel architectures can be controlled as to ensure a desired number of singly occupied droplets, less than a certain level of unoccupied droplets and/or less than a certain level of multiply occupied droplets.

The methods described herein can be operated such that a majority of occupied droplets include no more than one biological particle per occupied droplet. In some cases, the droplet formation process is conducted such that fewer than 25% of the occupied droplets contain more than one biological particle (e.g., multiply occupied droplets), and in many cases, fewer than 20% of the occupied droplets have more than one biological particle. In some cases, fewer than 10% or even fewer than 5% of the occupied droplets include more than one biological particle per droplet.

It may be desirable to avoid the creation of excessive numbers of empty droplets, for example, from a cost perspective and/or efficiency perspective. However, while this may be accomplished by providing sufficient numbers of particles, e.g., beads, into the droplet formation region, the Poisson distribution may expectedly increase the number of droplets that may include multiple biological particles. As such, at most about 95%, 90%, 85%, 80%, 75%, 70%, 65%, 60%, 55%, 50%, 45%, 40%, 35%, 30%, 25%, 20%, 15%, 10%, 5% or less of the generated droplets can be unoccupied. In some cases, the flow of one or more of the particles, or liquids directed into the droplet formation region can be conducted such that, in many cases, no more than about 50% of the generated droplets, no more than about 25% of the generated droplets, or no more than about 10% of the generated droplets are unoccupied. These flows can be controlled so as to present non-Poisson distribution of singly occupied droplets while providing lower levels of unoccupied droplets. The above noted ranges of unoccupied droplets can be achieved while still providing any of the single occupancy rates described above. For example, in many cases, the use of the systems and methods described herein creates resulting droplets that have multiple occupancy rates of less than about 25%, less than about 20%, less than about 15%, less than about 10%, and in many cases, less than about 5%, while having unoccupied droplets of less than about 50%, less than about 40%, less than about 30%, less than about 20%, less than about 10%, less than about 5%, or less.

The flow of the first fluid may be such that the droplets contain a single particle, e.g., bead. In certain embodiments, the yield of droplets containing a single particle is at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

As will be appreciated, the above-described occupancy rates are also applicable to droplets that include both biological particles (e.g., cells) and beads. The occupied droplets (e.g., at least about 10%, 20%, 30%, 40%, 50%, 60%, 70%, 80%, 90%, 95%, or 99% of the occupied droplets) can include both a bead and a biological particle. Particles, e.g., beads, within a channel (e.g., a particle channel) may flow at a substantially regular flow profile (e.g., at a regular flow rate) to provide a droplet, when formed, with a single particle (e.g., bead) and a single cell or other biological particle. Such regular flow profiles may permit the droplets to have a dual occupancy (e.g., droplets having at least one bead and at least one cell or biological particle) greater than 5%, 10%, 20%, 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97% 98%, or 99%. In some embodiments, the droplets have a 1:1 dual occupancy (i.e., droplets having exactly one particle (e.g., bead) and exactly one cell or biological particle) greater than 5%, 10%, 20%, 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97% 98%, or 99%. Such regular flow profiles and devices that may be used to provide such regular flow profiles are provided, for example, in U.S. Patent Publication No. 2015/0292988, which is entirely incorporated herein by reference.

In some cases, additional particles may be used to deliver additional reagents to a droplet. In such cases, it may be advantageous to introduce different particles (e.g., beads) into a common channel (e.g., proximal to or upstream from a droplet formation region) or droplet formation intersection from different bead sources (e.g., containing different associated reagents) through different channel inlets into such common channel or droplet formation region. In such cases, the flow and/or frequency of each of the different particle, e.g., bead, sources into the channel or fluidic connections may be controlled to provide for the desired ratio of particles, e.g., beads, from each source, while optionally ensuring the desired pairing or combination of such particles, e.g., beads, are formed into a droplet with the desired number of biological particles.

The droplets described herein may comprise small volumes, for example, less than about 10 microliters (µL), 5 µL, 1 µL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less. For example, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where the droplets further comprise particles (e.g., beads or microcapsules), it will be appreciated that the sample liquid volume within the droplets may be less than about 90% of the above described volumes, less than about 80%, less than about 70%, less than about 60%, less than about 50%, less than about 40%, less than about 30%, less than about 20%, or less than about 10% the above described volumes (e.g., of a partitioning liquid), e.g., from 1% to 99%, from 5% to 95%, from 10% to 90%, from 20% to 80%, from 30% to 70%, or from 40% to 60%, e.g., from 1% to 5%, 5% to 10%, 10% to 15%, 15% to 20%, 20% to 25%, 25% to 30%, 30% to 35%, 35% to 40%, 40% to 45%, 45% to 50%, 50% to 55%, 55% to 60%, 60% to 65%, 65% to 70%, 70% to 75%, 75% to 80%, 80% to 85%, 85% to 90%, 90% to 95%, or 95% to 100% of the above described volumes.

Any suitable number of droplets can be generated. For example, in a method described herein, a plurality of droplets may be generated that comprises at least about 1,000 droplets, at least about 5,000 droplets, at least about 10,000 droplets, at least about 50,000 droplets, at least about 100,000 droplets, at least about 500,000 droplets, at least about 1,000,000 droplets, at least about 5,000,000 droplets at least about 10,000,000 droplets, at least about 50,000,000 droplets, at least about 100,000,000 droplets, at least about 500,000,000 droplets, at least about 1,000,000,000 droplets, or more. Moreover, the plurality of droplets may comprise both unoccupied droplets (e.g., empty droplets) and occupied droplets.

The fluid to be dispersed into droplets may be transported from a reservoir to the droplet formation region. Alternatively, the fluid to be dispersed into droplets is formed in situ by combining two or more fluids in the device. For example, the fluid to be dispersed may be formed by combining one fluid containing one or more reagents with one or more other fluids containing one or more reagents. In these embodiments, the mixing of the fluid streams may result in a chemical reaction. For example, when a particle is employed, a fluid having reagents that disintegrates the particle may be combined with the particle, e.g., immediately upstream of the droplet generating region. In these embodiments, the particles may be cells, which can be combined with lysing reagents, such as surfactants. When particles, e.g., beads, are employed, the particles, e.g., beads, may be dissolved or chemically degraded, e.g., by a change in pH (acid or base), redox potential (e.g., addition of an oxidizing or reducing agent), enzymatic activity, change in salt or ion concentration, or other mechanism.

The first fluid is transported through the first channel at a flow rate sufficient to produce droplets in the droplet formation region. Faster flow rates of the first fluid generally increase the rate of droplet production; however, at a high enough rate, the first fluid will form a jet, which may not break up into droplets. Typically, the flow rate of the first fluid though the first channel may be between about 0.01 µL/min to about 100 µL/min, e.g., 0.1 to 50 µL/min, 0.1 to 10 µL/min, or 1 to 5 µL/min. In some instances, the flow rate of the first liquid may be between about 0.04 µL/min and about 40 µL/min. In some instances, the flow rate of the first liquid may be between about 0.01 µL/min and about 100 µL/min. Alternatively, the flow rate of the first liquid may be less than about 0.01 µL/min. Alternatively, the flow rate of the first liquid may be greater than about 40 µL/min, e.g., 45 µL/min, 50 µL/min, 55 µL/min, 60 µL/min, 65 µL/min, 70 µL/min, 75 µL/min, 80 µL/min, 85 µL/min, 90 µL/min, 95 µL/min, 100 µL/min, 110 µL/min, 120 µL/min, 130 µL/min, 140 µL/min, 150 µL/min, or greater. At lower flow rates, such as flow rates of about less than or equal to 10 µL/min, the droplet radius may not be dependent on the flow rate of first liquid. Alternatively or in addition, for any of the abovementioned flow rates, the droplet radius may be independent of the flow rate of the first liquid.

The typical droplet formation rate for a single channel in a device of the invention is between 0.1 Hz to 10,000 Hz, e.g., 1 to 1000 Hz or 1 to 500 Hz. The use of multiple first channels can increase the rate of droplet formation by increasing the number of locations of formation.

As discussed above, droplet formation may occur in the absence of externally driven movement of the continuous phase. In such embodiments, the continuous phase flows in response to displacement by the advancing stream of the first fluid or other forces. Channels may be present in the droplet formation region, e.g., including a shelf region, to allow more rapid transport of the continuous phase around the first fluid. This increase in transport of the continuous phase can increase the rate of droplet formation. Alternatively, the continuous phase may be actively transported. For example, the continuous phase may be actively transported into the droplet formation region, e.g., including a shelf region, to increase the rate of droplet formation; continuous phase may be actively transported to form a sheath flow around the first fluid as it exits the distal end; or the continuous phase may be actively transported to move droplets away from the point of formation.

Additional factors that affect the rate of droplet formation include the viscosity of the first fluid and of the continuous phase, where increasing the viscosity of either fluid reduces the rate of droplet formation. In certain embodiments, the viscosity of the first fluid and/or continuous is between 0.5 cP to 10 cP. Furthermore, lower interfacial tension results in slower droplet formation. In certain embodiments, the interfacial tension is between 0.1 and 100 mN/m, e.g., 1 to 100 mN/m or 2 mN/m to 60 mN/m. The depth of the shelf region can also be used to control the rate of droplet formation, with a shallower depth resulting in a faster rate of formation.

The methods may be used to produce droplets in range of 1 µm to 500 µm in diameter, e.g., 1 to 250 µm, 5 to 200 µm, 5 to 150 µm, or 12 to 125 µm. Factors that affect the size of the droplets include the rate of formation, the cross-sectional dimension of the distal end of the first channel, the depth of the shelf, and fluid properties and dynamic effects, such as the interfacial tension, viscosity, and flow rate.

The first liquid may be aqueous, and the second liquid may be an oil (or vice versa). Examples of oils include perfluorinated oils, mineral oil, and silicone oils. For example, a fluorinated oil may include a fluorosurfactant for stabilizing the resulting droplets, for example, inhibiting subsequent coalescence of the resulting droplets. Examples of particularly useful liquids and fluorosurfactants are described, for example, in U.S. Pat. No. 9,012,390, which is entirely incorporated herein by reference for all purposes. Specific examples include hydrofluoroethers, such as HFE 7500, 7300, 7200, or 7100. Suitable liquids are those described in US 2015/0224466 and U.S. 62/522,292, the liquids of which are hereby incorporated by reference. In some cases, liquids include additional components such as a particle, e.g., a cell or a gel bead. As discussed above, the first fluid or continuous phase may include reagents for carrying out various reactions, such as nucleic acid amplification, lysis, or bead dissolution. The first liquid or continuous phase may include additional components that stabilize or otherwise affect the droplets or a component inside the droplet. Such additional components include surfactants, antioxidants, preservatives, buffering agents, antibiotic agents, salts, chaotropic agents, enzymes, nanoparticles, and sugars.

Devices, systems, compositions, and methods of the present disclosure may be used for various applications, such as, for example, processing a single analyte (e.g., bioanalytes, e.g., RNA, DNA, or protein) or multiple analytes (e.g., bioanalytes, e.g., DNA and RNA, DNA and protein, RNA and protein, or RNA, DNA and protein) from a single cell. For example, a biological particle (e.g., a cell or virus) can be formed in a droplet, and one or more analytes (e.g., bioanalytes) from the biological particle (e.g., cell) can be modified or detected (e.g., bound, labeled, or otherwise modified by an analyte detection moiety) for subsequent processing. The multiple analytes may be from the single cell. This process may enable, for example, proteomic, transcriptomic, and/or genomic analysis of the cell or population thereof (e.g., simultaneous proteomic, transcriptomic, and/or genomic analysis of the cell or population thereof).

Methods of modifying analytes include providing a plurality of particles (e.g., beads) in a liquid carrier (e.g., an aqueous carrier); providing a sample containing an analyte (e.g., as part of a cell, or component or product thereof) in a sample liquid; and using the device to combine the liquids and form an analyte detection droplet containing one or more particles and one or more analytes (e.g., as part of one or more cells, or components or products thereof). Such sequestration of one or more particles with analyte (e.g., bioanalyte associated with a cell) in a droplet enables labeling of discrete portions of large, heterologous samples (e.g., single cells within a heterologous population). Once labeled or otherwise modified, droplets can be combined (e.g., by breaking an emulsion), and the resulting liquid can be analyzed to determine a variety of properties associated with each of numerous single cells.

In particular embodiments, the invention features methods of producing analyte detection droplets using a device having a particle channel and a sample channel that intersect proximal to a droplet formation region. Particles having an analyte-detection moiety in a liquid carrier flow proximal-to-distal through the particle channel and a sample liquid containing an analyte flows proximal-to-distal through the sample channel until the two liquids meet and combine at the intersection of the sample channel and the particle channel, upstream (and/or proximal to) the droplet formation region. The combination of the liquid carrier with the sample liquid results in an analyte detection liquid. In some embodiments, the two liquids are miscible (e.g., they both contain solutes in water or aqueous buffer). The combination of the two liquids can occur at a controlled relative rate, such that the analyte detection liquid has a desired volumetric ratio of particle liquid to sample liquid, a desired numeric ratio of particles to cells, or a combination thereof (e.g., one particle per cell per 50 pL). As the analyte detection liquid flows through the droplet formation region into a partitioning liquid (e.g., a liquid which is immiscible with the analyte detection liquid, such as an oil), analyte detection droplets form. These analyte detection droplets may continue to flow through one or more channels. Alternatively or in addition, the analyte detection droplets may accumulate (e.g., as a substantially stationary population) in a droplet collection region. In some cases, the accumulation of a population of droplets may occur by a gentle flow of a fluid within the droplet collection region, e.g., to move the formed droplets out of the path of the nascent droplets.

Devices useful for analyte detection may feature any combination of elements described herein. For example, various droplet formation regions can be employed in the design of a device for analyte detection. In some embodiments, analyte detection droplets are formed at a droplet formation region having a shelf region, where the analyte detection liquid expands in at least one dimension as it passes through the droplet formation region. Any shelf region described herein can be useful in the methods of analyte detection droplet formation provided herein. Additionally or alternatively, the droplet formation region may have a step at or distal to an inlet of the droplet formation region (e.g., within the droplet formation region or distal to the droplet formation region). In some embodiments, analyte detection droplets are formed without externally driven flow of a continuous phase (e.g., by one or more crossing flows of liquid at the droplet formation region). Alternatively, analyte detection droplets are formed in the presence of an externally driven flow of a continuous phase.

A device useful for droplet formation, e.g., analyte detection, may feature multiple droplet formation regions (e.g., in or out of (e.g., as independent, parallel circuits) fluid communication with one another. For example, such a device may have 2-100, 3-50, 4-40, 5-30, 6-24, 8-18, or 9-12, e.g., 2-6, 6-12, 12-18, 18-24, 24-36, 36-48, or 48-96, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more droplet formation regions configured to produce analyte detection droplets).

Source reservoirs can store liquids prior to and during droplet formation. In some embodiments, a device useful in analyte detection droplet formation includes one or more particle reservoirs connected proximally to one or more particle channels. Particle suspensions can be stored in particle reservoirs prior to analyte detection droplet formation. Particle reservoirs can be configured to store particles containing an analyte detection moiety. For example, particle reservoirs can include, e.g., a coating to prevent adsorption or binding (e.g., specific or non-specific binding) of particles or analyte-detection moieties. Additionally or alternatively, particle reservoirs can be configured to minimize degradation of analyte detection moieties (e.g., by containing nuclease, e.g., DNAse or RNAse) or the particle matrix itself, accordingly.

Additionally or alternatively, a device includes one or more sample reservoirs connected proximally to one or more sample channels. Samples containing cells and/or other reagents useful in analyte detection and/or droplet formation can be stored in sample reservoirs prior to analyte detection droplet formation. Sample reservoirs can be configured to reduce degradation of sample components, e.g., by including nuclease (e.g., DNAse or RNAse).

Methods of the invention include administering a sample and/or particles to the device, for example, (a) by pipetting a sample liquid, or a component or concentrate thereof, into a sample reservoir and/or (b) by pipetting a liquid carrier (e.g., an aqueous carrier) and/or particles into a particle reservoir. In some embodiments, the method involves first pipetting the liquid carrier (e.g., an aqueous carrier) and/or particles into the particle reservoir prior to pipetting the sample liquid, or a component or concentrate thereof, into the sample reservoir.

The sample reservoir and/or particle reservoir may be incubated in conditions suitable to preserve or promote activity of their contents until the initiation or commencement of droplet formation.

Formation of bioanalyte detection droplets, as provided herein, can be used for various applications. In particular, by forming bioanalyte detection droplets using the methods, devices, systems, and kits herein, a user can perform standard downstream processing methods to barcode heterogeneous populations of cells or perform single-cell nucleic acid sequencing.

In methods of barcoding a population of cells, an aqueous sample having a population of cells is combined with bioanalyte detection particles having a nucleic acid primer sequence and a barcode in an aqueous carrier at an intersection of the sample channel and the particle channel to form a reaction liquid. Upon passing through the droplet formation region, the reaction liquid meets a partitioning liquid (e.g., a partitioning oil) under droplet-forming conditions to form a plurality of reaction droplets, each reaction droplet having one or more of the particles and one or more cells in the reaction liquid. The reaction droplets are incubated under conditions sufficient to allow for barcoding of the nucleic acid of the cells in the reaction droplets. In some embodiments, the conditions sufficient for barcoding are thermally optimized for nucleic acid replication, transcription, and/or amplification. For example, reaction droplets can be incubated at temperatures configured to enable reverse transcription of RNA produced by a cell in a droplet into DNA, using reverse transcriptase. Additionally or alternatively, reaction droplets may be cycled through a series of temperatures to promote amplification, e.g., as in a polymerase chain reaction (PCR). Accordingly, in some embodiments, one or more nucleotide amplification reagents (e.g., PCR reagents) are included in the reaction droplets (e.g., primers, nucleotides, and/or polymerase). Any one or more reagents for nucleic acid replication, transcription, and/or amplification can be provided to the reaction droplet by the aqueous sample, the liquid carrier, or both. In some embodiments, one or more of the reagents for nucleic acid replication, transcription, and/or amplification are in the aqueous sample.

Also provided herein are methods of single-cell nucleic acid sequencing, in which a heterologous population of cells can be characterized by their individual gene expression, e.g., relative to other cells of the population. Methods of barcoding cells discussed above and known in the art can be part of the methods of single-cell nucleic acid sequencing provided herein. After barcoding, nucleic acid transcripts that have been barcoded are sequenced, and sequences can be processed, analyzed, and stored according to known methods. In some embodiments, these methods enable the generation of a genome library containing gene expression data for any single cell within a heterologous population.

Alternatively, the ability to sequester a single cell in a reaction droplet provided by methods herein enables bioanalyte detection for applications beyond genome characterization. For example, a reaction droplet containing a single cell and variety of analyte detection moieties capable of binding different proteins can allow a single cell to be detectably labeled to provide relative protein expression data. In some embodiments, analyte detection moieties are antigen-binding molecules (e.g., antibodies or fragments thereof), wherein each antibody clone is detectably labeled (e.g., with a fluorescent marker having a distinct emission wavelength). Binding of antibodies to proteins can occur within the reaction droplet, and cells can be subsequently analyzed for bound antibodies according to known methods to generate a library of protein expression. Other methods known in the art can be employed to characterize cells within heterologous populations after detecting analytes using the methods provided herein. In one example, following the formation or droplets, subsequent operations that can be performed can include formation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the droplet). An exemplary use for droplets formed using methods of the invention is in performing nucleic acid amplification, e.g., polymerase chain reaction (PCR), where the reagents necessary to carry out the amplification are contained within the first fluid. In the case where a droplet is a droplet in an emulsion, the emulsion can be broken and the contents of the droplet pooled for additional operations. Additional reagents that may be included in a droplet along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of poly-T sequence during sequencing and/or sequence the 5' end of a polynucleotide sequence. The amplification products, for example first amplification products and/or second amplification products, may be subject to sequencing for sequence analysis. In some cases, amplification may be performed using the Partial Hairpin Amplification for Sequencing (PHASE) method.

Methods of Device Manufacture

The microfluidic devices of the present disclosure may be fabricated in any of a variety of conventional ways. For example, in some cases the devices comprise layered structures, where a first layer includes a planar surface into which is disposed a series of channels or grooves that correspond to the channel network in the finished device. A second layer includes a planar surface on one side, and a series of reservoirs defined on the opposing surface, where the reservoirs communicate as passages through to the planar layer, such that when the planar surface of the second layer is mated with the planar surface of the first layer, the reservoirs defined in the second layer are positioned in liquid communication with the termini of the channels on the first layer. Alternatively, both the reservoirs and the connected channels may be fabricated into a single part, where the reservoirs are provided upon a first surface of the structure, with the apertures of the reservoirs extending through to the opposing surface of the structure. The channel network is fabricated as a series of grooves and features in this second surface. A thin laminating layer is then provided over the second surface to seal, and provide the final wall of the channel network, and the bottom surface of the reservoirs.

These layered structures may be fabricated in whole or in part from polymeric materials, such as polyethylene or polyethylene derivatives, such as cyclic olefin copolymers (COC), polymethylmethacrylate (PMMA), polydimethylsiloxane (PDMS), polycarbonate, polystyrene, polypropylene, polyvinyl chloride, polytetrafluoroethylene, polyoxymethylene, polyether ether ketone, polycarbonate, polystyrene, or the like, or they may be fabricated in whole or in part from inorganic materials, such as silicon, or other silica based materials, e.g., glass, quartz, fused silica, borosilicate glass, metals, ceramics, and combinations thereof. Polymeric device components may be fabricated using any of a number of processes including soft lithography, embossing techniques, micromachining, e.g., laser machining, or in some aspects injection molding of the layer components that include the defined channels as well as other structures, e.g., reservoirs, integrated functional components, etc. In some aspects, the structure comprising the reservoirs and channels may be fabricated using, e.g., injection molding techniques to produce polymeric structures. In such cases, a laminating layer may be adhered to the molded structured part through readily available methods, including thermal lamination, solvent based lamination, sonic welding, or the like.

As will be appreciated, structures comprised of inorganic materials also may be fabricated using known techniques. For example, channels and other structures may be micromachined into surfaces or etched into the surfaces using standard photolithographic techniques. In some aspects, the microfluidic devices or components thereof may be fabricated using three-dimensional printing techniques to fabricate the channel or other structures of the devices and/or their discrete components.

Methods for Surface Modifications

The invention features methods for producing a microfluidic device that has a surface modification, e.g., a surface with a modified water contact angle. The methods may be employed to modify the surface of a device such that a liquid can "wet" the surface by altering the contact angle the liquid makes with the surface. An exemplary use of the methods of the invention is in creating a device having differentially coated surfaces to optimize droplet formation.

Devices to be modified with surface coating agents may be primed, e.g., pre-treated, before coating processes occur. In one embodiment, the device has a channel that is in fluid communication with a droplet formation region. In particular, the droplet formation region is configured to allow a liquid exiting the channel to expand in at least one dimension. A surface of the droplet formation region is contacted by at least one reagent that has an affinity for the primed surface to produce a surface having a first water contact angle of greater than about 90°, e.g., a hydrophobic or fluorophillic surface. In certain embodiments, the first contact angle is greater than the water contact angle of the primed surface. In other embodiments, the first contact angle is greater than the water contact angle of the channel surface. Thus, the method allows for the differential coating of surfaces within the microfluidic device.

A surface may be primed by depositing a metal oxide onto it. Example metal oxides useful for priming surfaces include, but are not limited to, $Al_2O_3$, $TiO_2$, $SiO_2$, or a combination thereof. Other metal oxides useful for surface modifications are known in the art. The metal oxide can be applied to the surface by standard deposition techniques, including, but not limited to, atomic layer deposition (ALD), physical vapor deposition (PVD), e.g., sputtering, chemical vapor deposition (CVD), or laser deposition. Other deposition techniques for coating surfaces, e.g., liquid-based deposition, are known in the art. For example, an atomic layer of $Al_2O_3$ can be prepared on a surface by depositing trimethylaluminum (TMA) and water.

In some cases, the coating agent may create a surface that has a water contact angle greater than 90°, e.g., hydrophobic or fluorophillic, or may create a surface with a water contact angle of less than 90°, e.g., hydrophilic. For example, a fluorophillic surface may be created by flowing fluorosilane (e.g., $H_3FSi$) through a primed device surface, e.g., a surface coated in a metal oxide. The priming of the surfaces of the device enhances the adhesion of the coating agents to the surface by providing appropriate surface functional groups. In some cases, the coating agent used to coat the primed surface may be a liquid reagent. For example, when a liquid coating agent is used to coat a surface, the coating agent may be directly introduced to the droplet formation region by a feed channel in fluid communication with the droplet formation region. In order to keep the coating agent localized to the droplet formation region, e.g., prevent ingress of the coating agent to another portion of the device, e.g., the channel, the portion of the device that is not to be coated can be substantially blocked by a substance that does not allow the coating agent to pass. For example, in order to prevent ingress of a liquid coating agent into the channel, the channel may be filled with a blocking liquid that is substantially immiscible with the coating agent. The blocking liquid may be actively transported through the portion of the device not to be coated, or the blocking liquid may be stationary. Alternatively, the channel may be filled with a pressurized gas such that the pressure prevents ingress of the coating agent into the channel. The coating agent may also be applied to the regions of interest external to the main device. For example, the device may incorporate an additional reservoir and at least one feed channel that connects to the region of interest such that no coating agent is passed through the device.

EXAMPLES

Example 1

FIG. 1 shows an example of a microfluidic device for the controlled inclusion of particles, e.g., beads, into discrete droplets. A device 100 can include a channel 102 communicating at a fluidic connection 106 (or intersection) with a reservoir 104. The reservoir 104 can be a chamber. Any reference to "reservoir," as used herein, can also refer to a "chamber." In operation, an aqueous liquid 108 that includes suspended beads 112 may be transported along the channel 102 into the fluidic connection 106 to meet a second liquid 110 that is immiscible with the aqueous liquid 108 in the reservoir 104 to create droplets 116, 118 of the aqueous liquid 108 flowing into the reservoir 104. At the fluidic connection 106 where the aqueous liquid 108 and the second liquid 110 meet, droplets can form based on factors such as the hydrodynamic forces at the fluidic connection 106, flow rates of the two liquids 108, 110, liquid properties, and certain geometric parameters (e.g., w, $h_0$, $\alpha$, etc.) of the device 100. A plurality of droplets can be collected in the reservoir 104 by continuously injecting the aqueous liquid 108 from the channel 102 through the fluidic connection 106.

In some instances, the second liquid 110 may not be subjected to and/or directed to any flow in or out of the reservoir 104. For example, the second liquid 110 may be substantially stationary in the reservoir 104. In some instances, the second liquid 110 may be subjected to flow within the reservoir 104, but not in or out of the reservoir 104, such as via application of pressure to the reservoir 104 and/or as affected by the incoming flow of the aqueous liquid 108 at the fluidic connection 106. Alternatively, the second liquid 110 may be subjected and/or directed to flow in or out of the reservoir 104. For example, the reservoir 104 can be a channel directing the second liquid 110 from upstream to downstream, transporting the generated droplets. Alternatively or in addition, the second liquid 110 in reservoir 104 may be used to sweep formed droplets away from the path of the nascent droplets.

While FIG. 1 illustrates the reservoir 104 having a substantially linear inclination (e.g., creating the expansion angle, a) relative to the channel 102, the inclination may be non-linear. The expansion angle may be an angle between the immediate tangent of a sloping inclination and the channel 102. In an example, the reservoir 104 may have a dome-like (e.g., hemispherical) shape. The reservoir 104 may have any other shape.

Example 2

Figure 2:
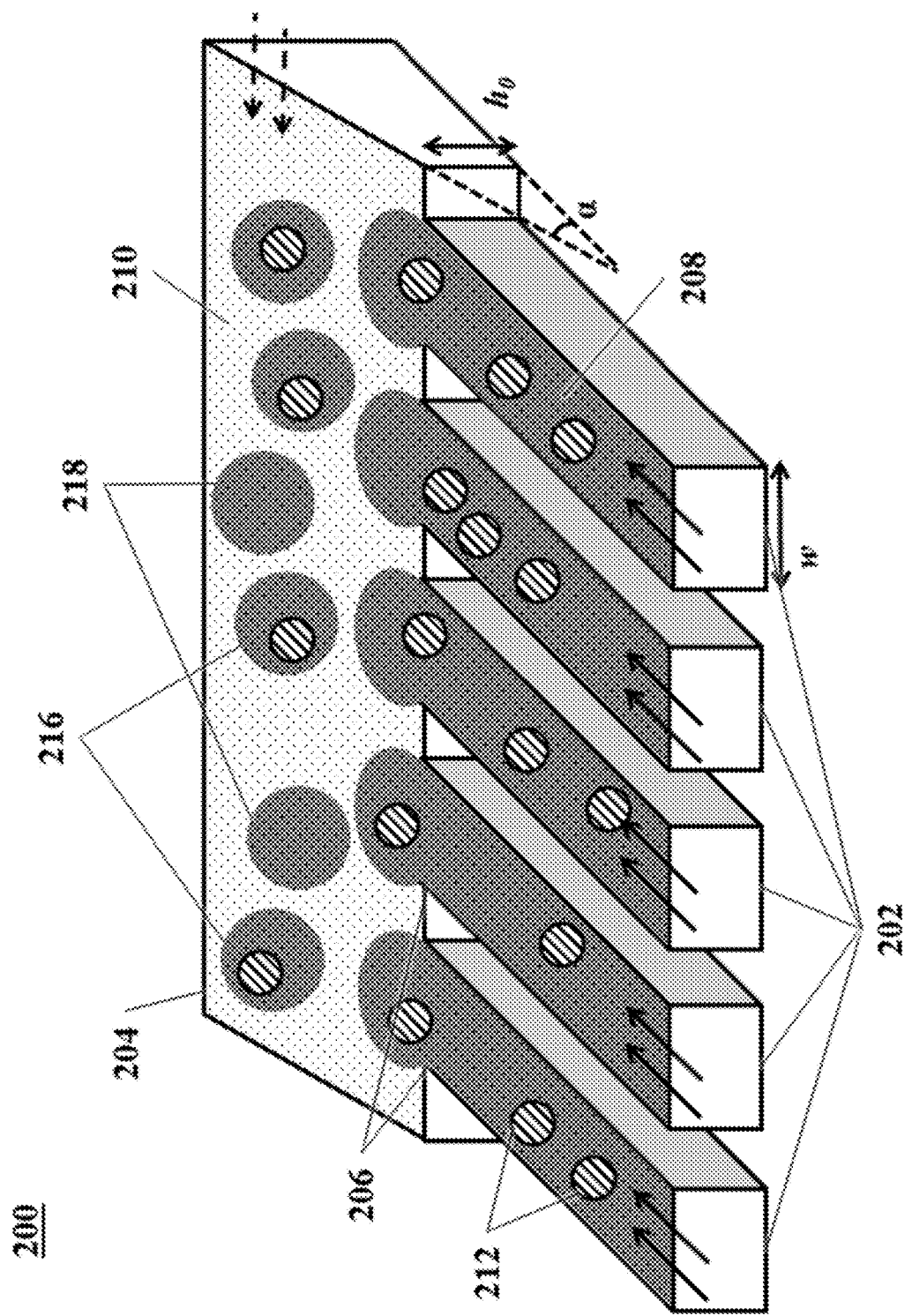
FIG. 2 shows an example of a microfluidic device for increased droplet formation throughput.

FIG. 2 shows an example of a microfluidic device for increased droplet formation throughput. A device 200 can comprise a plurality of channels 202 and a reservoir 204. Each of the plurality of channels 202 may be in fluid communication with the reservoir 204. The device 200 can comprise a plurality of fluidic connections 206 between the plurality of channels 202 and the reservoir 204. Each fluidic connection can be a point of droplet formation. The channel 102 from the device 100 in FIG. 1 and any description to the components thereof may correspond to a given channel of the plurality of channels 202 in device 200 and any description to the corresponding components thereof. The reservoir 104 from the device 100 and any description to the components thereof may correspond to the reservoir 204 from the device 200 and any description to the corresponding components thereof.

Each channel of the plurality of channels 202 may comprise an aqueous liquid 208 that includes suspended particles, e.g., beads, 212. The reservoir 204 may comprise a second liquid 210 that is immiscible with the aqueous liquid 208. In some instances, the second liquid 210 may not be subjected to and/or directed to any flow in or out of the reservoir 204. For example, the second liquid 210 may be substantially stationary in the reservoir 204. Alternatively or in addition, the formed droplets can be moved out of the path of nascent droplets using a gentle flow of the second liquid 210 in the reservoir 204. In some instances, the second liquid 210 may be subjected to flow within the reservoir 204, but not in or out of the reservoir 204, such as via application of pressure to the reservoir 204 and/or as affected by the incoming flow of the aqueous liquid 208 at the fluidic connections. Alternatively, the second liquid 210 may be subjected and/or directed to flow in or out of the reservoir 204. For example, the reservoir 204 can be a channel directing the second liquid 210 from upstream to downstream, transporting the generated droplets. Alternatively or in addition, the second liquid 210 in reservoir 204 may be used to sweep formed droplets away from the path of the nascent droplets.

In operation, the aqueous liquid 208 that includes suspended particles, e.g., beads, 212 may be transported along the plurality of channels 202 into the plurality of fluidic connections 206 to meet the second liquid 210 in the reservoir 204 to create droplets 216, 218. A droplet may form from each channel at each corresponding fluidic connection with the reservoir 204. At the fluidic connection where the aqueous liquid 208 and the second liquid 210 meet, droplets can form based on factors such as the hydrodynamic forces at the fluidic connection, flow rates of the two liquids 208, 210, liquid properties, and certain geometric parameters (e.g., w, $h_0$, $\alpha$, etc.) of the device 200, as described elsewhere herein. A plurality of droplets can be collected in the reservoir 204 by continuously injecting the aqueous liquid 208 from the plurality of channels 202 through the plurality of fluidic connections 206. The geometric parameters, w, $h_0$, and $\alpha$, may or may not be uniform for each of the channels in the plurality of channels 202. For example, each channel may have the same or different widths at or near its respective fluidic connection with the reservoir 204. For example, each channel may have the same or different height at or near its respective fluidic connection with the reservoir 204. In another example, the reservoir 204 may have the same or different expansion angle at the different fluidic connections with the plurality of channels 202. When the geometric parameters are uniform, beneficially, droplet size may also be controlled to be uniform even with the increased throughput. In some instances, when it is desirable to have a different distribution of droplet sizes, the geometric parameters for the plurality of channels 202 may be varied accordingly.

Example 3

Figure 3:
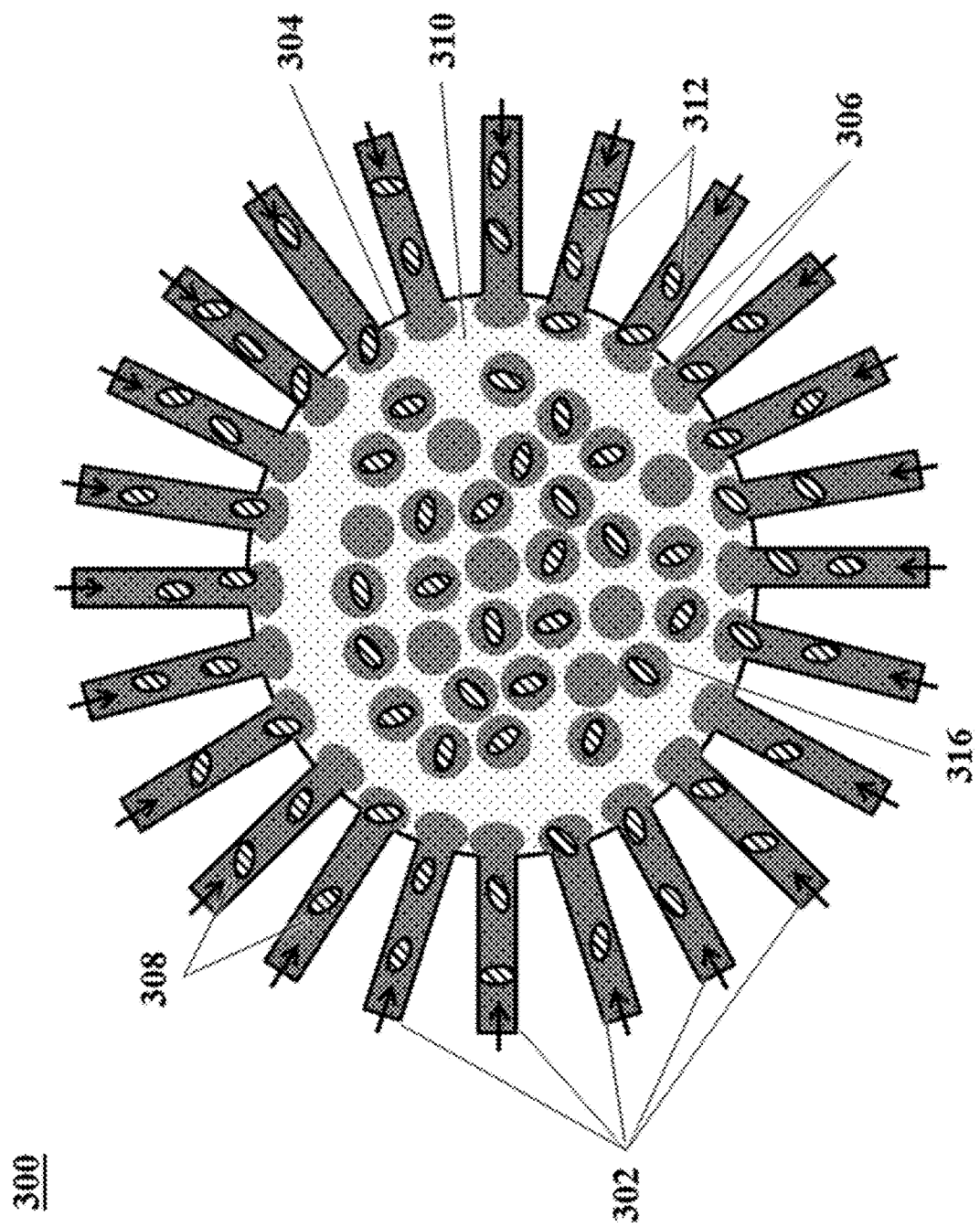
FIG. 3 shows another example of a microfluidic device for increased droplet formation throughput.

FIG. 3 shows another example of a microfluidic device for increased droplet formation throughput. A microfluidic device 300 can comprise a plurality of channels 302 arranged generally circularly around the perimeter of a reservoir 304. Each of the plurality of channels 302 may be in liquid communication with the reservoir 304. The device 300 can comprise a plurality of fluidic connections 306 between the plurality of channels 302 and the reservoir 304. Each fluidic connection can be a point of droplet formation. The channel 102 from the device 100 in FIG. 1 and any description to the components thereof may correspond to a given channel of the plurality of channels 302 in device 300 and any description to the corresponding components thereof. The reservoir 104 from the device 100 and any description to the components thereof may correspond to the reservoir 304 from the device 300 and any description to the corresponding components thereof.

Each channel of the plurality of channels 302 may comprise an aqueous liquid 308 that includes suspended particles, e.g., beads, 312. The reservoir 304 may comprise a second liquid 310 that is immiscible with the aqueous liquid 308. In some instances, the second liquid 310 may not be subjected to and/or directed to any flow in or out of the reservoir 304. For example, the second liquid 310 may be substantially stationary in the reservoir 304. In some instances, the second liquid 310 may be subjected to flow within the reservoir 304, but not in or out of the reservoir 304, such as via application of pressure to the reservoir 304 and/or as affected by the incoming flow of the aqueous liquid 308 at the fluidic connections. Alternatively, the second liquid 310 may be subjected and/or directed to flow in or out of the reservoir 304. For example, the reservoir 304 can be a channel directing the second liquid 310 from upstream to downstream, transporting the generated droplets. Alternatively or in addition, the second liquid 310 in reservoir 304 may be used to sweep formed droplets away from the path of the nascent droplets.

In operation, the aqueous liquid 308 that includes suspended particles, e.g., beads, 312 may be transported along the plurality of channels 302 into the plurality of fluidic connections 306 to meet the second liquid 310 in the reservoir 304 to create a plurality of droplets 316. A droplet may form from each channel at each corresponding fluidic connection with the reservoir 304. At the fluidic connection where the aqueous liquid 308 and the second liquid 310 meet, droplets can form based on factors such as the hydrodynamic forces at the fluidic connection, flow rates of the two liquids 308, 310, liquid properties, and certain geometric parameters (e.g., widths and heights of the channels 302, expansion angle of the reservoir 304, etc.) of the channel, as described elsewhere herein. A plurality of droplets can be collected in the reservoir 304 by continuously injecting the aqueous liquid 308 from the plurality of channels 302 through the plurality of fluidic connections 306.

Example 4

Figure 4:
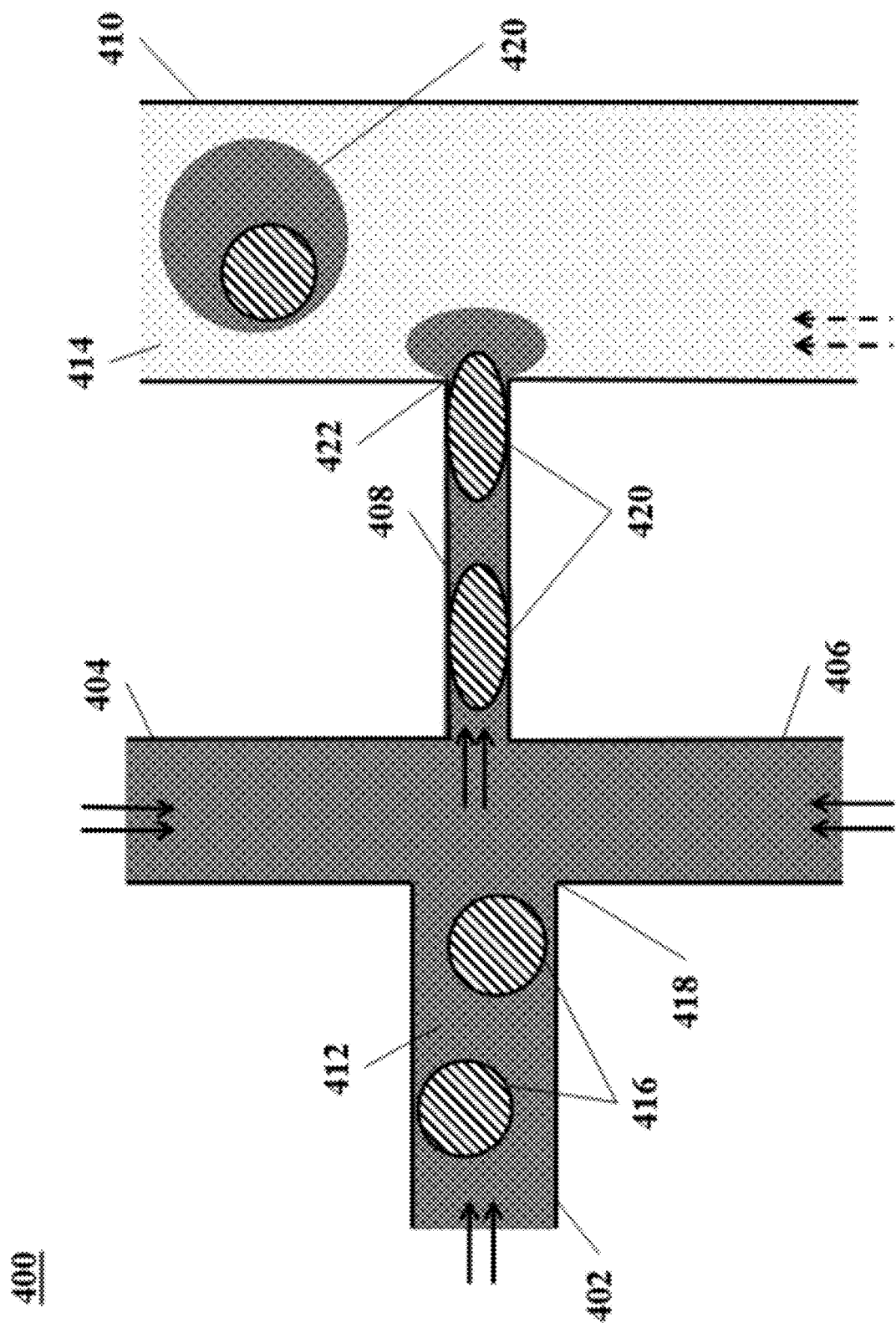
FIG. 4 shows another example of a microfluidic device for the introduction of particles, e.g., beads, into discrete droplets.

FIG. 4 shows another example of a microfluidic device for the introduction of beads into discrete droplets. A device 400 can include a first channel 402, a second channel 404, a third channel 406, a fourth channel 408, and a reservoir 410. The first channel 402, second channel 404, third channel 406, and fourth channel 408 can communicate at a first intersection 418. The fourth channel 408 and the reservoir 410 can communicate at a fluidic connection 422. In some instances, the fourth channel 408 and components thereof can correspond to the channel 102 in the device 100 in FIG. 1 and components thereof. In some instances, the reservoir 410 and components thereof can correspond to the reservoir 104 in the device 100 and components thereof.

In operation, an aqueous liquid 412 that includes suspended particles, e.g., beads, 416 may be transported along the first channel 402 into the intersection 418 at a first frequency to meet another source of the aqueous liquid 412 flowing along the second channel 404 and the third channel 406 towards the intersection 418 at a second frequency. In some instances, the aqueous liquid 412 in the second channel 404 and the third channel 406 may comprise one or more reagents. At the intersection, the combined aqueous liquid 412 carrying the suspended particles, e.g., beads, 416 (and/or the reagents) can be directed into the fourth channel 408. In some instances, a cross-section width or diameter of the fourth channel 408 can be chosen to be less than a cross-section width or diameter of the particles, e.g., beads, 416. In such cases, the particles, e.g., beads, 416 can deform and travel along the fourth channel 408 as deformed particles, e.g., beads, 420 towards the fluidic connection 422. At the fluidic connection 422, the aqueous liquid 412 can meet a second liquid 414 that is immiscible with the aqueous liquid 412 in the reservoir 410 to create droplets 420 of the aqueous liquid 412 flowing into the reservoir 410. Upon leaving the fourth channel 408, the deformed particles, e.g., beads, 420 may revert to their original shape in the droplets 420. At the fluidic connection 422 where the aqueous liquid 412 and the second liquid 414 meet, droplets can form based on factors such as the hydrodynamic forces at the fluidic connection 422, flow rates of the two liquids 412, 414, liquid properties, and certain geometric parameters (e.g., w, $h_0$, α, etc.) of the channel, as described elsewhere herein. A plurality of droplets can be collected in the reservoir 410 by continuously injecting the aqueous liquid 412 from the fourth channel 408 through the fluidic connection 422.

A discrete droplet generated may include a particle, e.g., a bead, (e.g., as in droplets 420). Alternatively, a discrete droplet generated may include more than one particle, e.g., bead. Alternatively, a discrete droplet generated may not include any particles, e.g., beads. In some instances, a discrete droplet generated may contain one or more biological particles, e.g., cells (not shown in FIG. 4).

In some instances, the second liquid 414 may not be subjected to and/or directed to any flow in or out of the reservoir 410. For example, the second liquid 414 may be substantially stationary in the reservoir 410. In some instances, the second liquid 414 may be subjected to flow within the reservoir 410, but not in or out of the reservoir 410, such as via application of pressure to the reservoir 410 and/or as affected by the incoming flow of the aqueous liquid 412 at the fluidic connection 422. In some instances, the second liquid 414 may be gently stirred in the reservoir 410. Alternatively, the second liquid 414 may be subjected and/or directed to flow in or out of the reservoir 410. For example, the reservoir 410 can be a channel directing the second liquid 414 from upstream to downstream, transporting the generated droplets. Alternatively or in addition, the second liquid 414 in reservoir 410 may be used to sweep formed droplets away from the path of the nascent droplets.

Example 5

Figure 5A:
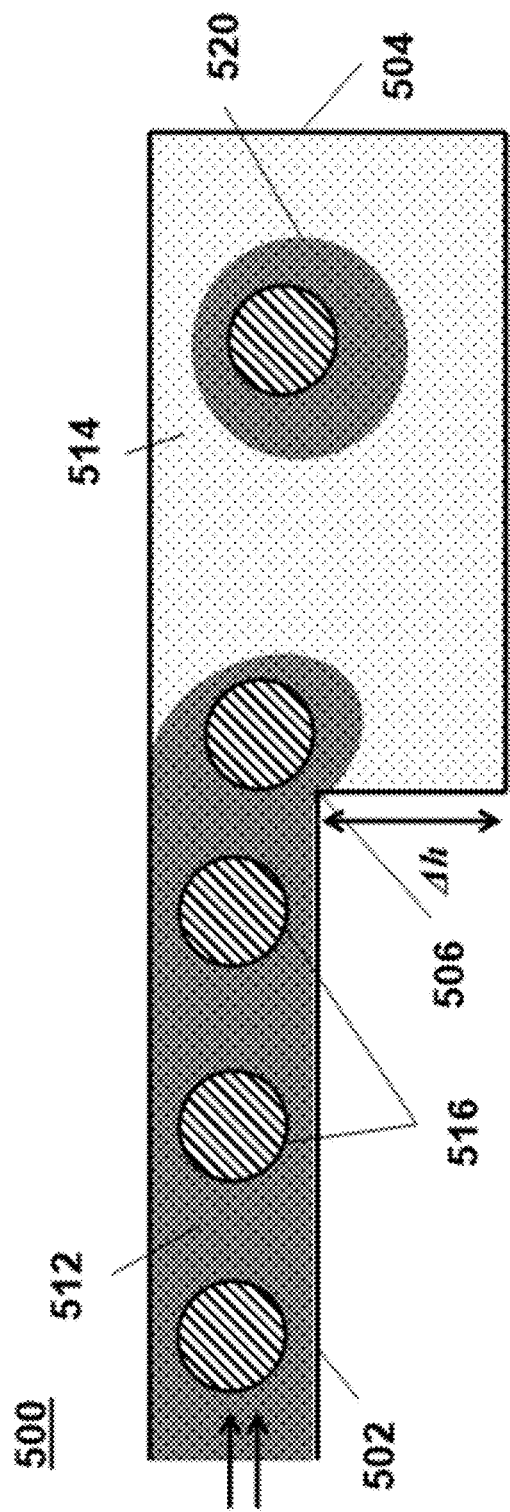
FIGS. 5A-5B show cross-section (FIG. 5A) and perspective (FIG. 5B) views an embodiment according to the invention of a microfluidic device with a geometric feature for droplet formation.
Figure 5B:
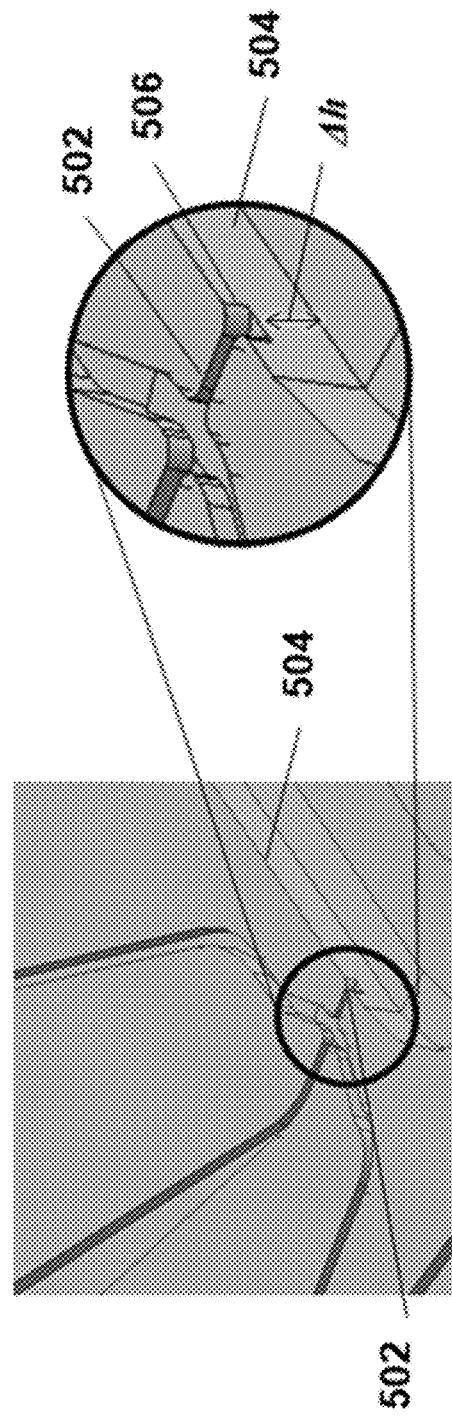

FIG. 5A shows a cross-section view of another example of a microfluidic device with a geometric feature for droplet formation. A device 500 can include a channel 502 communicating at a fluidic connection 506 (or intersection) with a reservoir 504. In some instances, the device 500 and one or more of its components can correspond to the device 100 and one or more of its components. FIG. 5B shows a perspective view of the device 500 of FIG. 5A.

An aqueous liquid 512 comprising a plurality of particles 516 may be transported along the channel 502 into the fluidic connection 506 to meet a second liquid 514 (e.g., oil, etc.) that is immiscible with the aqueous liquid 512 in the reservoir 504 to create droplets 520 of the aqueous liquid 512 flowing into the reservoir 504. At the fluidic connection 506 where the aqueous liquid 512 and the second liquid 514 meet, droplets can form based on factors such as the hydrodynamic forces at the fluidic connection 506, relative flow rates of the two liquids 512, 514, liquid properties, and certain geometric parameters (e.g., Δh, etc.) of the device 500. A plurality of droplets can be collected in the reservoir 504 by continuously injecting the aqueous liquid 512 from the channel 502 at the fluidic connection 506.

While FIGS. 5A and 5B illustrate the height difference, Δh, being abrupt at the fluidic connection 506 (e.g., a step increase), the height difference may increase gradually (e.g., from about 0 µm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the fluidic connection 506, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly.

Example 6

FIGS. 6A and 6B show a cross-section view and a top view, respectively, of another example of a microfluidic device with a geometric feature for droplet formation. A device 600 can include a channel 602 communicating at a fluidic connection 606 (or intersection) with a reservoir 604. In some instances, the device 600 and one or more of its components can correspond to the device 500 and one or more of its components.

An aqueous liquid 612 comprising a plurality of particles 616 may be transported along the channel 602 into the fluidic connection 606 to meet a second liquid 614 (e.g., oil, etc.) that is immiscible with the aqueous liquid 612 in the reservoir 604 to create droplets 620 of the aqueous liquid 612 flowing into the reservoir 604. At the fluidic connection 606 where the aqueous liquid 612 and the second liquid 614 meet, droplets can form based on factors such as the hydrodynamic forces at the fluidic connection 606, relative flow rates of the two liquids 612, 614, liquid properties, and certain geometric parameters (e.g., Δh, ledge, etc.) of the channel 602. A plurality of droplets can be collected in the reservoir 604 by continuously injecting the aqueous liquid 612 from the channel 602 at the fluidic connection 606.

The aqueous liquid may comprise particles. The particles 616 (e.g., beads) can be introduced into the channel 602 from a separate channel (not shown in FIG. 6). In some instances, the particles 616 can be introduced into the channel 602 from a plurality of different channels, and the frequency controlled accordingly. In some instances, different particles may be introduced via separate channels. For example, a first separate channel can introduce beads and a second separate channel can introduce biological particles into the channel 602. The first separate channel introducing the beads may be upstream or downstream of the second separate channel introducing the biological particles.

While FIGS. 6A and 6B illustrate one ledge (e.g., step) in the reservoir 604, as can be appreciated, there may be a plurality of ledges in the reservoir 604, for example, each having a different cross-section height. For example, where there is a plurality of ledges, the respective cross-section height can increase with each consecutive ledge. Alternatively, the respective cross-section height can decrease and/or increase in other patterns or profiles (e.g., increase then decrease then increase again, increase then increase then increase, etc.).

While FIGS. 6A and 6B illustrate the height difference, Δh, being abrupt at the ledge 608 (e.g., a step increase), the height difference may increase gradually (e.g., from about 0 µm to a maximum height difference). In some instances, the height difference may decrease gradually (e.g., taper) from a maximum height difference. In some instances, the height difference may variably increase and/or decrease linearly or non-linearly. The same may apply to a height difference, if any, between the first cross-section and the second cross-section.

Example 7

FIGS. 7A and 7B show a cross-section view and a top view, respectively, of another example of a microfluidic device with a geometric feature for droplet formation. A device 700 can include a channel 702 communicating at a fluidic connection 706 (or intersection) with a reservoir 704. In some instances, the device 700 and one or more of its components can correspond to the device 600 and one or more of its components.

An aqueous liquid 712 comprising a plurality of particles 716 may be transported along the channel 702 into the fluidic connection 706 to meet a second liquid 714 (e.g., oil, etc.) that is immiscible with the aqueous liquid 712 in the reservoir 704 to create droplets 720 of the aqueous liquid 712 flowing into the reservoir 704. At the fluidic connection 706 where the aqueous liquid 712 and the second liquid 714 meet, droplets can form based on factors such as the hydrodynamic forces at the fluidic connection 706, relative flow rates of the two liquids 712, 714, liquid properties, and certain geometric parameters (e.g., Δh, etc.) of the device 700. A plurality of droplets can be collected in the reservoir 704 by continuously injecting the aqueous liquid 712 from the channel 702 at the fluidic connection 706.

In some instances, the second liquid 714 may not be subjected to and/or directed to any flow in or out of the reservoir 704. For example, the second liquid 714 may be substantially stationary in the reservoir 704. In some instances, the second liquid 714 may be subjected to flow within the reservoir 704, but not in or out of the reservoir 704, such as via application of pressure to the reservoir 704 and/or as affected by the incoming flow of the aqueous liquid 712 at the fluidic connection 706. Alternatively, the second liquid 714 may be subjected and/or directed to flow in or out of the reservoir 704. For example, the reservoir 704 can be a channel directing the second liquid 714 from upstream to downstream, transporting the generated droplets. Alternatively or in addition, the second liquid 714 in reservoir 704 may be used to sweep formed droplets away from the path of the nascent droplets.

The device 700 at or near the fluidic connection 706 may have certain geometric features that at least partly determine the sizes and/or shapes of the droplets formed by the device 700. The channel 702 can have a first cross-section height, $h_1$, and the reservoir 704 can have a second cross-section height, $h_2$. The first cross-section height, $h_1$, may be different from the second cross-section height $h_2$ such that at or near the fluidic connection 706, there is a height difference of Δh. The second cross-section height, $h_2$, may be greater than the first cross-section height, $h_1$. The reservoir may thereafter gradually increase in cross-section height, for example, the more distant it is from the fluidic connection 706. In some instances, the cross-section height of the reservoir may increase in accordance with expansion angle, β, at or near the fluidic connection 706. The height difference, Δh, and/or expansion angle, β, can allow the tongue (portion of the aqueous liquid 712 leaving channel 702 at fluidic connection 706 and entering the reservoir 704 before droplet formation) to increase in depth and facilitate decrease in curvature of the intermediately formed droplet. For example, droplet size may decrease with increasing height difference and/or increasing expansion angle.

While FIGS. 7A and 7B illustrate the height difference, Δh, being abrupt at the fluidic connection 706, the height difference may increase gradually (e.g., from about 0 μm to a maximum height difference). In some instances, the height difference may decrease gradually (e.g., taper) from a maximum height difference. In some instances, the height difference may variably increase and/or decrease linearly or non-linearly. While FIGS. 7A and 7B illustrate the expanding reservoir cross-section height as linear (e.g., constant expansion angle, β), the cross-section height may expand non-linearly. For example, the reservoir may be defined at least partially by a dome-like (e.g., hemispherical) shape having variable expansion angles. The cross-section height may expand in any shape.

Example 8

FIGS. 8A and 8B show a cross-section view and a top view, respectively, of another example of a microfluidic device with a geometric feature for droplet formation. A device 800 can include a channel 802 communicating at a fluidic connection 806 (or intersection) with a reservoir 804. In some instances, the device 800 and one or more of its components can correspond to the device 700 and one or more of its components and/or correspond to the device 600 and one or more of its components.

An aqueous liquid 812 comprising a plurality of particles 816 may be transported along the channel 802 into the fluidic connection 806 to meet a second liquid 814 (e.g., oil, etc.) that is immiscible with the aqueous liquid 812 in the reservoir 804 to create droplets 820 of the aqueous liquid 812 flowing into the reservoir 804. At the fluidic connection 806 where the aqueous liquid 812 and the second liquid 814 meet, droplets can form based on factors such as the hydrodynamic forces at the fluidic connection 806, relative flow rates of the two liquids 812, 814, liquid properties, and certain geometric parameters (e.g., Δh, etc.) of the device 800. A plurality of droplets can be collected in the reservoir 804 by continuously injecting the aqueous liquid 812 from the channel 802 at the fluidic connection 806.

A discrete droplet generated may comprise one or more particles of the plurality of particles 816. As described elsewhere herein, a particle may be any particle, such as a bead, cell bead, gel bead, biological particle, macromolecular constituents of biological particle, or other particles. Alternatively, a discrete droplet generated may not include any particles.

In some instances, the second liquid 814 may not be subjected to and/or directed to any flow in or out of the reservoir 804. For example, the second liquid 814 may be substantially stationary in the reservoir 804. In some instances, the second liquid 814 may be subjected to flow within the reservoir 804, but not in or out of the reservoir 804, such as via application of pressure to the reservoir 804 and/or as affected by the incoming flow of the aqueous liquid 812 at the fluidic connection 806. Alternatively, the second liquid 814 may be subjected and/or directed to flow in or out of the reservoir 804. For example, the reservoir 804 can be a channel directing the second liquid 814 from upstream to downstream, transporting the generated droplets. Alternatively or in addition, the second liquid 814 in reservoir 804 may be used to sweep formed droplets away from the path of the nascent droplets.

While FIGS. 8A and 8B illustrate one ledge (e.g., step) in the reservoir 804, as can be appreciated, there may be a plurality of ledges in the reservoir 804, for example, each having a different cross-section height. For example, where there is a plurality of ledges, the respective cross-section height can increase with each consecutive ledge. Alternatively, the respective cross-section height can decrease and/ or increase in other patterns or profiles (e.g., increase then decrease then increase again, increase then increase then increase, etc.).

While FIGS. 8A and 8B illustrate the height difference, Δh, being abrupt at the ledge 808, the height difference may increase gradually (e.g., from about 0 μm to a maximum height difference). In some instances, the height difference may decrease gradually (e.g., taper) from a maximum height difference. In some instances, the height difference may variably increase and/or decrease linearly or non-linearly. While FIGS. 8A and 8B illustrate the expanding reservoir cross-section height as linear (e.g., constant expansion angle), the cross-section height may expand non-linearly. For example, the reservoir may be defined at least partially by a dome-like (e.g., hemispherical) shape having variable expansion angles. The cross-section height may expand in any shape.

Example 9

Figure 9A:
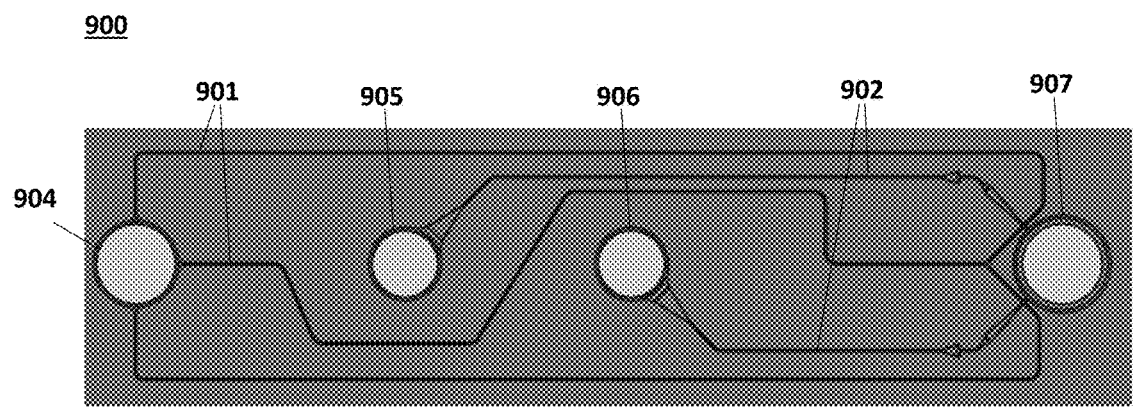
FIGS. 9A-9B are views of another device of the invention.
Figure 9B:
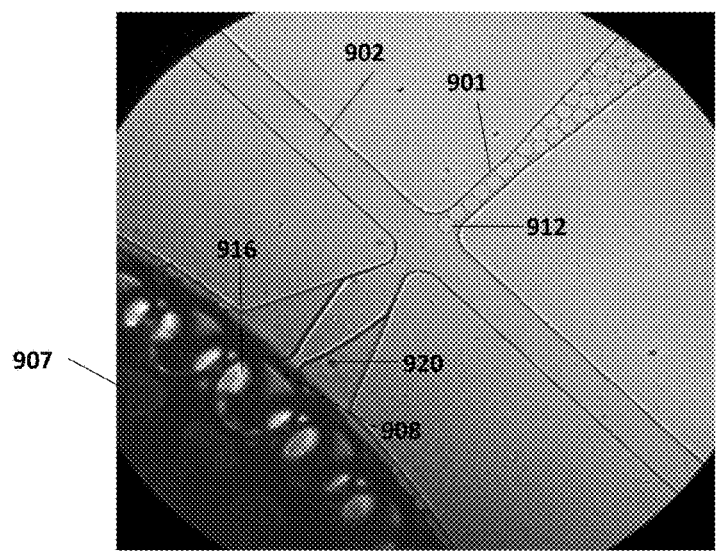

An example of a device according to the invention is shown in FIGS. 9A-9B. The device 900 includes four fluid reservoirs, 904, 905, 906, and 907, respectively. Reservoir 904 houses one liquid; reservoirs 905 and 906 house another liquid, and reservoir 907 houses continuous phase in the step region 908. This device 900 include two first channels 902 connected to reservoir 905 and reservoir 906 and connected to a shelf region 920 adjacent a step region 908. As shown, multiple channels 901 from reservoir 904 deliver additional liquid to the first channels 902. The liquids from reservoir 904 and reservoir 905 or 906 combine in the first channel 902 forming the first liquid that is dispersed into the continuous phase as droplets. In certain embodiments, the liquid in reservoir 905 and/or reservoir 906 includes a particle, such as a gel bead. FIG. 9B shows a view of the first channel 902 containing gel beads intersected by a second channel 901 adjacent to a shelf region 920 leading to a step region 908, which contains multiple droplets 916.

Example 10

Figure 10A:
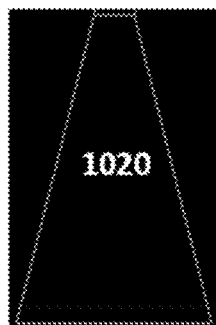
FIGS. 10A-10E are views of droplet formation regions including shelf regions.
Figure 10B:
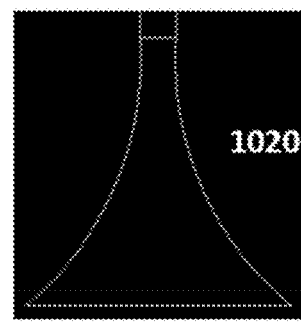
Figure 10C:
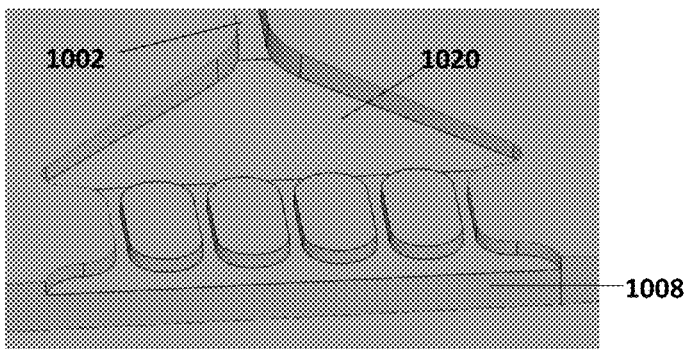
Figure 10D:
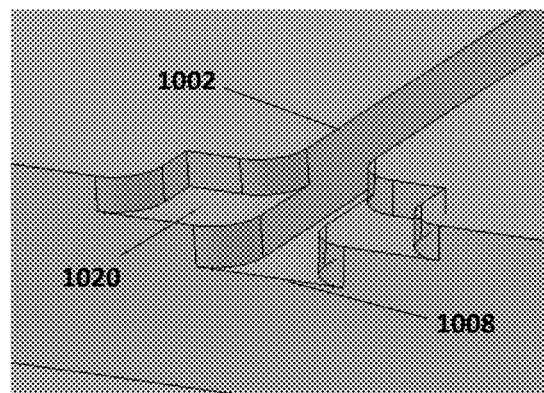
Figure 10E:
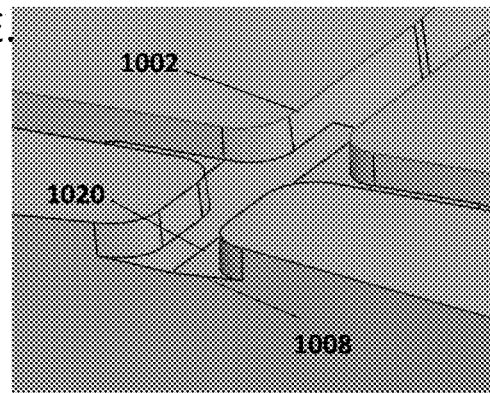
Figure 11A:
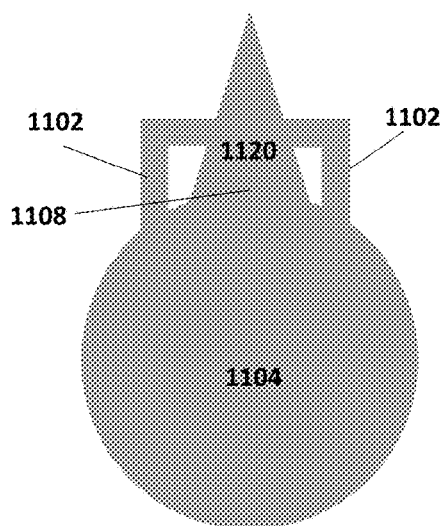
FIGS. 11A-11D are views of droplet formation regions including shelf regions including additional channels to deliver continuous phase.
Figure 11B:
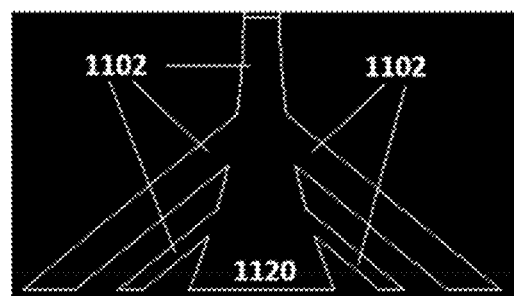
Figure 11C:
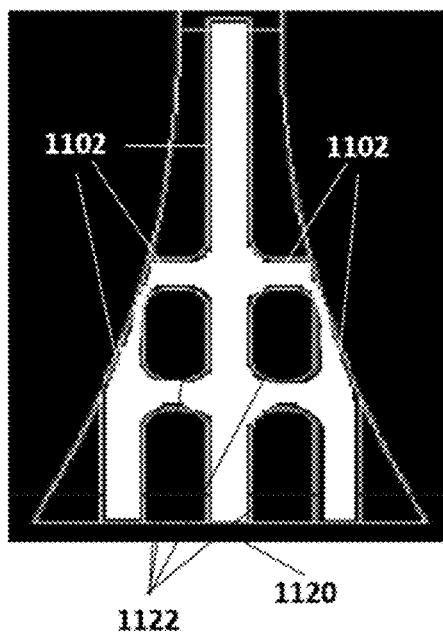
Figure 11D:
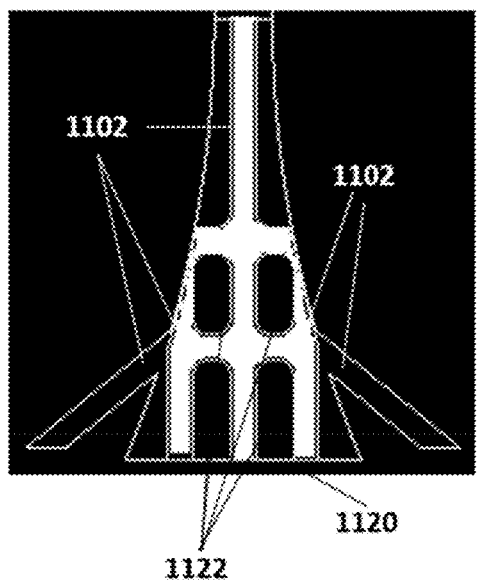

Variations on shelf regions 1020 are shown in FIGS. 10A-10E. As shown in FIGS. 10A-10B, the width of the shelf region 1020 can increase from the distal end of a first channel 1002 towards the step region 1008, linearly as in 10A or non-linearly as in 10B. As shown in FIG. 10C, multiple first channels 1002 can branch from a single feed channel 1002 and introduce fluid into interconnected shelf regions 1020. As shown in FIG. 10D, the depth of the first channel 1002 may be greater than the depth of the shelf region 1020 and cut a path through the shelf region 1020. As shown in FIG. 10E, the first channel 1002 and shelf region 1020 may contain a grooved bottom surface. This device 1000 also includes a second channel 1002 that intersects the first channel 1002 proximal to its distal end.

Example 11

Continuous phase delivery channels 1102, shown in FIGS. 11A-11D, are variations on shelf regions 1120 including channels 1102 for delivery (passive or active) of continuous phase behind a nascent droplet. In one example in FIG. 11A, the device 1100 includes two channels 1102 that connect the reservoir 1104 of the step region 1108 to either side of the shelf region 1120. In another example in FIG. 11B, four channels 1102 provide continuous phase to the shelf region 1120. These channels 1102 can be connected to the reservoir 1104 of the step region 1108 or to a separate source of continuous phase. In a further example in FIG. 11C, the shelf region 1120 includes one or more channels 1102 (white) below the depth of the first channel 1102 (black) that connect to the reservoir 1104 of the step region 1108. The shelf region 1120 contains islands 1122 in black. In another example FIG. 11D, the shelf region 1120 of FIG. 11C includes two additional channels 1102 for delivery of continuous phase on either side of the shelf region 1120.

Example 12

Figure 12:
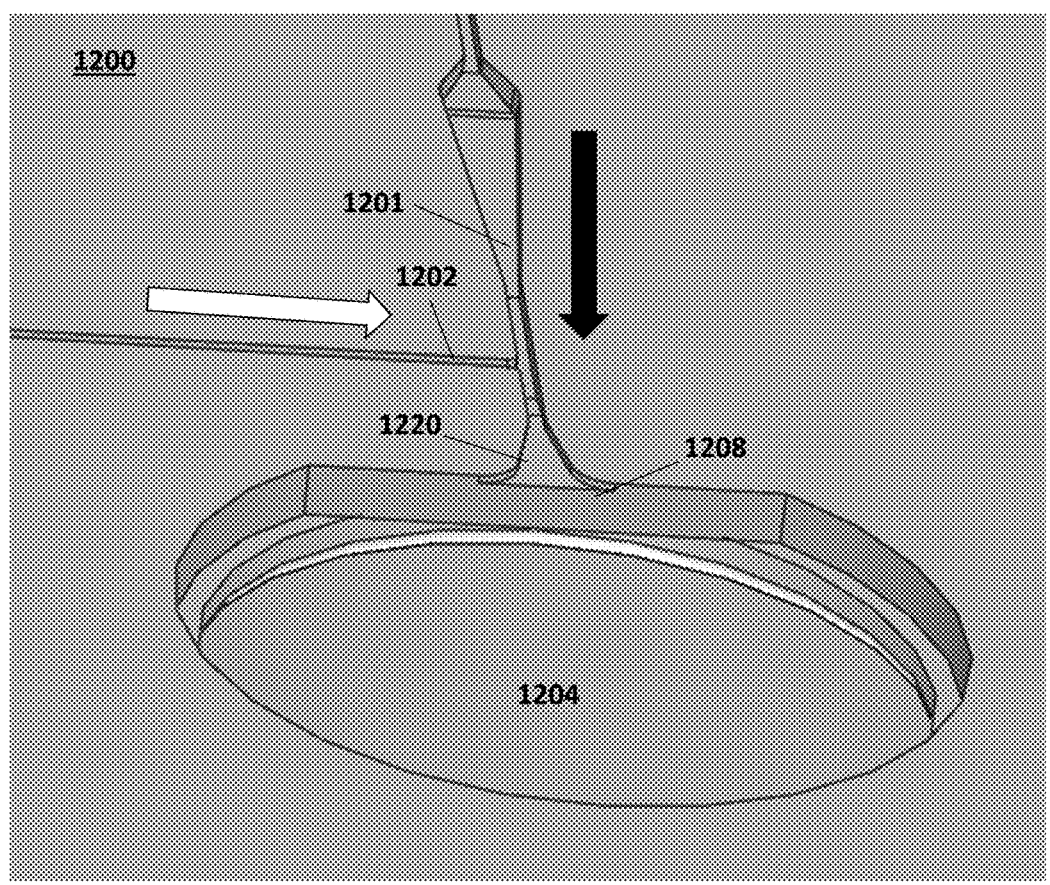
FIG. 12 is another device according to the invention having a pair of intersecting channels that lead to a droplet formation region and collection reservoir.

An embodiment of a device according to the invention is shown in FIG. 12. This device 1200 includes two channels 1201, 1202 that intersect upstream of a droplet formation region. The droplet formation region includes both a shelf region 1220 and a step region 1208 disposed between the distal end of the first channel 1201 and the step region 1208 that lead to a collection reservoir 1204. The black and white arrows show the flow of liquids through each of first channel 1201 and second channel 1202, respectively. In certain embodiments, the liquid flowing through the first channel 1201 or second channel 1202 includes a particle, such as a gel bead. As shown in the FIG. 12, the width of the shelf region 1220 can increase from the distal end of a first channel 1201 towards the step region 1208; in particular, the width of the shelf region 1220 in FIG. 12 increases non-linearly. In this embodiment, the shelf region extends from the edge of a reservoir to allow droplet formation away from the edge. Such a geometry allows droplets to move away from the droplet formation region due to differential density between the continuous and dispersed phase.

Example 13

Figure 13A:
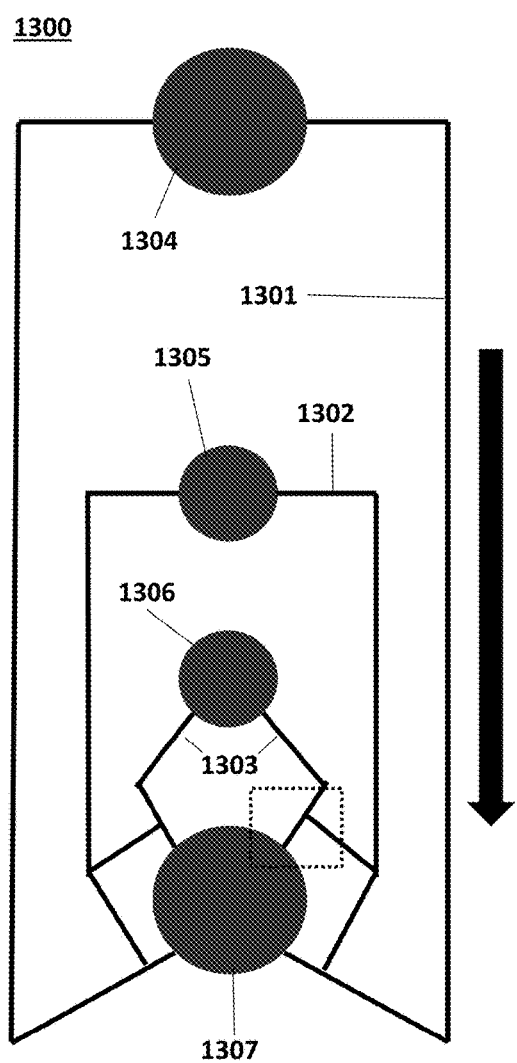
FIGS. 13A-13B are views of a device of the invention.
Figure 13B:
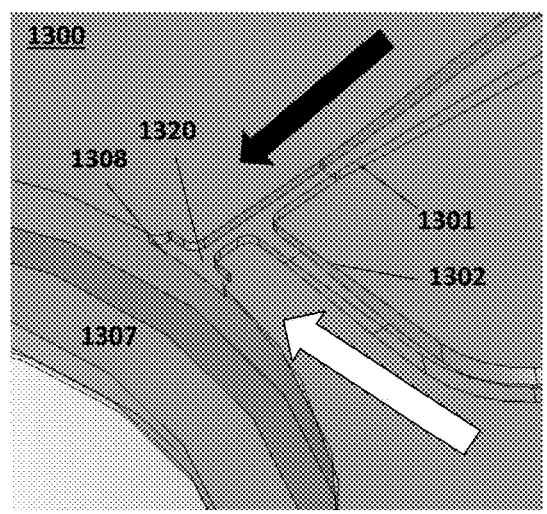

An embodiment of a device according to the invention for multiplexed droplet formation is shown in FIGS. 13A-13B. This device 1300 includes four fluid reservoirs, 1304, 1305, 1306, and 1307, and the overall direction of flow within the device 1300 is shown by the black arrow in FIG. 13A. Reservoir 1304 and reservoir 1306 house one liquid; reservoir 1305 houses another liquid, and reservoir 1307 houses continuous phase and is a collection reservoir. Fluid channels 1301, 1303 directly connect reservoir 1304 and reservoir 1306, respectively, to reservoir 1307; thus, there are four droplet formation region in this device 1300. Each droplet formation region has a shelf region 1320 and a step region 1308. This device 1300 further has two channels 1302 from the reservoir 1305 where each of these channels splits into two separate channels at their distal ends. Each of the branches of the split channel intersects the first channels 1301 or 1303 upstream of their connection to the collection reservoir 1307. As shown in the zoomed in view of the dotted line box in FIG. 13B, second channel 1302, with its flow indicated by the white arrow, has its distal end intersecting a channel 1303 from reservoir 1305, with the flow of the channel indicated by the black arrow, upstream of the droplet formation region. The liquid from reservoir 1304 and reservoir 1306, separately, are introduced into channels 1301, 1303 and flow towards the collection reservoir 1307. The liquid from the second reservoir 1305 combines with the fluid from reservoir 1304 or reservoir 1306, and the combined fluid is dispersed into the droplet formation region and to the continuous phase. In certain embodiments, the liquid flowing through the first channel 1301 or 1303 or second channel 1302 includes a particle, such as a gel bead.

Example 14

Figure 14A:
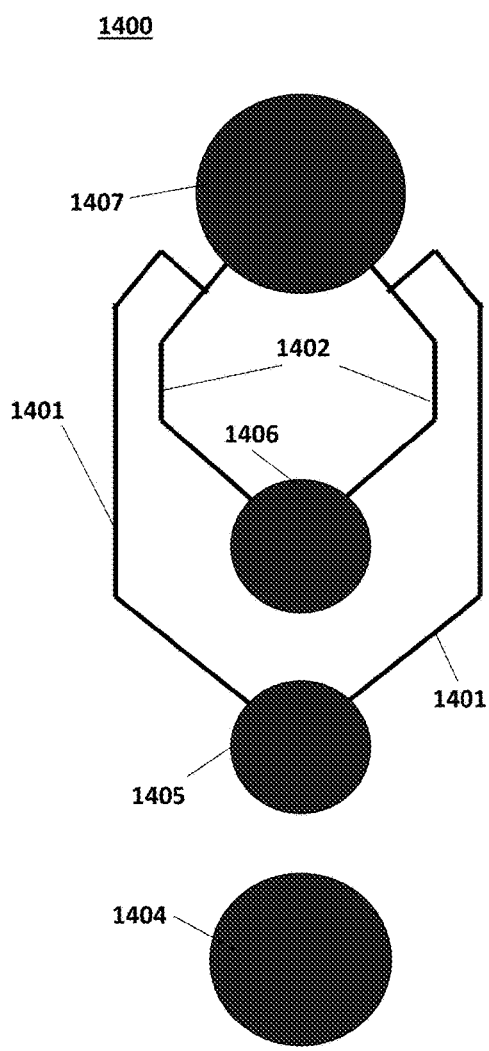
FIGS. 14A-14B are views of devices according to the invention.
Figure 14B:
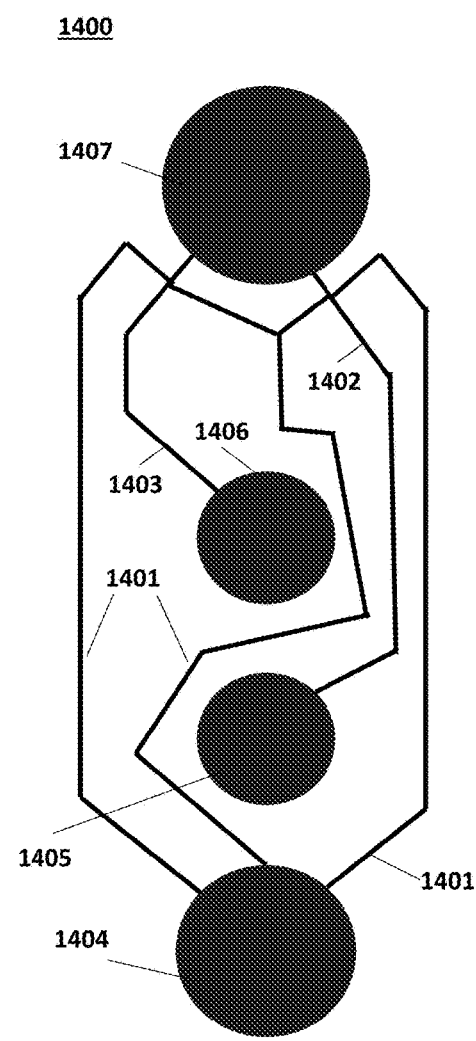

Examples of devices according to the invention that include two droplet formation regions are shown in FIGS. 14A-14B. The device 1400 of FIG. 14A includes three reservoirs, 1405, 1406, and 1407, and the device 1400 of FIG. 14B includes four reservoirs, 1404, 1405, 1406, and 1407. For the device 1400 of FIG. 14A, reservoir 1405 houses a portion of the first fluid, reservoir 1406 houses a different portion of the first fluid, and reservoir 1407 houses continuous phase and is a collection reservoir. In the device 1400 of FIG. 14B, reservoir 1404 houses a portion of the first fluid, reservoir 1405 and reservoir 1406 house different portions of the first fluid, and reservoir 1407 houses continuous phase and is a collection reservoir. In both devices 1400, there are two droplet formation regions. For the device 1400 of FIG. 14A, the connections to the collection reservoir 1407 are from the reservoir 1406, and the distal ends of the channels 1401 from reservoir 1405 intersect the channels 1402 from reservoir 1406 upstream of the droplet formation region. The liquids from reservoir 1405 and reservoir 1406 combine in the channels 1402 from reservoir 1406, forming the first liquid that is dispersed into the continuous phase in the collection reservoir 1407 as droplets. In certain embodiments, the liquid in reservoir 1405 and/or reservoir 1406 includes a particle, such as a gel bead.

In the device 1400 of FIG. 14B, each of reservoir 1405 and reservoir 1406 are connected to the collection reservoir 1407. Reservoir 1404 has three channels 1401, two of which have distal ends that intersect each of the channels 1402, 1403 from reservoir 1404 and reservoir 1406, respectively, upstream of the droplet formation region. The third channel 1401 from reservoir 1404 splits into two separate distal ends, with one end intersecting the channel 1402 from reservoir 1405 and the other distal end intersecting the channel 1403 from reservoir 1406, both upstream of droplet formation regions. The liquid from reservoir 1404 combines with the liquids from reservoir 1405 and reservoir 1406 in the channels 1402 from reservoir 1405 and reservoir 1406, forming the first liquid that is dispersed into the continuous phase in the collection reservoir 1407 as droplets. In certain embodiments, the liquid in reservoir 1404, reservoir 1405, and/or reservoir 1406 includes a particle, such as a gel bead.

Example 15

Figure 15:
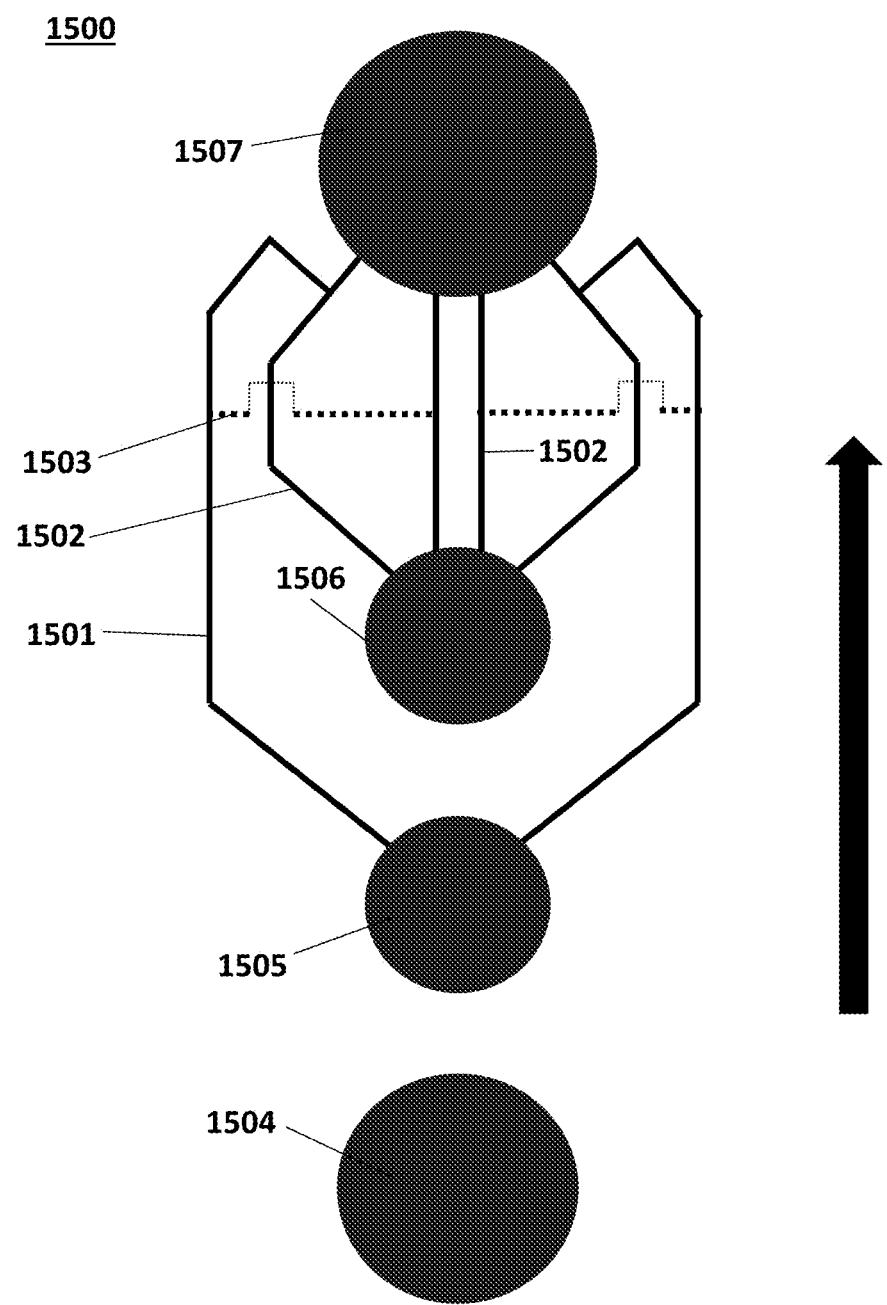
FIG. 15 is a view of a device according to the invention with four reservoirs.

An embodiment of a device according to the invention that has four droplet formation regions is shown in FIG. 15. The device 1500 of FIG. 15 includes four reservoirs, 1504, 1505, 1506, and 1507; the reservoir labeled 1504 is unused in this embodiment. In the device 1500 of FIG. 15, reservoir 1505 houses a portion of the first fluid, reservoir 1506 houses a different portion of the first fluid, and reservoir 1507 houses continuous phase and is a collection reservoir. Reservoir 1506 has four channels 1502 that connect to the collection reservoir 1507 at four droplet formation regions. The channels 1502 from originating at reservoir 1506 include two outer channels 1502 and two inner channels 1502. Reservoir 1505 has two channels 1501 that intersect the two outer channels 1502 from reservoir 1506 upstream of the droplet formation regions. Channels 1501 and the inner channels 1502 are connected by two channels 1503 that traverse, but do not intersect, the fluid paths of the two outer channels 1502. These connecting channels 1503 from channels 1501 pass over the outer channels 1502 and intersect the inner channels 1502 upstream of the droplet formation regions. The liquids from reservoir 1505 and reservoir 1506 combine in the channels 1502, forming the first liquid that is dispersed into the continuous phase in the collection reservoir 1507 as droplets. In certain embodiments, the liquid in reservoir 1505 and/or reservoir 1506 includes a particle, such as a gel bead.

Example 16

Figure 16A:
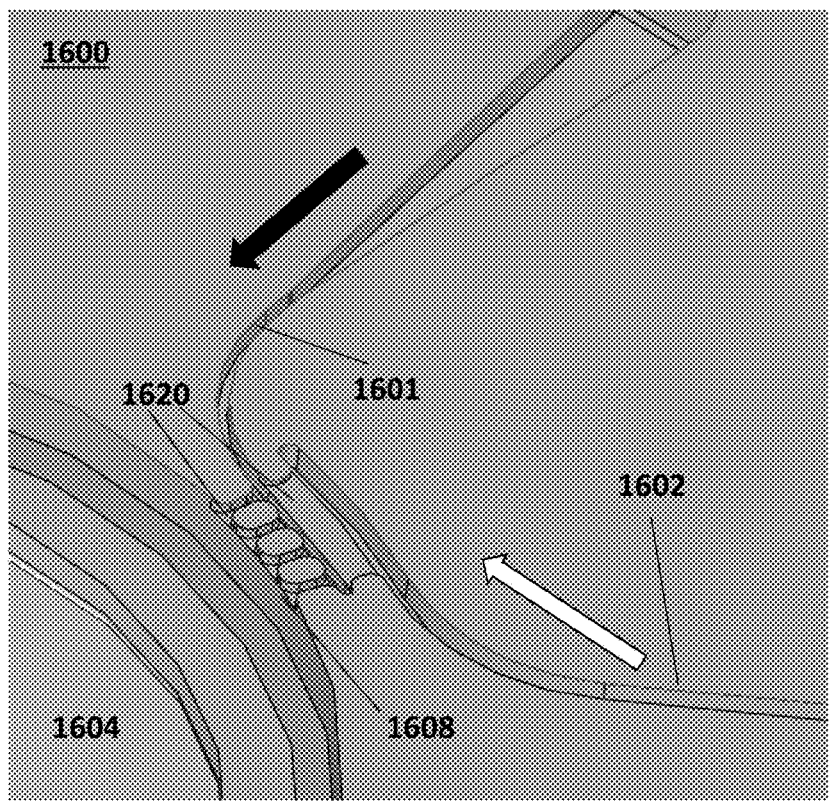
FIGS. 16A-16B are views of an embodiment according to the invention.
Figure 16B:
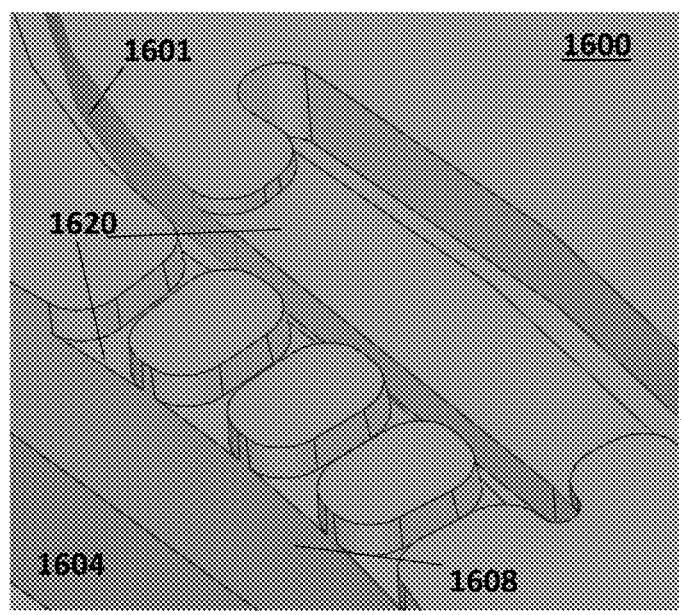

An embodiment of a device according to the invention that has a plurality of droplet formation regions is shown in FIGS. 16A-16B (FIG. 16B is a zoomed in view of FIG. 16A), with the droplet formation region including a shelf region 1620 and a step region 1608. This device 1600 includes two channels 1601, 1602 that meet at the shelf region 1620. As shown, after the two channels 1601, 1602 meet at the shelf region 1620, the combination of liquids is divided, in this example, by four shelf regions. In certain embodiments, the liquid with flow indicated by the black arrow includes a particle, such as a gel bead, and the liquid flow from the other channel, indicated by the white arrow, can move the particles into the shelf regions such that each particle can be introduced into a droplet.

Example 17

Figure 17A:
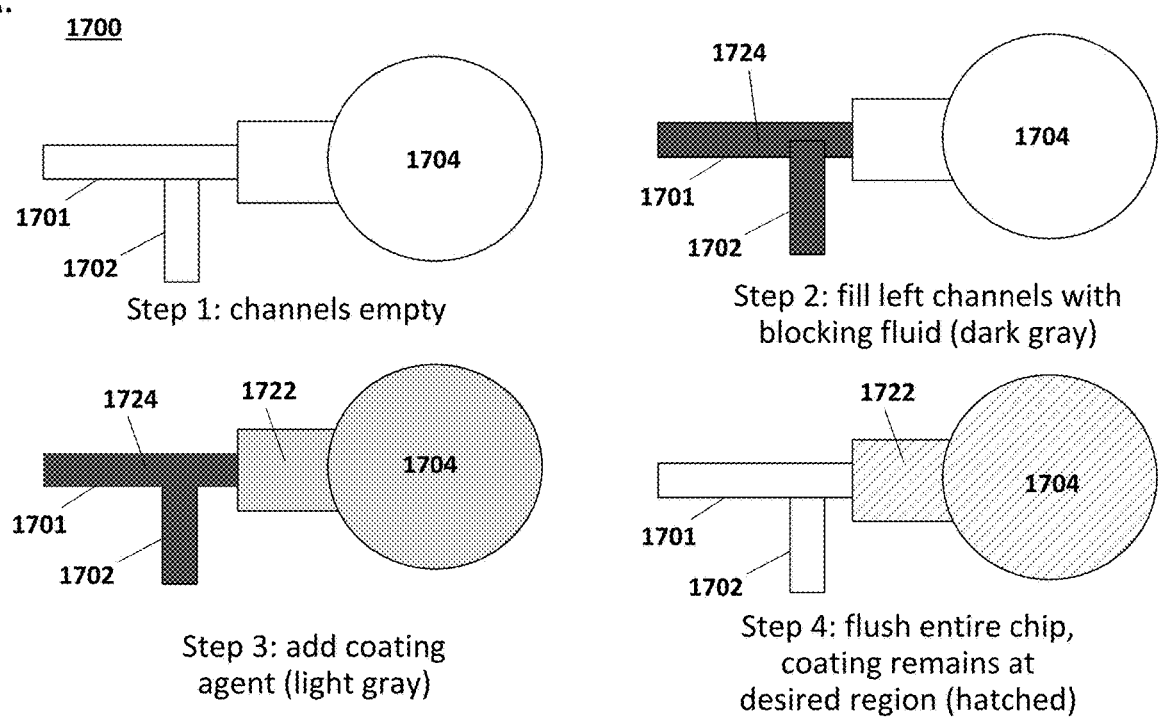
FIGS. 17A-17B are schematic representations of a method according to the invention for applying a differential coating to a surface of a device of the invention.
Figure 17B:
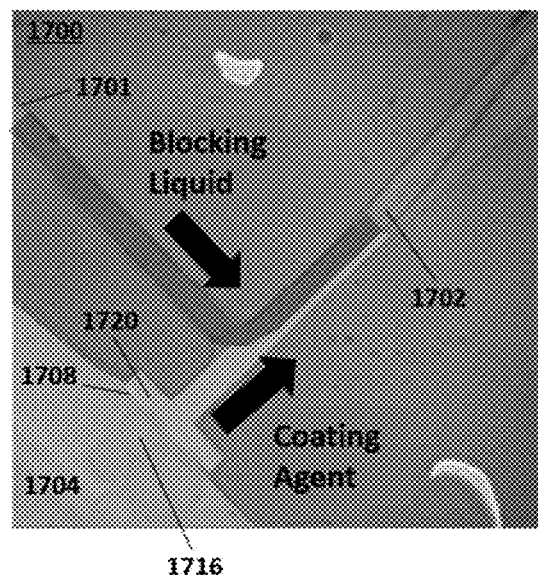

An embodiment of a method of modifying the surface of a device using a coating agent is shown in FIGS. 17A-17B. In this example, the surface of the droplet formation region of the device 1700, e.g., the rectangular area connected to the circular shaped collection reservoir 1704, is coated with a coating agent 1722 to modify its surface properties. To localize the coating agent to only the regions of interest, the first channel 1701 and second channel 1702 of the device 1700 are filled with a blocking liquid 1724 (Step 2 of FIG. 17A) such that the coating agent 1722 cannot contact the channels 1701, 1702. The device 1700 is then filled with the coating agent 1722 to fill the droplet formation region and the collection reservoir 1704 (Step 3 of FIG. 17A). After the coating process is complete, the device 1700 is flushed (Step 4 of FIG. 17A) to remove both the blocking liquid 1724 from the channels and the coating agent 1722 from the droplet formation region and the collection reservoir 1704. This leaves behind a layer of the coating agent 1722 only in the regions where it is desired. This is further exemplified in the micrograph of FIG. 17B, the blocking liquid (dark gray) fills the first channel 1701 and second channel 1702, preventing ingress of the coating agent 1722 (white) into either the first channel 1701 or the second channel 1702 while completely coating the droplet formation region and the collection reservoir 1704. In this example, the first channel 1701 is also acting as a feed channel for the blocking liquid 1724, shown by the arrow for flow direction in FIG. 17B.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Other embodiments are in the claims.

What is claimed is:

1. A device for producing droplets, the device comprising:
   a) a first channel having a first depth, a first width, a first proximal end, and a first distal end;
   b) a second channel having a second depth, a second width, a second proximal end, and a second distal end, wherein the second channel intersects the first channel between the first proximal and first distal ends;
   c) a shelf region in fluid communication with the first distal end and having a third depth and a third width, wherein the third width is greater than the first width; and
   d) a step region having a wall having a depth greater than the first and third depths, wherein the shelf region is fluidically connected to the step region, and the shelf region is disposed between the first distal end and the step region,
   wherein a first liquid flowing from the first distal end and a third liquid flowing from the second distal end combine and form droplets in a second, immiscible liquid at the step region.

2. The device of claim 1, wherein the third width increases from the first distal end to the step region.

3. The device of claim 1, further comprising a first reservoir in fluid communication with the first proximal end.

4. The device of claim 1, further comprising a second reservoir in fluid communication with the second proximal end.

5. The device of claim 1, further comprising a collection reservoir in fluid communication with the step region.

6. The device of claim 1, wherein at least one of the first channel or the second channel further comprises a groove.

7. The device of claim 1, further comprising a third channel having a third proximal end and a third distal end, wherein the third proximal end is in fluid communication with the shelf region, and wherein the third distal end is in fluid communication with the step region.

8. A system for producing droplets, the system comprising:
   a) a device for producing droplets, the device comprising:
      i) a first channel having a first depth, a first width, a first proximal end, and a first distal end;
      ii) a second channel having a second depth, a second width, a second proximal end, and a second distal end, wherein the second channel intersects the first channel between the first proximal and first distal ends;
      iii) a shelf region in fluid communication with the first distal end and having a third depth and a third width, wherein the third width is greater than the first width; and
      iv) a step region having a wall having a depth greater than the first and third depths, wherein the shelf region is fluidically connected to the step region, and the shelf region is disposed between the first distal end and the step region;
      v) a first reservoir in fluid communication with the first proximal end, wherein the first reservoir comprises a first liquid; and
      vi) a second reservoir in fluid communication with the second proximal end, wherein the second reservoir comprises a third liquid, wherein the first and third liquids are miscible with each other and wherein the first and third liquids combine at the intersection of the first channel and second channel,
   b) a second liquid contained in the shelf and step regions, wherein the first liquid and the second liquid are immiscible with each other,
   wherein the combined first and third liquids, flowing from the first distal end to the step region, form droplets of the combined first and third liquids dispersed in the second liquid.

9. The system of claim 8, wherein the first liquid comprises particles.

10. The system of claim 8, wherein the third liquid comprises an analyte.

11. The system of claim 8, wherein the third width increases from the first distal end to the step region.

12. The system of claim 8, further comprising a collection reservoir in fluid communication with the step region.

13. The system of claim 8, wherein the device further comprises a third channel having a third proximal end and a third distal end, wherein the third proximal end is in fluid communication with the shelf region, and wherein the third distal end is in fluid communication with the step region.

14. A kit for producing droplets, the kit comprising:
   a) a device for producing droplets, the device comprising:
      i) a first channel having a first depth, a first width, a first proximal end, and a first distal end;
      ii) a second channel having a second depth, a second width, a second proximal end, and a second distal end, wherein the second channel intersects the first channel between the first proximal and first distal ends;
      iii) a shelf region in fluid communication with the first distal end and having a third depth and a third width, wherein the third width is greater than the first width; and
      iv) a step region having a wall having a depth greater than the first and third depths, wherein the shelf region is fluidically connected to the step region, and the shelf region is disposed between the first distal end and the step region,
      v) a first reservoir in fluid communication with the first proximal end; and
      vi) a second reservoir in fluid communication with the second proximal end,
   b) a first liquid in a reservoir;
   c) a second liquid in a reservoir, wherein the first liquid and the second liquid are immiscible with each other,
   wherein the first liquid flowing from the first distal end forms droplets in the second, immiscible liquid at the step region.

15. The kit of claim 14, wherein the first liquid comprises particles.

16. The kit of claim 14, wherein the third width increases from the first distal end to the step region.

17. The kit of claim 14, wherein the device further comprises a collection reservoir in fluid communication with the step region.

18. The kit of claim 14, wherein the device further comprises a third channel having a third proximal end and a third distal end, wherein the third proximal end is in fluid communication with the shelf region, and wherein the third distal end is in fluid communication with the step region.

* * * * *